United States Patent
Meissner et al.

(10) Patent No.: US 7,351,698 B2
(45) Date of Patent: Apr. 1, 2008

(54) ANDROGEN RECEPTOR MODULATORS AND METHODS OF USE THEREOF

(75) Inventors: Robert S. Meissner, Schwenksville, PA (US); James J. Perkins, Churchville, PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/551,975

(22) PCT Filed: May 3, 2004

(86) PCT No.: PCT/US2004/013787

§ 371 (c)(1), (2), (4) Date: Oct. 5, 2005

(87) PCT Pub. No.: WO2004/100874

PCT Pub. Date: Nov. 25, 2004

(65) Prior Publication Data

US 2006/0241107 A1    Oct. 26, 2006

Related U.S. Application Data

(60) Provisional application No. 60/468,579, filed on May 7, 2003.

(51) Int. Cl.
*A01N 57/00* (2006.01)
*A01N 43/42* (2006.01)
*A61K 31/675* (2006.01)
*A61K 31/44* (2006.01)

(52) U.S. Cl. ............ 514/80; 514/284; 546/23; 546/77

(58) Field of Classification Search ......... 514/171, 514/80, 284; 546/23, 77
See application file for complete search history.

(56) References Cited

U.S. PATENT DOCUMENTS

| | | | |
|---|---|---|---|
| 4,377,584 A | | 3/1983 | Rasmusson et al. |
| 5,359,071 A | | 10/1994 | Durette et al. |
| 5,494,914 A | | 2/1996 | Labrie et al. |
| 5,583,138 A | | 12/1996 | Tuba et al. |
| 5,583,228 A | | 12/1996 | Tuba et al. |
| 5,620,986 A | | 4/1997 | Witzel et al. |
| 5,639,741 A | * | 6/1997 | Witzel et al. .......... 514/80 |
| 5,693,809 A | | 12/1997 | Durette et al. |
| 5,710,275 A | | 1/1998 | Bakshi et al. |

FOREIGN PATENT DOCUMENTS

WO    WO 95/00531    1/1995
WO    WO 97/30069    8/1997

OTHER PUBLICATIONS

M. Lourdusamy et al., "Synthesis and In Vitro Study of 17 beta-[N-Ureylene-N,N'-distributed]-4-methyl-4-aza-5 alpha-Androstan-3-ones as Selective Inhibitors of Type I 5 alpha-Reductase", Bioorganic & Medicinal Chemistry, vol. 5, pp. 305-310, 1997.

X. Li et al., "Synthesis and in Vitro Activity of 17 beta-(N-Alkyl/arylformamido)-and 17 beta-[(N-Alkyl/aryl)alkyl/arylamido]-4-methyl-4-aza-3-oxo-5 alpha-androstan-3- . . . ", J. Med. Chem, vol. 38, pp. 1158-1173, 1995.

C. Chen et al., "Activity of 17 beta-(N-Alkyl/arylformamido) and 17 beta-[N-Alkyl/aryl)alkyl/arylamido]-4-methyl-4-aza-5a-androstan-3-ones as 5 alpha-Reductase Inhibitors in the Hamster Flank Organ and Ear", The Journal of Investigative Dermatology, vol. 111, pp. 273-278, 1998.

G.H. Rasmusson et al., "Azasteroids: Structure-Activity Relationships for Inhibition of 5 alpha-Reductase and of Androgen Receptor Binding", J. Med. Chem., vol. 29, pp. 2298-2315, 1986.

G.H. Rasmusson et al., "Azasteroids as Inhibitos of Rat Prostatic 5 alpha-Reductase", J. Med. Chem , vol. 27, pp. 1690-1701, 1984.

W.E. Solomons et al., "Synthesis and Antimicrobial Properties of 17 beta-Amino-4-aza-5 alpha-androstane and Derivatives", Journal of Pharmaceutical Sciences, vol. 63, pp. 19-23, 1974.

* cited by examiner

*Primary Examiner*—Sreeni Padmanabhan
*Assistant Examiner*—Umamaheswari Ramachandran
(74) *Attorney, Agent, or Firm*—Patricia A. Shatynski; Curtis C. Panzer; Valerie J. Camara

(57) ABSTRACT

Compounds of structural formula (I) as herein defined are disclosed as useful in a method for modulating the androgen receptor in a tissue selective manner in a patient in need of such modulation, as well as in a method of agonizing the androgen receptor in a patient, and in particular the method wherein the androgen receptor is antagonized in the prostate of a male patient or in the uterus of a female patient and agonized in bone and/or muscle tissue. These compounds are useful in the treatment of conditions caused by androgen deficiency or which can be ameliorated by androgen administration, including: osteoporosis, periodontal disease, bone fracture, bone damage following bone reconstructive surgery, sarcopenia, frailty, aging skin, male hypogonadism, post-menopausal symptoms in women, female sexual dysfunction, atherosclerosis, hypercholesterolemia, hyperlipidemia, aplastic anemia and other hematopoietic disorders, pancreatic cancer, renal cancer, arthritis and joint repair, alone or in combination with other active agents. In addition, these compounds are useful as pharmaceutical composition ingredients alone and in combination with other active agents.

1 Claim, No Drawings

ANDROGEN RECEPTOR MODULATORS AND METHODS OF USE THEREOF

This application is a §371 National Stage application of PCT/US2004/013787, filed on May 3, 2004, which claims priority from: U.S. Provisional Application No. 60/468,579 filed May 7, 2003.

CROSS-REFERENCE TO RELATED APPLICATIONS

Not applicable.

BACKGROUND OF THE INVENTION

Androgens play important roles in post-natal development that are most pronounced at adrenarche and pubarche. Androgen production promotes the musculoskeletal anabolism associated with the pubertal growth in both males and females. At puberty, ovarian and testicular androgens are responsible for pubertal hair, acne, and enhancement of libido. In males, exposure to 100-fold increased levels of endogenous androgens results in the gender dimorphism in bone mass, muscle mass (positive nitrogen balance), and upper body strength, and are required for normal sexual development (genitalia, spermatogenesis, prostate and seminal vesicle maturation). Delay in puberty decreases the peak bone mass achieved during adulthood. (Bhasin, S., et al., Eds. Pharmacology, Biology, and Clinical Applications of Androgens: Current Status and Future Prospects. Wiley-Liss, Inc.: New York, 1996). In women, natural menopause causes virtually complete loss of ovarian estrogen production and gradually reduces ovarian production of androgen by approximately 50%. The physiological consequences of reduced androgen production after menopause are evident in decreased energy and libido, and contribute significantly in many women to vasomotor symptoms. Decreased androgen output is also thought to contribute—along with declining pituitary growth hormone (GH) secretion and insulin derived growth factor 1 (IGF1) action—to age-dependent sarcopenia, negative nitrogen balance and loss of bone mass. (Vestergaard, et al., Effect of sex hormone replacement on the insulin-like growth factor system and bone mineral: a cross-sectional and longitudinal study in 595 perimenopausal women participating in the Danish Osteoporosis Prevention Study, J Clin Endocrinol Metab. 84:2286-90, 1999; and Bhasin, et al., Eds. Pharmacology, Biology, and Clinical Applications of Androgens: Current Status and Future Prospects, Wiley-Liss, Inc.: New York. 1996). Postmenopausal osteoporosis results mainly from estrogen deficiency. However, many women who received estrogen replacement therapy still lose bone with age and develop age-related osteoporotic fractures (albeit at a lower rate than those taking estrogens), indicating that both estrogens and androgens play important roles for bone health in both women and men. The simultaneous decreases in bone mass, muscle mass and muscle strength increase the risk of falls and especially of hip fractures in both men and women>65 years of age. In fact, one-third of all hip fractures occur in men.

The androgen receptor (AR) belongs to the nuclear receptor superfamily and controls transcription in a ligand dependent manner (Brinklan, et al., Mechanisms of androgen receptor activation and function, J. Ster. Biochem. Mol. Biol. 69, 307-313, 1999). Upon androgen binding, AR binds directly to specific DNA sequences present in the promoter region of androgen responsive genes, termed androgen response elements (AREs), to stimulate transcription. Using ARE-dependent transcription as a criterion, agents that bind to AR and stimulate ARE-dependent transcription can be classified as agonists, and those that bind to AR and suppress ARE-dependent transcription are classified as antagonists. A number of natural or synthetic androgen agonists have been used for treatment of musculoskeletal or hematopoietic disorders and for hormone replacement therapy. In addition, AR antagonists, such as flutamide or bicalutamide, are used for treatment of prostate cancer. However, clinical use of these androgen agonists or antagonists have been limited because of undesirable effects, such as hirsutism and prostate enlargement for agonists, and bone loss, fracture, gynecomastia and sarcopenia for antagonists. It would be useful to have available androgens with tissue selective agonistic activity, which increase bone formation and muscle mass but do not induce the virilization.

Osteoporosis is characterized by bone loss, resulting from an imbalance between bone resorption (destruction) and bone formation, which starts in the fourth decade continues throughout life at the rate of about 1-4% per year (Eastell, Treatment of postmenopausal osteoporosis, New Eng. J. Med. 338: 736, 1998). In the United States, there are currently about 20 million people with detectable fractures of the vertebrae due to osteoporosis. In addition, there are about 250,000 hip fractures per year due to osteoporosis, associated with a 12%-20% mortality rate within the first two years, while 30% of patients require nursing home care after the fracture and many never become fully ambulatory again. In postmenopausal women, estrogen deficiency leads to increased bone resorption resulting in bone loss in the vertebrae of around 5% per year, immediately following menopause. Thus, first line treatment/prevention of this condition is inhibition of bone resorption by bisphosphonates, estrogens, selective estrogen receptor modulators (SERMs) and calcitonin. However, inhibitors of bone resorption are not sufficient to restore bone mass for patients who have already lost a significant amount of bone. The increase in spinal BMD attained by bisphosphonate treatment can reach 11% after 7 years of treatment with alendronate. In addition, as the rate of bone turnover differs from site to site; higher in the trabecular bone of the vertebrae than in the cortex of the long bones, the bone resorption inhibitors are less effective in increasing hip BMD and preventing hip fracture. Therefore, osteoanabolic agents, which increase cortical/periosteal bone formation and bone mass of long bones, would address an unmet need in the treatment of osteoporosis especially for patients with high risk of hip fractures. The osteoanabolic agents also complement the bone resorption inhibitors that target the trabecular envelope, leading to a biomechanically favorable bone structure. (Schmidt, et al., Anabolic steroid: Steroid effects on bone in women, 1996, In: J. P. Bilezikian, et al., Ed. Principles of Bone Biology. San Diego: Academic Press.)

A number of studies provide the proof of principle that androgens are osteoanabolic in women and men. Anabolic steroids, such as nandrolone decanoate or stanozolol, have been shown to increase bone mass in postmenopausal women. Beneficial effects of androgens on bone in post-menopausal osteoporosis are well documented in recent studies using combined testosterone and estrogen administration (Hofbauer, et al., Androgen effects on bone metabolism: recent progress and controversies, Eur. J. Endocrinol. 140, 271-286, 1999). Combined treatment increased significantly the rate and extent of the rise in BMD (lumbar and hip), relative to treatment with estrogen alone. Additionally, estrogen-progestin combinations that incorporate an androgenic progestin (norethindrone) rather than medroxyprogesterone acetate yielded greater improvements in hip BMD. These results have recently been confirmed in a larger (N=311) 2 year, double blind comparison study in which oral conjugated estrogen (CEE) and methyltestosterone combinations were demonstrated to be effective in promoting accrual of bone mass in the spine and hip, while conjugated estrogen therapy alone prevented bone loss (A two-year, double-blind comparison of estrogen-androgen and conjugated estrogens in surgically menopausal women: Effects on bone mineral density, symptoms and lipid profiles. J Reprod Med. 44(12):1012-20, 1999). Despite the beneficial effects of androgens in postmenopausal women, the use of androgens has been limited because of the undesirable virilizing and metabolic action of androgens. The data from Watts and colleagues demonstrate that hot flushes decrease in women treated with CEE+methyltestosterone; however, 30% of these women suffered from significant increases in acne and facial hair, a complication of all current androgen pharmacotherapies (Watts, et al., Comparison of oral estrogens and estrogens plus androgen on bone mineral density, menopausal symptoms, and lipid-lipoprotein profiles in surgical menopause, Obstet. Gynecol. 85, 529-537, 1995). Moreover, the addition of methyltestosterone to CEE markedly decreased HDL levels, as seen in other studies. Thus, the current virilizing and metabolic side effect profile of androgen therapies provide a strong rationale for developing tissue selective androgen agonists for bone.

It is well established that androgens play an important role in bone metabolism in men, which parallels the role of estrogens in women. (Anderson, et al., Androgen supplementation in eugonadal men with osteoporosis—effects of 6 months of treatment on bone mineral density and cardiovascular risk factors, Bone 18: 171-177, 1996). Even in eugonadal men with established osteoporosis, the therapeutic response to testosterone treatment provides additional evidence that androgens exert important osteoanabolic effects. Mean lumbar BMD increased from 0.799 gm/cm$^2$ to 0.839 g/cm$^2$, in 5 to 6 months in response to 250 mg of testosterone ester IM q fortnight (p=0.001). A common scenario for androgen deficiency occurs in men with stage D prostate cancer (metastatic) who undergo androgen deprivation therapy (ADT). Endocrine orchiectomy is achieved by long acting GnRH agonists, while androgen receptor blockade is implemented with flutamide or bicalutamide (AR antagonists). In response to hormonal deprivation, these men suffer from hot flushes, significant bone loss, weakness, and fatigue. In a recent pilot study of men with stage D prostate cancer, osteopenia (50% vs. 38%) and osteoporosis (38% vs. 25%) were more common in men who had undergone ADT for>1 yr than the patients who did not undergo ADT (Wei, et al. Androgen deprivation therapy for prostate cancer results in significant loss of bone density, Urology 54: 607-11, 1999). Lumbar spine BMD was significantly lower in men who had undergone ADT (P=0.008). Thus, in addition to the use of tissue selective AR agonists for osteoporosis, tissue selective AR antagonists in the prostate that lack antagonistic action in bone and muscle may be a useful treatment for prostate cancer, either alone or as an adjunct to traditional ADT such as GnRH agonist/antagonist.

Additionally, it has been re ported that patients with pancreatic cancer treated with the antiandrogen flutamide have been found to have increased survival time. (Greenway, B. A., Drugs & Aging, 17(3), 161, 2000). The tissue selective androgen receptor modulators of the present invention may be employed for treatment of pancreatic cancer, either alone or as an adjunct to treatment with an antiandrogen.

The possibility of tissue selective AR agonism was suggested by androgen insensitivity syndrome (AIS), which results from mutations in AR gene located at X chromosome. (Quigley, et al., Androgen receptor defects: Historical, clinical, and molecular perspectives. Endocrine Reviews. 16: 546-546, 1995). These mutations cause different degrees of androgen insensitivity. While complete lack of androgen responsiveness develops as a female phenotype with female-type bones, subtle mutations (one amino acid substitution) of AR may lead to partial AIS with different degrees of abnormality in male sexual development often with male-type skeleton. A similar aberration in male sex organ development is also found in individuals with mutations in 5α-reductase type 2 gene, that converts testosterone to 5α-dihydro-testosterone (5α-DHT) (Mendonca, et al., Male pseudohermaphroditism due to steroid 5alpha-reductase 2 deficiency: Diagnosis, psychological evaluation, and management, Medicine (Baltimore), 75 :64-76 (1996)). These patients exhibit partial development of male organs with normal male skeleton, indicating that testosterone cannot substitute for 5α-DHT as an activator of AR in genital development. This ligand specificity for certain tissues raises the possibility that androgenic compounds with AR agonistic activity could have specificity for certain tissues, such as bone, while lacking activity in other tissues, such as those responsible for virilization.

Recent advances in the steroid hormone receptor field uncovered the complex nature of transcription controlled by AR and other nuclear receptors (Brinkman, et al., Mechanisms of androgen receptor activation and function, J. Ster. Biochem. Mol. Biol. 69, 307-313 1999). Upon binding to ARE as a homo-dimer, agonist-bound AR stimulates transcription by recruiting a large enzymatic co-activator complex that includes GRIP1/TIF2, CBP/p300 and other coactivators. Transcriptional activities of AR have been functionally mapped to both the N-terminal domain (NTD) and C-terminal ligand binding domain (LBD), also termed activation function AF1 and AF2, respectively. A feature of AR is the ligand mediated interaction of AR NTD with LBD (N-C interaction) which is essential for most ligand induced transcriptional activation. In addition, agonist-bound AR can also suppress transcription via protein-protein interaction with transcription factor complexes such as AP1, NFκB and Ets family. Both AR agonist-induced transcriptional activation and repression are context (cell type and promoter) dependent and are reversed by AR antagonists, providing the possibility for ligand-dependent, context specific agonism/antagonism. Androgenic ligands, thus, may lead to tissue selective AR agonism or partial AR agonism/antagonism, and have been named selective AR modulators (SARMs).

What is needed in the art are compounds that can produce the same positive responses as androgen replacement therapy without the undesired side effects. Also needed are androgenic compounds that exert selective effects on different tissues of the body. In this invention, we developed a method to identify SARMs using a series of in vitro cell-assays that profiles ligand mediated activation of AR, such as (i) N-C interaction, (ii) transcriptional repression, (iii) transcriptional activation dependent on AF1 or AF2 or native form of AR. SARM compounds in this invention, identified with the methods listed above, exhibit tissue selective AR agonism in vivo, i. e. agonism in bone (stimulation of bone formation in rodent model of osteoporosis) and antagonism in prostate (minimal effects on prostate growth in castrated rodents and antagonism of prostate growth induced by AR agonists). Such compounds are ideal for treatment of osteoporosis in women and men as a monotherapy or in combination with inhibitors of bone resorption, such as bisphosphonates, estrogens, SERMs, cathepsin K inhibitors, αVβ3 antagonists, calcitonin, proton pump inhibitors. SARM compounds may also be employed for treatment of prostate disease, such as prostate cancer and benign prostate hyperplasia (BPH). Moreover, compounds in this invention exhibit minimal effects on skin (acne and facial hair growth) and can be used for treatment of hirsutism. Additionally, compounds in this invention can exhibit muscle growth and can be used for treatment of sarcopenia and frailty. Moreover, compounds in this invention can exhibit androgen agonism in the central nervous system and can be used to treat vasomotor symptoms (hot flush) and can increase energy and libido, particularly in post-menopausal women. The compounds of the present invention may be used in the treatment of prostate cancer, either alone or as an adjunct to traditional GnRH agonist/antagonist therapy for their ability to restore bone, or as a replacement for antiandrogen therapy because of the ability to antagonize androgen in the prostate, and minimize bone depletion in the skeletal system. Further, the compounds of the present invention may be used for their ability to restore bone in the treatment of pancreatic cancer as an adjunct to treatment with antiandrogen, or as solo agents for their antiandrogenic properties, offering the advantage over traditional antiandrogens of being bone-sparing. Additionally, compounds in this invention can increase the number of blood cells, such as red blood cells and platelets and can be used for treatment of hematopoietic disorders such as aplastic anemia. Finally, compounds in this invention have minimal effects on lipid metabolism, thus considering their tissue selective androgen agonism listed above, the compounds in this invention are ideal for hormone replacement therapy in hypogonadic (androgen deficient) men.

U.S. Pat. No. 5,696,130; U.S. Pat. No. 5,688,808; U.S. Pat. No. 6,093,821; and WO 01/16139 disclose nonsteroidal steroid receptor modulating compounds.

WO 03/026568; WO 03/26568; WO 03/011302 and U.S. 2003/0065004 discloses androstane derivatives as androgen receptor modulators.

16- or 17β-substituted androstane derivatives are disclosed in the following: U.S. Pat. No. 4,220,775; U.S. Pat. No. 4,377,584 U.S. Pat. Nos. 5,084,574; 5,116,983; U.S. Pat. No. 5,237,064; U.S. Pat. No. 5,438,061; U.S. Pat. No. 5,620,986; U.S. Pat. No. 5,639,741; U.S. Pat. No. 5,693,809; U.S. Pat. No. 5,693,810; U.S. Pat. No. 5,696,266; U.S. Pat. No. 5,710,275; U.S. Pat. No. 5,777,134; U.S. Pat. No. 5,817,802; U.S. Pat. No. 5,994,362; US2001/0001099A1; WO 92/16213; WO 93/23038; WO 93/23039; WO 93/23048; WO 93/23053; WO 94/07909; WO 94/20104; WO 95/00531; WO 95/00532; WO 97/30069, EP 0 572 166; Solomons, et al., "Synthesis and antimicrobial properties of 17β-amino-4-aza-5α-androstane and derivatives", J. Pharm. Sci. 63(1): 19 (1974); Rasmusson, et al. "Azasteroids as Inhibitors of Rat Prostatic 5α-Reductase", J. Med. Chem. 27: 1690 (1984); Rasmusson, et al., "Azasteroids: Structure-Activity Relationships for Inhibition of 5α-Reductase and of Androgen Receptor Binding" J. Med. Chem. 29(11): 2298 (1986); Li et al., "Synthesis and in Vitro Activity of 17β-(N-Alkyl/arylformamido and N-alkyl/arylalkyl/arylamido)-4-methyl-4-aza-3-oxo-5a-androstan-3-ones as Inhibitors of Human 5a-Reductases and Antagonists of the Androgen Receptor" J. Med. Chem. 38(7): 1158 (1995); Lourdusamy et al., "Synthesis and in vitro study of 17β-[N-ureylene-N, N'-disubstituted]4-methyl-4-aza-5α-androstan-3-ones as selective inhibitors of type I 5α-reductase" Bioorg. Med. Chem. 5(2): 305 (1997); Chen et al., "Activity of 17β-(N-alkyl/arylformamido) and 17B-[N-alkyl/aryl)alkyl/arylamido]-4-methyl-4-aza-5a-androstan-3-ones as 5α-reductase inhibitors in the hamster flank organ and ear" Can. J. Invest. Dermatol. 111(2): 273 (1998).

Tolman, et al., "4-Methyl-3-oxo-4-aza-5α-androst-1-ene-17β-N-aryl-carboxamides: An Approach to Combined Androgen Blockade 5α-Reductase Inhibition with Androgen Receptor Binding In Vitro", J. Steroid Biochem. Molec. Biol. 60(5-6): 303 (1997), discloses that 4-N-methyl substitution and unsaturation of the A ring at the 1-2 position of 4-aza-5α-androstan-3-one 17β-carboxamide 5α-reductase type 2 inhibitors increased androgen receptor affinity and that N-aryl substitution at the 17-carboxamide increased affinity for the type 1 isozyme of 5α-reductase. Tolman, et al., posit that these compounds will have utility in the treatment of prostatic carcinoma and will provide complete androgen blockade.

U.S. Pat. No. 5,945,412; WO 98/25623 and WO 98/25622 are directed to the use of 5α-reductase inhibitors, including 16-substituted-5α-androstan-3-ones, finasteride and 17-alkyl-4-aza-5α-androstan-3-ones, respectively, as antiresorptive agents useful in the prevention and treatment of bone loss, as well as prevention and treatment of osteoporosis and osteopenia and other diseases where inhibiting bone loss may be beneficial, including: Paget's disease, malignant hypercalcemia, periodontal disease, joint loosening and metastatic bone disease, as well as reducing the risk of fractures, both vertebral and nonvertebral. In the treatment of osteoporosis, the activity of bone resorption inhibitors is distinct from the activity of tissue selective androgen receptor modulators (SARMs). Rather than inhibiting bone resorption, the SARMs of the present invention stimulate bone formation, acting preferentially on cortical bone, which is responsible for a significant part of bone strength. Bone resorption inhibitors, in contrast, act preferentially on trabecular bone.

SUMMARY OF THE INVENTION

Compounds of structural formula (I) as herein defined are disclosed as useful in a method for modulating the androgen receptor in a tissue selective manner in a patient in need of such modulation, as well as in a method of agonizing the androgen receptor in a patient, and in particular the method wherein the androgen receptor is agonized in bone and/or muscle tissue and antagonized in the prostate of a male patient or in the uterus of a female patient. These compounds are useful in the treatment of conditions caused by androgen deficiency or which can be ameliorated by androgen administration, including: osteoporosis, periodontal disease, bone fracture, bone damage following bone reconstructive surgery, sarcopenia, frailty, aging skin, male hypogonadism, post-menopausal symptoms in women, female sexual dysfunction, atherosclerosis, hypercholesterolemia, hyperlipidemia, aplastic anemia and other hematopoietic disorders, pancreatic cancer, renal cancer, arthritis and joint repair, alone or in combination with other active agents. In addition, these compounds are useful as pharmaceutical composition ingredients alone and in combination with other active agents.

DETAILED DESCRIPTION OF THE INVENTION

The present invention relates to compounds useful as tissue selective androgen receptor modulators (SARMs).

Compounds of the present invention, which may be prepared in accordance with the methods described herein, have been found to be tissue selective modulators of the androgen receptor (SARMs). In one aspect, compounds of the present invention may be useful to agonize the androgen receptor in a patient, and in particular to agonize the androgen receptor in bone and/or muscle tissue and antagonize the androgen receptor in the prostate of a male patient or in the uterus of a female patient and agonize the androgen receptor in bone and/or muscle tissue. In another aspect of the present invention, compounds of structural formula I may be useful to agonize the androgen receptor in bone and/or muscle tissue and antagonize the androgen receptor in the prostate of a male patient or in the uterus or skin of a female patient. The agonism in bone can be assayed through stimulation of bone formation in the rodent model of osteoporosis, and the antagonism in the prostate can be assayed through observation of minimal effects on prostate growth in castrated rodents and antagonism of prostate growth induced by AR agonists, as detailed in the Examples.

Yet another aspect of the present invention is a method to identify SARMs using a series of in vitro cell-based assays. In the first of these series of assays (which may in practice be performed in any order), agonists of the androgen receptor (AR) are characterized by measuring Rhesus AR-dependent suppression of the human MMP-1 promoter in BEP G-2 cells transiently transfected with MMP1/luciferase promoter and the Rhesus AR (RhAR). (Schneikert, et al., Androgen receptor-Ets protein interaction is a novel mechanism for steroid hormone-mediated down-modulation of matrix metalloproteinase expression, J Biol Chem. September 27:271 (39):23907-13, 1996. In this instance, the Rhesus AR mediates ligand-dependent promoter suppression of the MMP1 promoter via protein-protein interactions with uncharacterized factors bound to the Ets cognate. SARMs display agonist activity in this assay by repressing transcription. A compound's in vivo viralizing potential, mediated through the AR, is reflected in vitro by its ability to stably assemble an AR N-terminal/C-terminal interaction. (He, et al., Activation function in the human androgen receptor ligand binding domain mediates interdomain communication with the NH(2)-terminal domain. J Biol Chem. 274: 37219 1999). Two transcription assays have been developed to screen for compounds with reduced potential to induce virilizing effects in vivo. In the first transcription assay, the in vivo virilizing potential mediated by activated androgen receptors is reflected in the capacity of rhAR ligands to induce the N-terminal/C-terminal interaction in a mammalian 2-hybrid assay in CV-1 monkey kidney cells. SARMs display weak or no agonist activity in this assay. In the second transcription assay, the same test compound is assayed in the same format in the presence of a full virilizing androgen agonist and the capacity of the compound to antagonize the stimulation induced by the full androgen agonist is quantified. SARMs of the present invention display antagonist activity in in this assay.

In a further aspect of the present invention are compounds of structural formula I that antagonize the androgen receptor in the prostate of a male patient or in the uterus of a female patient, but not in hair-growing skin or vocal cords, and agonize the androgen receptor in bone and/or muscle tissue, but not in organs which control blood lipid levels (e.g. liver). These compounds are useful in the treatment of conditions caused by androgen deficiency or which can be ameliorated by androgen administration, including: osteoporosis, osteopenia, glucocorticoid-induced osteoporosis, periodontal disease, HIV-wasting, cancer cachexia, bone fracture, bone damage following bone reconstructive surgery, muscular dystrophies, sarcopenia, frailty, aging skin, male hypogonadism, post-menopausal symptoms in women, female sexual dysfunction, premature ovarian failure, autoimmune disease, atherosclerosis, hypercholesterolemia, hyperlipidemia, aplastic anemia and other hematopoietic disorders, arthritis and joint repair, alone or in combination with other active agents. Still further, the compounds of the present invention are useful in treating insulin resistence, including NIDDM, obesity and growth retardation associated with obesity, hyperinsulinemia, as well as Metabolic Syndrome, or "Syndrome X" as defined in Johannsson, J. Clin Endocrin. Metabl 82: 727-34 (1997). In addition, these compounds are useful as pharmaceutical composition ingredients alone and in combination with other active agents.

The compounds of the present invention may be used to treat conditions which are caused by androgen deficiency or which can be ameliorated by androgen administration, including, but not limited to: osteoporosis, osteopenia, glucocorticoid-induced osteoporosis, periodontal disease, HIV-wasting, cancer cachexia, bone fracture, bone damage following bone reconstructive surgery, muscular dystrophies, sarcopenia, frailty, aging skin, male hypogonadism, post-menopausal symptoms in women, female sexual dysfunction, premature ovarian failure, autoimmune disease, atherosclerosis, hypercholesterolemia, hyperlipidemia, aplastic anemia and other hematopoietic disorders, arthritis and joint repair, alone or in combination with other active agents. The compounds can also be employed to increase lean body mass and reduce the risk of insulin resistance and diabetes as well as to treat insulin resistence, including NIDDM, obesity and growth retardation associated with obesity, hyperinsulinemia, as well as Metabolic Syndrome, or "Syndrome X" as defined in Johannsson, J. Clin Endocrin. Metabl 82: 727-34 (1997). Treatment is effected by administration of a therapeutically effective amount of the compound of structural formula I to the patient in need of such treatment.

The compounds of structural formula I may also be employed as adjuncts to traditional androgen depletion therapy in the treatment of prostate cancer to restore bone, minimize bone loss, and maintain bone mineral density. In this manner, they may be employed together with traditional androgen deprivation therapy, including GnRH agonists/antagonists such as leuprolide. It is also possible that the compounds of structural formula I may be used in combination with antiandrogens such as flutamide, hydroxy-flutamide (the active form of flutamide), and Casodex™ (the trademark for ICI 176,334 from Imperial Chemical Industries PLC, presently Astra-Zeneca) in the treatment of prostate cancer.

Further, the compounds of the present invention may also be employed in the treatment of pancreatic cancer, either for their androgen antagonist properties or as an adjunct to an antiandrogen such as flutamide, hydroxy-flutamide (the active form of flutamide), and Casodex™ (the trademark for ICI 176,334).

Compounds of structural formula I have minimal negative effects on lipid metabolism, thus considering their tissue selective androgen agonism listed above, the compounds in this invention are ideal for hormone replacement therapy in hypogonadic (androgen deficient) men.

Additionally, compounds in this invention can increase the number of blood cells, such as red blood cells and platelets and can be used for treatment of hematopoietic disorders such as aplastic anemia.

Compounds of the present invention are described by the following chemical formula I:

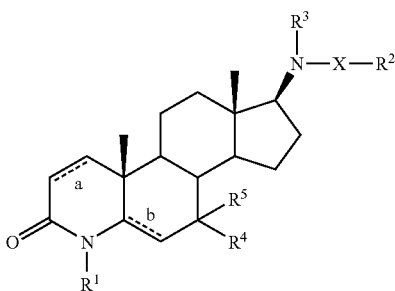

wherein:

"a" and "b" are independently selected from a single bond and a double bond;

X is selected from:
(1) —C(O)—,
(2) —C(O)—O—,
(3) —C(O)—N(R$^7$)—, and
(4) —S(O)$_n$—;

R$^1$ is selected from:
(1) C$_{1-3}$ alkyl,
(2) C$_{2-3}$ alkenyl,
(3) C$_{3-6}$ cycloalkyl,
(4) C$_{1-3}$ alkyl wherein one or more of the hydrogen atoms has been replaced with a fluorine atom,
(5) aryl, and
(6) aryl-C$_{1-3}$ alkyl;

R$^2$ is selected from:
(1) aryl, either unsubstituted or substituted,
(2) C$_{1-8}$ alkyl, unsubstituted or substituted,
(3) perfluoroC$_{1-8}$ alkyl,
(4) aryl-C$_{1-6}$ alkyl-,
(5) C$_{2-8}$ alkenyl, unsubstituted or substituted,
(6) aryl-C$_{2-8}$ alkenyl, unsubstituted or substituted,
(7) C$_{3-8}$ cycloalkyl, either unsubstituted or substituted, and
(8) cycloheteroalkyl, unsubstituted or substituted;

R$^3$ is selected from H, perfluoro C$_{1-8}$ alkyl, and C$_{1-8}$ alkyl, unsubstituted or substituted with one to three halogen atoms, or R$^2$ and R$^3$, together with the nitrogen atom, and the "X" moiety to which they are attached, form a 5- to 7-membered heterocyclic ring, optionally containing one or two additional heteroatoms selected from N, S, and O, optionally having one or more degrees of unsaturation, optionally fused to a 6-membered heteroaromatic or aromatic ring, either unsubstituted or substituted;

R$^4$ and R$^5$ are each independently selected from
(1) hydrogen,
(2) halogen,
(3) aryl,
(4) C$_{1-8}$ alkyl,
(5) C$_{3-8}$ cycloalkyl,
(6) C$_{3-8}$ cycloheteroalkyl,
(7) aryl C$_{1-6}$alkyl,
(8) amino C$_{0-6}$alkyl,
(9) C$_{1-6}$ alkylamino C$_{1-6}$alkyl,
(10) (C$_{1-6}$ alkyl)$_2$amino C$_{0-6}$alkyl,
(11) aryl C$_{0-6}$ alkylamino C$_{0-6}$alkyl,
(12) (aryl C$_{0-6}$ alkyl)$_2$amino C$_{0-6}$alkyl,
(13) C$_{1-6}$ alkylthio,
(14) aryl C$_{0-6}$alkylthio,
(15) C$_{1-6}$ alkylsulfinyl,
(16) aryl C$_{0-6}$alkylsulfinyl,
(17) C$_{1-6}$ alkylsulfonyl,
(18) aryl C$_{0-6}$alkylsulfonyl,
(19) C$_{1-6}$ alkoxy C$_{0-6}$alkyl,
(20) aryl C$_{0-6}$ alkoxy C$_{0-6}$alkyl,
(21) hydroxycarbonyl C$_{0-6}$alkyl,
(22) C$_{1-6}$ alkoxycarbonyl C$_{0-6}$alkyl,
(23) aryl C$_{0-6}$ alkoxycarbonyl C$_{0-6}$alkyl,
(24) hydroxycarbonyl C$_{1-6}$ alkyloxy,
(25) hydroxy C$_{0-6}$alkyl,
(26) cyano,
(27) nitro,
(28) perfluoroC$_{1-4}$alkyl,
(29) perfluoroC$_{1-4}$alkoxy,
(30) C$_{0-6}$ alkylcarbonyl,
(31) C$_{1-6}$ alkylcarbonyloxy,
(32) aryl C$_{0-6}$alkylcarbonyloxy,
(33) C$_{1-6}$ alkylcarbonylamino,
(34) aryl C$_{0-6}$ alkylcarbonylamino,
(35) C$_{1-6}$ alkylsulfonylamino,
(36) aryl C$_{0-6}$alkylsulfonylamino,
(37) C$_{1-6}$ alkoxycarbonylamino,
(38) aryl C$_{0-6}$ alkoxycarbonylamino,
(39) C$_{1-6}$alkylaminocarbonylamino,
(40) aryl C$_{0-6}$alkylaminocarbonylamino,
(41) (C$_{1-6}$alkyl)$_2$ aminocarbonylamino,
(42) (aryl C$_{0-6}$alkyl)$_2$ aminocarbonylamino,
(43) (C$_{1-6}$alkyl)$_2$ aminocarbonyloxy,
(44) (aryl C$_{0-6}$alkyl)$_2$ aminocarbonyloxy, and
(45) spiro-C$_{3-8}$cycloalkyl;
or, R$^4$ and R$^5$ together form an oxo group or =CH—R$^6$ or a spiro C$_{3-7}$ cycloalkyl ring, substituted with R$^6$;

R$^6$ is selected from:
(1) hydrogen, and
(2) C$_{1-4}$ alkyl;

R$^7$ is selected from H, perfluoro C$_{1-8}$ alkyl, and C$_{1-8}$ alkyl, unsubstituted or substituted with one to three halogen atoms;

n is selected from: 0, 1, and 2;

or a pharmaceutically acceptable salt thereof.

In one embodiment of the present invention, "b" is a single bond. In one class of this embodiment, "b" is a single bond, and "a" is a double bond. In another class of this embodiment, "b" is a single bond, and "a" is a single bond.

In another embodiment of the present invention, "b" is a double bond. In one class of this embodiment, "b" is a double bond, and "a" is a double bond. In another class of this embodiment, "b" is a double bond, and "a" is a single bond.

In one embodiment of the present invention, R$^1$ is selected from:
(1) C$_{1-3}$ alkyl,
(2) C$_{2-3}$ alkenyl,
(3) C$_{3-6}$ cycloalkyl,
(4) trifluoromethyl,
(5) phenyl,
(6) phenyl-C$_{1-3}$ alkyl.

In another embodiment of the present invention R$^1$ is selected from:
(1) C$_{1-3}$ alkyl,
(2) C$_{2-3}$ alkenyl,
(3) C$_{3-6}$ cycloalkyl, and
(4) trifluoromethyl.

In still another embodiment of the present invention R$^1$ is selected from:
(1) C$_{1-2}$ alkyl,
(2) C$_{3-6}$ cycloalkyl, and
(3) trifluoromethyl.

In yet another embodiment of the present invention $R^1$ is selected from:
(1) methyl,
(2) cyclopropyl, and
(3) trifluoromethyl.

In one class of this embodiment, $R^1$ is selected from methyl and cyclopropyl. In a subclass of this embodiment $R^1$ is methyl.

In one embodiment of the present invention, $R^2$ is aryl, either unsubstituted or substituted with one to three substituents selected from:
(1) halogen,
(2) aryl,
(3) $C_{1-8}$ alkyl,
(4) $C_{3-8}$ cycloalkyl,
(5) $C_{3-8}$ cycloheteroalkyl,
(6) aryl $C_{1-6}$alkyl,
(7) amino $C_{0-6}$alkyl,
(8) $C_{1-6}$ alkylamino $C_{0-6}$alkyl,
(9) $(C_{1-6}$ alkyl$)_2$amino $C_{0-6}$alkyl,
(10) aryl $C_{0-6}$ alkylamino $C_{0-6}$alkyl,
(11) (aryl $C_{0-6}$ alkyl$)_2$amino $C_{0-6}$alkyl,
(12) $C_{1-6}$ alkylthio,
(13) aryl $C_{0-6}$alkylthio,
(14) $C_{1-6}$ alkylsulfinyl,
(15) aryl $C_{0-6}$alkylsulfinyl,
(16) $C_{1-6}$ alkylsulfonyl,
(17) aryl $C_{0-6}$alkylsulfonyl,
(18) $C_{1-6}$ alkoxy $C_{0-6}$alkyl,
(19) aryl $C_{0-6}$ alkoxy $C_{0-6}$alkyl,
(20) hydroxycarbonyl $C_{0-6}$alkyl,
(21) $C_{1-6}$ alkoxycarbonyl $C_{0-6}$alkyl,
(22) aryl $C_{0-6}$ alkoxycarbonyl $C_{0-6}$alkyl,
(23) hydroxycarbonyl $C_{1-6}$ alkyloxy,
(24) hydroxy $C_{0-6}$alkyl,
(25) cyano,
(26) nitro,
(27) perfluoro$C_{1-4}$alkyl,
(28) perfluoro$C_{1-4}$alkoxy,
(29) $C_{1-6}$ alkylcarbonyloxy,
(30) aryl $C_{0-6}$alkylcarbonyloxy,
(31) alkyl $C_{1-6}$ carbonylamino,
(32) aryl $C_{0-6}$ alkylcarbonylamino,
(33) $C_{1-6}$ alkylsulfonylamino,
(34) aryl $C_{0-6}$alkylsulfonylamino,
(35) $C_{1-6}$ alkoxycarbonylamino,
(36) aryl $C_{1-6}$ alkoxycarbonylamino,
(37) $C_{1-6}$alkylaminocarbonylamino,
(38) aryl $C_{0-6}$alkylaminocarbonylamino,
(39) $(C_{1-6}$alkyl$)_2$ aminocarbonylamino,
(40) (aryl $C_{0-6}$alkyl$)_2$ aminocarbonylamino,
(41) $(C_{1-6}$alkyl$)_2$ aminocarbonyloxy,
(42) $C_{0-6}$ alkyl carbonyl $C_{0-6}$ alkyl,
(43) aryl $C_{0-6}$ alkyl carbonyl $C_{0-6}$ alkyl, and
(44) (aryl $C_{0-6}$alkyl$)_2$ aminocarbonyloxy.

In a class of this embodiment of the present invention, $R^2$ is aryl, substituted with one to three substituents selected from:
(1) halogen,
(2) aryl,
(3) $C_{1-6}$ alkyl,
(4) $C_{3-8}$ cycloheteroalkyl,
(5) benzyl,
(6) amino,
(7) $C_{1-6}$ alkylamino,
(8) $C_{1-6}$ alkylthio,
(9) $C_{1-6}$ alkoxy,
(10) hydroxy,
(11) cyano,
(12) nitro,
(13) perfluoro$C_{1-4}$alkyl,
(14) trifluoromethoxy,
(15) oxo,
(16) methylcarbonyloxy,
(17) methylcarbonylamino,
(18) methylsulfonylamino,
(19) methoxycarbonylamino,
(20) methylaminocarbonylamino,
(21) dimethylaminocarbonylamino,
(22) dimethylaminocarbonyloxy. amd
(23) methylcarbonyl.

In a subclass of this embodiment of the present invention, $R^2$ is aryl, substituted by one or two substituents selected from:
(1) halogen,
(2) methyl,
(3) $C_{1-2}$ alkoxy,
(4) hydroxy,
(5) cyano,
(6) nitro,
(7) trifluoromethyl,
(8) trifluoromethoxy,
(9) methylcarbonyl, In another subclass of this class of the present invention, $R^2$ is aryl, substituted by one substituents selected from:
(1) fluoro,
(2) chloro,
(3) bromo,
(4) methyl,
(5) methoxy,
(6) ethoxy,
(7) hydroxy,
(8) trifluoromethyl,
(9) trifluoromethoxy, and
(10) acetyl.

In one embodiment of the present invention, $R^2$ is selected from phenyl, naphthyl, pyridyl, pyrrolyl, pyrazolyl, pyrazinyl, pyrimidinyl, imidazolyl, benzimidazolyl, benzthiazolyl, benzoxazolyl, indolyl, thiophenyl, furanyl, dihydrobenzofuranyl, benzo(1,3)dioxolanyl, benzo(1,4)dioxanyl, oxazolyl, isoxazolyl, thiazolyl, isothiazolyl, indanyl, isoquinolinyl, dihydroisoquinolinyl, tetrahydronaphthyridinyl, benzothienyl, imidazopyridinyl, tetrahydrobenzazepinyl, quinoxalinyl, imidazopyrimidinyl, cyclopentenopyridinyl, phthalazinyl, tetrahydroquinolinyl, oxindolyl, isoquinolinyl, imidazothiazolyl, dihydroimidazothiazolyl, tetrazolyl, triazolyl, pyridazinyl, piperidinyl, piperazinyl, oxadiazolyl, thiadiazolyl, triazinyl, indazolyl, indazolinone, dihydrobenzofuranyl, phthalide, phthalimide, coumarin, chromone, tetrahydroisoquindine, naphthyridinyl, tetrahydronaphthyridinyl, isoindolinyl, triazanaphthalinyl, pteridinyl, purinyl, and quinolinyl.

In one class of the present invention, $R^2$ is selected from: phenyl, naphthyl, quinolinyl, pyridyl, furanyl, thiophenyl, thiazolyl, pyrimidyl, oxazolyl, furanyl, and pyridazinyl, unsubstituted or substituted.

In a subclass of this class of the invention, $R^2$ is phenyl.

In another embodiment of the present invention, $R^2$ is $C_{1-8}$ alkyl, unsubstituted or substituted with one to three substituents independently selected from:
(1) halogen,
(2) $C_{1-8}$ alkyl,
(3) $C_{3-8}$ cycloalkyl,
(4) $C_{3-8}$ cycloheteroalkyl, (5) amino,
(6) $C_{1-6}$ alkylamino,
(7) $(C_{1-6}$ alkyl$)_2$amino,
(8) aryl $C_{0-6}$ alkylamino,
(9) (aryl $C_{0-6}$ alkyl$)_2$amino,
(10) $C_{1-6}$ alkylthio,
(11) aryl $C_{0-6}$alkylthio,
(12) $C_{1-6}$ alkylsulfinyl,
(13) aryl $C_{0-6}$alkylsulfinyl,
(14) $C_{1-6}$ alkylsulfonyl,
(15) aryl $C_{0-6}$alkylsulfonyl,
(16) $C_{1-6}$ alkoxy,
(17) aryl $C_{0-6}$ alkoxy,
(18) hydroxycarbonyl,
(19) $C_{1-6}$ alkoxycarbonyl,
(20) aryl $C_{0-6}$ alkoxycarbonyl,
(21) hydroxycarbonyl $C_{1-6}$ alkyloxy,
(22) hydroxy,
(23) cyano,
(24) nitro,
(25) perfluoro$C_{1-4}$alkyl,
(26) perfluoro$C_{1-4}$alkoxy,
(27) oxo,
(28) $C_{1-6}$ alkylcarbonyloxy,
(29) aryl $C_{0-6}$alkylcarbonyloxy,
(30) alkyl $C_{1-6}$ carbonylamino,
(31) aryl $C_{0-6}$ alkylcarbonylamino,
(32) $C_{1-6}$ alkylsulfonylamino,
(33) aryl $C_{0-6}$alkylsulfonylamino,
(34) $C_{1-6}$ alkoxycarbonylamino,
(35) aryl $C_{0-6}$ alkoxycarbonylamino,
(36) $C_{1-6}$alkylaminocarbonylamino,
(37) aryl $C_{0-6}$alkylaminocarbonylamino,
(38) $(C_{1-6}$alkyl$)_2$ aminocarbonylamino,
(39) (aryl $C_{0-6}$alkyl$)_2$ aminocarbonylamino,
(40) $(C_{1-6}$alkyl$)_2$ aminocarbonyloxy,
(41) (aryl $C_{0-6}$alkyl$)_2$ aminocarbonyloxy, and
(42) spiro-$C_{3-8}$cycloalkyl.

In a class of this embodiment of the present invention, $R^2$ is $C_{1-6}$ alkyl, unsubstituted or substituted with one to three substituents independently selected from:
(1) fluoro,
(2) chloro,
(3) $C_{3-6}$ cycloalkyl,
(4) $C_{3-6}$ cycloheteroalkyl,
(5) amino,
(6) $C_{1-6}$ alkylamino,
(7) $(C_{1-6}$ alkyl$)_2$amino,
(8) aryl $C_{0-6}$ alkylamino,
(9) (aryl $C_{0-6}$ alkyl$)_2$amino,
(10) $C_{1-6}$ alkylthio,
(11) aryl $C_{0-1}$alkylthio,
(12) $C_{1-6}$ alkylsulfinyl,
(13) aryl $C_{0-1}$alkylsulfinyl,
(14) $C_{1-6}$ alkylsulfonyl,
(15) aryl $C_{0-1}$alkylsulfonyl,
(16) $C_{1-6}$ alkoxy,
(17) aryl $C_{0-1}$ alkoxy,
(18) hydroxycarbonyl,
(19) $C_{1-6}$ alkoxycarbonyl,
(20) aryl $C_{0-1}$ alkoxycarbonyl,
(21) hydroxycarbonyl $C_{1-6}$ alkyloxy,
(22) hydroxy,
(23) cyano,
(24) nitro,
(25) perfluoro$C_{1-4}$alkyl,
(26) trifluoromethoxy,
(27) oxo,
(28) $C_{1-6}$ alkylcarbonyloxy,
(29) aryl $C_{0-1}$alkylcarbonyloxy,
(30) $C_{1-6}$ alkylcarbonylamino,
(31) aryl $C_{0-1}$ alkylcarbonylamino,
(32) $C_{1-6}$ alkylsulfonylamino,
(33) aryl $C_{0-1}$alkylsulfonylamino,
(34) $C_{1-6}$ alkoxycarbonylamino,
(35) aryl $C_{0-1}$ alkoxycarbonylamino,
(36) $C_{1-6}$alkylaminocarbonylamino,
(37) aryl $C_{0-1}$alkylaminocarbonylamino,
(38) $(C_{1-6}$alkyl$)_2$ aminocarbonylamino,
(39) (aryl $C_{0-1}$alkyl$)_2$ aminocarbonylamino,
(40) $(C_{1-6}$alkyl$)_2$ aminocarbonyloxy,
(41) (aryl $C_{0-1}$alkyl$)_2$ aminocarbonyloxy, and
(42) spiro-cyclopropyl.

In a subclass of this class of the present invention, $R^2$ is $C_{1-6}$ alkyl, unsubstituted or substituted with one or two substituents independently selected from:
(1) fluoro,
(2) chloro,
(3) cyano,
(4) methoxy,
(5) hydroxy, and
(6) trifluoromethyl.

In another subclass of this embodiment of the present invention, $R^2$ is selected from:
(1) methyl,
(2) ethyl,
(3) n-propyl,
(4) isopropyl,
(5) n-butyl,
(6) sec-butyl,
(7) t-butyl, and
(8) n-hexyl, unsubstituted or substituted with one or two substituents independently selected from:
(a) fluoro,
(b) chloro,
(c) cyano,
(d) methoxy,
(e) hydroxy, and
(f) trifluoromethyl.

In another embodiment of the present invention, $R^2$ is perfluoro$C_{1-8}$ alkyl. In one class of this embodiment of the present invention $R^2$ is perfluoro$C_{1-3}$ alkyl. In a subclass of this embodiment of the present invention, $R^2$ is trifluoromethyl.

In yet another embodiment of the present invention, $R^2$ is aryl-$C_{1-6}$ alkyl-, wherein aryl is unsubstituted or substituted with 1 to 3 substituents independently selected from:
(1) halogen,
(2) $C_{1-8}$ alkyl,
(3) $C_{3-8}$ cycloalkyl,
(4) aryl,
(5) aryl $C_{1-3}$ alkyl-,
(6) amino,
(7) amino $C_{1-6}$ alkyl-,
(8) $C_{1-3}$ acylamino,
(9) $C_{1-3}$ acylamino $C_{1-6}$ alkyl,
(10) $C_{1-6}$ alkylamino,
(11) $C_{1-6}$ alkylamino $C_{1-6}$ alkyl,
(12) di$(C_{1-6})$ alkylamino,
(13) di$(C_{1-6})$ alkylamino-$C_{1-6}$ alkyl,
(14) $C_{1-4}$ alkoxy,
(15) $C_{1-4}$ alkylthio,

(16) $C_{1-4}$ alkylsulfinyl,
(17) $C_{1-4}$ alkylsulfonyl,
(18) $C_{1-4}$ alkoxy $C_{1-6}$ alkyl,
(19) hydroxycarbonyl,
(20) hydroxycarbonyl $C_{1-6}$ alkyl,
(21) $C_{1-5}$ alkoxycarbonyl,
(22) $C_{1-3}$ alkoxycarbonyl $C_{1-6}$ alkyl,
(23) hydroxycarbonyl $C_{1-6}$ alkyloxy,
(24) hydroxy,
(25) hydroxy $C_{1-6}$ alkyl,
(26) cyano,
(27) nitro,
(28) trifluoromethyl,
(29) trifluoromethoxy,
(30) $C_{1-5}$ alkylcarbonyloxy;

and wherein alkyl is substituted with one to three substituents selected from:
(1) halogen,
(2) $C_{3-8}$ cycloalkyl,
(3) $C_{3-8}$ cycloheteroalkyl,
(4) amino,
(5) $C_{1-6}$ alkylamino,
(6) ($C_{1-6}$ alkyl)$_2$amino,
(7) aryl $C_{0-6}$ alkylamino,
(8) (aryl $C_{0-6}$ alkyl)$_2$amino,
(9) $C_{1-6}$ alkylthio,
(10) aryl $C_{0-6}$ alkylthio,
(11) $C_{1-6}$ alkylsulfinyl,
(12) aryl $C_{0-6}$alkylsulfinyl,
(13) $C_{1-6}$ alkylsulfonyl,
(14) aryl $C_{0-6}$ alkylsulfonyl,
(15) $C_{1-6}$ alkoxy,
(16) aryl $C_{0-6}$ alkoxy,
(17) hydroxycarbonyl,
(18) $C_{1-6}$ alkoxycarbonyl,
(19) aryl $C_{0-6}$ alkoxycarbonyl,
(20) hydroxycarbonyl $C_{1-6}$ alkyloxy,
(21) hydroxy,
(22) cyano,
(23) nitro,
(24) trifluoroalkyl,
(25) trifluoroalkoxy,
(26) oxo,
(27) $C_{1-6}$ alkylcarbonyloxy,
(28) aryl $C_{0-6}$ alkylcarbonyloxy,
(29) $C_{1-6}$ alkylcarbonylamino,
(30) aryl $C_{0-6}$ alkylcarbonylamino,
(31) $C_{1-6}$ alkylsulfonylamino,
(32) aryl $C_{0-6}$ alkylsulfonylamino,
(33) $C_{1-6}$ alkoxycarbonylamino,
(34) aryl $C_{0-6}$ alkoxycarbonylamino,
(35) $C_{1-6}$ alkylaminocarbonylamino,
(36) aryl $C_{0-6}$ alkylaminocarbonylamino,
(37) ($C_{1-6}$ alkyl)$_2$ aminocarbonylamino,
(38) (aryl $C_{0-6}$ alkyl)$_2$ aminocarbonylamino,
(39) ($C_{1-6}$ alkyl)$_2$ aminocarbonyloxy,
(40) (aryl $C_{0-6}$ alkyl)$_2$ aminocarbonyloxy, and
(41) spiro-$C_{3-8}$ cycloalkyl.

In one class of this embodiment, $R^2$ is phenyl-$C_{1-6}$ alkyl-, wherein phenyl is unsubstituted or substituted with one or two substituents independently selected from:
(1) halogen,
(2) $C_{1-3}$ alkyl,
(3) $C_{3-6}$ cycloalkyl,
(4) phenyl,
(5) phenyl $C_{1-3}$ alkyl-,
(6) amino,
(7) amino $C_{1-6}$ alkyl-,
(8) $C_{1-3}$ acylamino,
(9) $C_{1-3}$ acylamino $C_{1-6}$ alkyl,
(10) $C_{1-6}$ alkylamino,
(11) $C_{1-6}$ alkylamino $C_{1-6}$ alkyl,
(12) di($C_{1-6}$) alkylamino,
(13) di($C_{1-6}$) alkylamino-$C_{1-6}$ alkyl,
(14) $C_{1-2}$ alkoxy,
(15) $C_{1-2}$ alkylthio,
(16) $C_{1-2}$ alkylsulfinyl,
(17) $C_{1-2}$ alkylsulfonyl,
(18) $C_{1-2}$ alkoxy $C_{1-6}$ alkyl,
(19) hydroxycarbonyl,
(20) hydroxycarbonyl $C_{1-6}$ alkyl,
(21) $C_{1-5}$ alkoxycarbonyl,
(22) $C_{1-3}$ alkoxycarbonyl $C_{1-6}$ alkyl,
(23) hydroxycarbonyl $C_{1-6}$ alkyloxy,
(24) hydroxy,
(25) hydroxy $C_{1-6}$ alkyl,
(26) cyano,
(27) nitro,
(28) trifluoromethyl,
(29) trifluoromethoxy, and
(30) $C_{1-5}$ alkylcarbonyloxy;

and wherein alkyl is substituted with one to three substituents selected from:
(1) halogen,
(2) $C_{3-8}$ cycloalkyl,
(3) $C_{3-8}$ cycloheteroalkyl,
(4) amino,
(5) methylalkylamino,
(6) dimethylamino,
(7) phenylamino,
(8) (phenyl)$_2$amino,
(9) methylthio,
(10) phenylthio,
(11) methylsulfinyl,
(12) phenylsulfinyl,
(13) methylsulfonyl,
(14) phenylsulfonyl,
(15) $C_{1-3}$ alkoxy,
(16) benzyloxy,
(17) hydroxycarbonyl,
(18) methyloxycarbonyl,
(19) phenyloxycarbonyl,
(20) hydroxycarbonyl $C_{1-6}$ alkyloxy,
(21) hydroxy,
(22) cyano,
(23) nitro,
(24) trifluoroalkyl,
(25) trifluoroalkoxy,
(26) oxo,
(27) methylcarbonyloxy,
(28) phenylcarbonyloxy,
(29) methylcarbonylamino,
(30) phenylcarbonylamino,
(31) methylsulfonylamino,
(32) phenylsulfonylamino,
(33) methoxycarbonylamino,
(34) phenyloxycarbonylamino,
(35) dimethylaminocarbonylamino,
(36) phenylaminocarbonylamino,
(37) dimethyl aminocarbonylamino,
(38) diphenyl aminocarbonylamino,
(39) dimethyl aminocarbonyloxy,
(40) diphenyl aminocarbonyloxy, and
(41) spiro-$C_{3-8}$ cycloalkyl.

In one class of this embodiment, $R^2$ is phenyl-$C_{1-6}$ alkyl-, wherein phenyl is unsubstituted or substituted with one or two substituents independently selected from:
(1) halogen,
(2) methyl,
(3) $C_{1-2}$ alkoxy,
(4) hydroxy,
(5) nitro,
(6) trifluoromethyl, and
(7) trifluoromethoxy.

In still another embodiment of the present invention, $R^2$ is $C_{2-8}$ alkenyl, unsubstituted or substituted with one to three substituents independently selected from:
(a) halogen,
(b) $C_{1-8}$ alkyl,
(c) $C_{3-8}$ cycloalkyl,
(d) $C_{3-8}$ cycloheteroalkyl,
(e) amino,
(f) $C_{1-6}$ alkylamino,
(g) ($C_{1-6}$ alkyl)$_2$amino,
(h) aryl $C_{0-6}$ alkylamino,
(i) (aryl $C_{0-6}$ alkyl)$_2$amino,
(j) $C_{1-6}$ alkylthio,
(k) aryl $C_{0-6}$alkylthio,
(l) $C_{1-6}$ alkylsulfinyl,
(m) aryl $C_{0-6}$alkylsulfinyl,
(n) $C_{1-6}$ alkylsulfonyl,
(o) aryl $C_{0-6}$alkylsulfonyl,
(p) $C_{1-6}$ alkoxy,
(q) aryl $C_{0-6}$ alkoxy,
(r) hydroxycarbonyl,
(s) $C_{1-6}$ alkoxycarbonyl,
(t) aryl $C_{0-6}$ alkoxycarbonyl,
(u) hydroxycarbonyl $C_{1-6}$ alkyloxy,
(v) hydroxy,
(w) cyano,
(x) nitro,
(y) perfluoro$C_{1-4}$alkyl,
(z) perfluoro$C_{1-4}$alkoxy,
(aa) oxo,
(bb) $C_{1-6}$ alkylcarbonyloxy,
(cc) aryl $C_{0-6}$alkylcarbonyloxy,
(dd) $C_{1-6}$ alkylcarbonylamino,
(ee) aryl $C_{0-6}$ alkylcarbonylamino,
(ff) $C_{1-6}$ alkylsulfonylamino,
(gg) aryl $C_{0-6}$alkylsulfonylamino,
(hh) $C_{1-6}$ alkoxycarbonylamino,
(ii) aryl $C_{0-6}$ alkoxycarbonylamino,
(jj) $C_{1-6}$alkylaminocarbonylamino,
(kk) aryl $C_{0-6}$alkylaminocarbonylamino,
(ll) ($C_{1-6}$alkyl)$_2$ aminocarbonylamino,
(mm) (aryl $C_{0-6}$alkyl)$_2$ aminocarbonylamino,
(nn) ($C_{1-6}$alkyl)$_2$ aminocarbonyloxy,
(oo) (aryl $C_{0-6}$alkyl)$_2$ aminocarbonyloxy, and
(pp) spiro-$C_{3-8}$cycloalkyl.

In one class of this embodiment of the present invention, $R^2$ is $C_{2-3}$ alkenyl, unsubstituted or substituted with one to two substituents independently selected from:
(a) fluoro,
(b) chloro,
(c) methyloxy,
(d) hydroxy,
(e) cyano,
(f) nitro,
(g) trifluoromethyl,
(h) trifluoromethoxy, and
(i) oxo.

In one subclass of this class of this embodiment of the present invention, $R^2$ is $C_{2-3}$ alkenyl.

In still another embodiment of the present invention, $R^2$ is aryl $C_{2-8}$ alkenyl, wherein aryl is unsubstituted or substituted with one to three substituents independently selected from:
(1) halogen,
(2) $C_{1-8}$ alkyl,
(3) $C_{3-8}$ cycloalkyl,
(4) aryl,
(5) aryl $C_{1-3}$ alkyl-,
(6) amino,
(7) amino $C_{1-6}$ alkyl-,
(8) $C_{1-3}$ acylamino,
(9) $C_{1-3}$ acylamino $C_{1-6}$ alkyl,
(10) $C_{1-6}$ alkylamino,
(11) $C_{1-6}$ alkylamino $C_{1-6}$ alkyl,
(12) di($C_{1-6}$) alkylamino,
(13) di($C_{1-6}$) alkylamino-$C_{1-6}$ alkyl,
(14) $C_{1-4}$ alkoxy,
(15) $C_{1-4}$ alkylthio,
(16) $C_{1-4}$ alkylsulfinyl,
(17) $C_{1-4}$ alkylsulfonyl,
(18) $C_{1-4}$ alkoxy $C_{1-6}$ alkyl,
(19) hydroxycarbonyl,
(20) hydroxycarbonyl $C_{1-6}$ alkyl,
(21) $C_{1-5}$ alkoxycarbonyl,
(22) $C_{1-3}$ alkoxycarbonyl $C_{1-6}$ alkyl,
(23) hydroxycarbonyl $C_{1-6}$ alkyloxy,
(24) hydroxy,
(25) hydroxy $C_{1-6}$ alkyl,
(26) cyano,
(27) nitro,
(28) trifluoromethyl,
(29) trifluoromethoxy, and
(30) $C_{1-5}$ alkylcarbonyloxy.

In a class of this embodiment, $R^2$ is phenyl $C_{2-8}$ alkenyl, wherein phenyl is unsubstituted or substituted with one to three substituents independently selected from:
(1) halogen,
(2) $C_{1-3}$ alkyl,
(3) $C_{3-6}$ cycloalkyl,
(4) phenyl,
(5) phenyl $C_{1-3}$ alkyl-,
(6) amino,
(7) amino $C_{1-6}$ alkyl-,
(8) $C_{1-3}$ acylamino,
(9) $C_{1-3}$ acylamino $C_{1-6}$ alkyl,
(10) $C_{1-6}$ alkylamino,
(11) $C_{1-6}$ alkylamino $C_{1-6}$ alkyl,
(12) di($C_{1-6}$) alkylamino,
(13) di($C_{1-6}$) alkylamino-$C_{1-6}$ alkyl,
(14) $C_{1-2}$ alkoxy,
(15) $C_{1-2}$ alkylthio,
(16) $C_{1-2}$ alkylsulfinyl,
(17) $C_{1-2}$ alkylsulfonyl,
(18) $C_{1-2}$ alkoxy $C_{1-6}$ alkyl,
(19) hydroxycarbonyl,
(20) hydroxycarbonyl $C_{1-6}$ alkyl,
(21) $C_{1-5}$ alkoxycarbonyl,
(22) $C_{1-3}$ alkoxycarbonyl $C_{1-6}$ alkyl,
(23) hydroxycarbonyl $C_{1-6}$ alkyloxy,
(24) hydroxy,
(25) hydroxy $C_{1-6}$ alkyl,
(26) cyano,
(27) nitro,
(28) trifluoromethyl,

(29) trifluoromethoxy, and
(30) $C_{1-5}$ alkylcarbonyloxy;

In a subclass of this class, $R^2$ is phenyl $C_{2-3}$ alkenyl, wherein phenyl is unsubstituted or substituted with one to two substituents independently selected from:
(1) halogen,
(2) methyl,
(3) $C_{1-2}$ alkoxy,
(4) hydroxy,
(5) nitro,
(6) trifluoromethyl, and
(7) trifluoromethoxy.

In another subclass of this class, $R^2$ is phenyl ethenyl, wherein phenyl is unsubstituted or substituted with a substituent selected from:
(1) halogen,
(2) methyl, and
(3) trifluoromethyl.

In yet still another embodiment of the present invention, $R^2$ is $C_{3-8}$ cycloalkyl, either unsubstituted or substituted with one to three substituents selected from:
(1) halogen,
(2) aryl,
(3) $C_{1-8}$ alkyl,
(4) $C_{3-8}$ cycloalkyl,
(5) $C_{3-8}$ cycloheteroalkyl,
(6) aryl $C_{1-6}$alkyl,
(7) amino $C_{0-6}$alkyl,
(8) $C_{1-6}$ alkylamino $C_{0-6}$alkyl,
(9) ($C_{1-6}$ alkyl)$_2$amino $C_{0-6}$alkyl,
(10) aryl $C_{0-6}$ alkylamino $C_{0-6}$alkyl,
(11) (aryl $C_{0-6}$ alkyl)$_2$amino $C_{0-6}$alkyl,
(12) $C_{1-6}$ alkylthio,
(13) aryl $C_{0-6}$alkylthio,
(14) $C_{1-6}$ alkylsulfinyl,
(15) aryl $C_{0-6}$alkylsulfinyl,
(16) $C_{1-6}$ alkylsulfonyl,
(17) aryl $C_{0-6}$alkylsulfonyl,
(18) $C_{1-6}$ alkoxy $C_{0-6}$alkyl,
(19) aryl $C_{0-6}$ alkoxy $C_{0-6}$alkyl,
(20) hydroxycarbonyl $C_{0-6}$alkyl,
(21) $C_{1-6}$ alkoxycarbonyl $C_{0-6}$alkyl,
(22) aryl $C_{0-6}$ alkoxycarbonyl $C_{0-6}$alkyl,
(23) hydroxycarbonyl $C_{1-6}$ alkyloxy,
(24) hydroxy $C_{0-6}$alkyl,
(25) cyano,
(26) nitro,
(27) perfluoro$C_{1-4}$alkyl,
(28) perfluoro$C_{1-4}$alkoxy,
(29) oxo,
(30) $C_{1-6}$ alkylcarbonyloxy,
(31) aryl $C_{0-6}$alkylcarbonyloxy,
(32) alkyl $C_{1-6}$ carbonylamino,
(33) aryl $C_{0-6}$ alkylcarbonylamino,
(34) $C_{1-6}$ alkylsulfonylamino,
(35) aryl $C_{0-6}$alkylsulfonylamino,
(36) $C_{1-6}$ alkoxycarbonylamino,
(37) aryl $C_{0-6}$ alkoxycarbonylamino,
(38) $C_{1-6}$alkylaminocarbonylamino,
(39) aryl $C_{0-6}$alkylaminocarbonylamino,
(40) ($C_{1-6}$alkyl)$_2$ aminocarbonylamino,
(41) (aryl $C_{0-6}$alkyl)$_2$ aminocarbonylamino,
(42) ($C_{1-6}$alkyl)$_2$ aminocarbonyloxy,
(43) (aryl $C_{0-6}$alkyl)$_2$ aminocarbonyloxy,
(44) $C_{0-6}$ alkylcarbonyl $C_{0-6}$ alky, and
(45) spiro-$C_{3-8}$cycloalkyl.

In a class of this embodiment, $R^2$ is $C_{3-8}$ cycloalkyl, either unsubstituted or substituted with one to three substituents selected from:
(1) halogen,
(2) phenyl,
(3) $C_{1-46}$ alkyl,
(4) $C_{3-8}$ cycloheteroalkyl,
(5) benzyl,
(6) amino,
(7) $C_{1-4}$ alkylamino,
(8) $C_{1-4}$ alkylthio,
(9) $C_{1-4}$ alkoxy,
(10) hydroxy,
(11) cyano,
(12) nitro,
(13) perfluoro$C_{1-4}$alkyl,
(14) trifluoromethoxy,
(15) oxo,
(16) methylcarbonyloxy,
(17) methylcarbonylamino,
(18) methylsulfonylamino,
(19) methoxycarbonylamino,
(20) methylaminocarbonylamino,
(21) dimethylaminocarbonylamino,
(22) dimethylaminocarbonyloxy, and
(23) spiro $C_{3-8}$ cycloalkyl.

In a subclass of this class of the present invention, $R^2$ is selected from cyclopropyl and cyclohexyl, either unsubstituted or substituted with one to three substituents selected from:
(1) fluoro,
(2) phenyl,
(3) methyl,
(4) trifluoromethyl,
(5) methoxy,
(6) hydroxy,
(7) oxo, and
(8) spiro $C_{3-8}$ cycloalkyl.

In another subclass of this class of the present invention, $R^2$ is selected from cyclopropyl and cyclohexyl, either unsubstituted or substituted with one to two substituents selected from:
(a) fluoro,
(b) chloro,
(c) phenyl,
(d) methyl,
(e) $C_{1-3}$ alkylamino,
(f) $C_{1-3}$ alkoxy,
(g) hydroxy,
(h) trifluoromethyl,
(i) trifluoromethoxy, and
(j) oxo.

In another embodiment of the present invention, $R^2$ is cycloheteroalkyl, unsubstituted or substituted with one to three substituents selected from:
(a) halogen,
(b) aryl,
(c) $C_{1-8}$ alkyl,
(d) $C_{3-8}$ cycloalkyl,
(e) $C_{3-8}$ cycloheteroalkyl,
(f) aryl $C_{1-6}$alkyl,
(g) amino $C_{0-6}$alkyl,
(h) $C_{1-6}$ alkylamino $C_{0-6}$alkyl,
(i) ($C_{1-6}$ alkyl)$_2$amino $C_{0-6}$alkyl,
(j) aryl $C_{0-6}$ alkylamino $C_{0-6}$alkyl,
(k) (aryl $C_{0-6}$ alkyl)$_2$amino $C_{0-6}$alkyl,
(l) $C_{1-6}$ alkylthio, (m) aryl $C_{0-6}$alkylthio,
(n) $C_{1-6}$ alkylsulfinyl,
(o) aryl $C_{0-6}$alkylsulfinyl,
(p) $C_{1-6}$ alkylsulfonyl,
(q) aryl $C_{0-6}$alkylsulfonyl,
(r) $C_{1-6}$ alkoxy $C_{0-6}$alkyl,
(s) aryl $C_{0-6}$ alkoxy $C_{0-6}$alkyl,
(t) hydroxycarbonyl $C_{0-6}$alkyl,
(u) $C_{1-6}$ alkoxycarbonyl $C_{0-6}$alkyl,
(v) aryl $C_{0-6}$ alkoxycarbonyl $C_{0-6}$alkyl,
(w) hydroxycarbonyl $C_{1-6}$ alkyloxy,
(x) hydroxy $C_{0-6}$alkyl,
(y) cyano,
(z) nitro,
(aa) perfluoro$C_{1-4}$alkyl,
(bb) perfluoro$C_{1-4}$alkoxy,
(cc) oxo,
(dd) $C_{1-6}$ alkylcarbonyloxy,
(ee) aryl $C_{0-6}$alkylcarbonyloxy,
(ff) $C_{1-6}$ alkylcarbonylamino,
(gg) aryl $C_{0-6}$ alkylcarbonylamino,
(hh) $C_{1-6}$ alkylsulfonylamino,
(ii) aryl $C_{0-6}$alkylsulfonylamino,
(jj) $C_{1-6}$ alkoxycarbonylamino,
(kk) aryl $C_{0-6}$ alkoxycarbonylamino,
(ll) $C_{1-6}$alkylaminocarbonylamino,
(mm) aryl $C_{0-6}$alkylaminocarbonylamino,
(nn) ($C_{1-6}$alkyl)$_2$ aminocarbonylamino,
(oo) (aryl $C_{0-6}$alkyl)$_2$ aminocarbonylamino,
(pp) ($C_{1-6}$alkyl)$_2$ aminocarbonyloxy,
(qq) (aryl $C_{0-6}$alkyl)$_2$ aminocarbonyloxy,
(rr) $C_{0-6}$ alkylcarbonyl$C_{0-6}$ alkyl, and
(ss) spiro-$C_{3-8}$cycloalkyl;

provided that any heteroatom substituent is bonded to a carbon atom in the cycloheteroalkyl ring.

In one class of this embodiment of the present invention, $R^2$ is cycloheteroalkyl, unsubstituted or substituted with one to two substituents selected from:
(a) fluoro,
(b) chloro,
(c) phenyl,
(d) $C_{1-4}$ alkyl,
(e) benzyl,
(f) amino,
(g) $C_{1-6}$ alkylamino,
(h) $C_{1-6}$ alkylthio,
(i) $C_{1-6}$ alkoxy,
(j) hydroxy,
(k) cyano,
(l) nitro,
(m) perfluoro$C_{1-4}$alkyl,
(n) trifluoromethoxy,
(o) oxo,
(p) methylcarbonyloxy,
(q) methylcarbonylamino,
(r) methylsulfonylamino,
(s) methoxycarbonylamino,
(t) methylaminocarbonylamino,
(u) dimethylaminocarbonylamino,
(v) dimethylaminocarbonyloxy, and
(w) spiro $C_{3-8}$ cycloalkyl, provided that any heteroatom substituent is bonded to a carbon atom in the cycloheteroalkyl ring.

In a subclass of this class of the present invention, $R^2$ is cycloheteroalkyl, either unsubstituted or substituted with one or two substituents selected from:

(a) fluoro,
(b) phenyl,
(c) $C_{1-4}$ alkyl,
(d) $C_{1-3}$ alkoxy,
(e) hydroxy,
(f) trifluoromethyl,
(g) oxo, and
(h) spiro $C_{3-8}$ cycloalkyl;

provided that any heteroatom substituent is bonded to a carbon atom in the cycloheteroalkyl ring.

In another subclass of this class of the present invention, $R^2$ is cycloheteroalkyl, either unsubstituted or substituted with one or two substituents selected from:
(a) fluoro,
(b) chloro,
(c) phenyl,
(d) $C_{1-4}$ alkyl,
(e) $C_{1-3}$ alkoxy,
(f) hydroxy,
(g) trifluoromethyl,
(h) trifluoromethoxy, and
(i) oxo.

provided that any heteroatom substituent is bonded to a carbon atom in the cycloheteroalkyl ring.

In one subclass, $R^2$ is selected from piperidinyl, pyrrolidinyl, azetidinyl, morpholinyl, piperazinyl, tetrahydrofuranyl, and octahydroquinolizinyl, either unsubstituted or substituted. In another subclass, $R^2$ is selected from: tetrahydrofuranyl, piperidinyl, pyrrolidinyl, morpholinyl, and octahydro-2H-quinolizinyl, either unsubstituted or substituted. In still another subclass of the present invention, $R^2$ is tetrahydrofuranyl.

$R^3$ is selected from H, perfluoro $C_{1-8}$ alkyl, and $C_{1-8}$ alkyl, unsubstituted or substituted with one to three halogen atoms, or $R^2$ and $R^3$, together with the nitrogen atom and "X" moiety to which they are attached, form a 5- to 7-membered heterocyclic ring, optionally containing one or two additional heteroatoms selected from N, S, and O, optionally having one or more degrees of unsaturation, optionally fused to a 6-membered heteroaromatic or aromatic ring, either unsubstituted or substituted with one to three substituents selected from:
(1) halogen,
(2) aryl,
(3) $C_{1-8}$alkyl,
(4) $C_{3-8}$ cycloalkyl,
(5) $C_{3-8}$ cycloheteroalkyl,
(6) aryl $C_{1-6}$alkyl,
(7) amino $C_{0-6}$alkyl,
(8) $C_{1-6}$ alkylamino $C_{0-6}$alkyl,
(9) ($C_{1-6}$ alkyl)$_2$amino $C_{0-6}$alkyl,
(10) aryl $C_{0-6}$ alkylamino $C_{0-6}$alkyl,
(11) (aryl $C_{0-6}$ alkyl)$_2$amino $C_{0-6}$alkyl,
(12) $C_{1-6}$ alkylthio,
(13) aryl $C_{0-6}$alkylthio,
(14) $C_{1-6}$ alkylsulfinyl,
(15) aryl $C_{0-6}$alkylsulfinyl,
(16) $C_{1-6}$ alkylsulfonyl,
(17) aryl $C_{0-6}$alkylsulfonyl,
(18) $C_{1-6}$ alkoxy $C_{0-6}$alkyl,
(19) aryl $C_{0-6}$ alkoxy $C_{0-6}$alkyl,
(20) hydroxycarbonyl $C_{0-6}$alkyl,
(21) $C_{1-6}$ alkoxycarbonyl $C_{0-6}$alkyl,
(22) aryl $C_{0-6}$ alkoxycarbonyl $C_{0-6}$alkyl,
(23) hydroxycarbonyl $C_{1-6}$ alkyloxy,
(24) hydroxy $C_{0-6}$alkyl,

(25) cyano,
(26) nitro,
(27) perfluoroC$_{1-4}$alkyl,
(28) perfluoroC$_{1-4}$alkoxy,
(29) oxo,
(30) C$_{1-6}$ alkylcarbonyloxy,
(31) aryl C$_{1-6}$alkylcarbonyloxy,
(32) C$_{1-6}$ alkylcarbonylamino,
(33) aryl C$_{0-6}$ alkylcarbonylamino,
(34) C$_{1-6}$ alkylsulfonylamino,
(35) aryl C$_{0-6}$alkylsulfonylamino,
(36) C$_{1-6}$ alkoxycarbonylamino,
(37) aryl C$_{0-6}$ alkoxycarbonylamino,
(38) C$_{1-6}$alkylaminocarbonylamino,
(39) aryl C$_{0-6}$alkylaminocarbonylamino,
(40) (C$_{1-6}$alkyl)$_2$ aminocarbonylamino,
(41) (aryl C$_{0-6}$alkyl)$_2$ aminocarbonylamino,
(42) (C$_{1-6}$alkyl)$_2$ aminocarbonyloxy,
(43) (aryl C$_{0-6}$alkyl)$_2$ aminocarbonyloxy, and
(44) spiro-C$_{3-8}$cycloalkyl provided that any heteroatom substituent is bonded to a carbon atom in the heterocyclic ring;

In embodiment of the present invention, R$^3$ is selected from H, perfluoro C$_{1-8}$ alkyl, and C$_{1-8}$ alkyl, unsubstituted or substituted with one to three halogen atoms.

In class of this embodiment, R$^3$ is selected from H, perfluoro C$_{1-3}$ alkyl, and C$_{1-3}$ alkyl. In a subclass of this class, R$^3$ is selected from H, trifluoromethyl, and methyl. In a further subclass of the present invention, R$^3$ is hydrogen.

In another embodiment of the present invention, R$^2$ and R$^3$, together with the nitrogen atom to which they are attached, form a 5- to 7-membered heterocyclic ring, optionally containing one additional heteroatom selected from N, S, and O, optionally fused to a phenyl ring, optionally having one or more degrees of unsaturation, either unsubstituted or substituted with one to two substituents selected from:
(1) halogen,
(2) phenyl,
(3) C$_{1-3}$ alkyl,
(4) methoxy,
(5) hydroxy,
(6) cyano,
(7) nitro,
(8) trifluoromethyl,
(9) trifluoromethoxy, and
(10) oxo, provided that any heteroatom substituent is bonded to a carbon atom in the heterocyclic ring.

In one class of this embodiment, R$^2$ and R$^3$, together with the nitrogen atom to which they are attached, form a C$_{5-7}$ heterocyclic ring, optionally fused to a phenyl ring, unsubstituted, or substituted with one to three substituents selected from:
(1) fluoro,
(2) chloro,
(3) phenyl,
(4) methyl,
(5) methoxy,
(6) hydroxy,
(7) cyano,
(8) nitro,
(9) trifluoromethyl,
(10) trifluoromethoxy,
(11) oxo, provided that any heteroatom substituent is bonded to a carbon atom in the heterocyclic ring.

In one subclass of this embodiment, R$^2$ and R$^3$ together form a group selected from: indolinyl, tetrahydroisoquinolinyl, tetrahydroquinolinyl, piperidinyl, and pyrrolidinyl, unsubstituted or substituted with one to three substituents selected from:
(1) fluoro,
(2) chloro,
(3) phenyl,
(4) methyl,
(5) methoxy,
(6) hydroxy,
(7) cyano,
(8) nitro,
(9) trifluoromethyl,
(10) trifluoromethoxy, and
(11) oxo, provided that any heteroatom substituent is bonded to a carbon atom in the heterocyclic ring.

In one embodiment of the present invention, R$^4$ and R$^5$ are each independently selected from
(1) hydrogen,
(2) halogen,
(3) phenyl,
(4) C$_{1-6}$ alkyl,
(5) cyclopropyl
(6) cyclohexyl,
(7) C$_{5-7}$ cycloheteroalkyl,
(8) benzyl,
(9) amino,
(10) C$_{1-6}$ alkylamino,
(11) (C$_{1-6}$ alkyl)$_2$amino,
(12) aryl amino,
(13) (aryl)$_2$amino,
(14) C$_{1-6}$ alkylthio,
(15) arylthio,
(16) C$_{1-6}$ alkoxy,
(17) aryl oxy,
(18) hydroxycarbonyl,
(19) C$_{1-6}$ alkoxycarbonyl,
(20) aryl C$_{0-6}$ alkoxycarbonyl,
(21) hydroxycarbonyl C$_{1-6}$ alkyloxy,
(22) hydroxy,
(23) cyano,
(24) nitro,
(25) trifluoromethoxy,
(26) trifluoromethyl,
(27) C$_{1-6}$ alkylcarbonyloxy,
(28) aryl C$_{0-6}$alkylcarbonyloxy,
(29) alkyl C$_{1-6}$ carbonylamino,
(30) aryl C$_{0-6}$ alkylcarbonylamino,
(31) C$_{1-6}$ alkoxycarbonylamino,
(32) aryl C$_{0-6}$ alkoxycarbonylamino,
(33) C$_{1-6}$alkylaminocarbonylamino,
(34) aryl C$_{0-6}$alkylaminocarbonylamino,
(35) (C$_{1-6}$alkyl)$_2$ aminocarbonylamino,
(36) (aryl C$_{0-6}$alkyl)$_2$ aminocarbonylamino,
(37) (C$_{1-6}$alkyl)$_2$ aminocarbonyloxy,
(38) C$_{0-6}$alkylcarbonyl C$_{0-6}$alkyl, and
(39) (aryl C$_{0-6}$alkyl)$_2$ aminocarbonyloxy,
or, R$^4$ and R$^5$ together form an oxo group or =CH—R$^6$ or a spiro C$_{3-7}$ cycloalkyl ring substituted with R$^6$.

In another embodiment of the present invention, R$^4$ and R$^5$ are each independently selected from:

(1) hydrogen,
(2) fluoro,
(3) chloro,
(4) phenyl,
(5) $C_{1-3}$ alkyl,
(6) cyclopropyl
(7) benzyl,
(8) amino,
(9) $C_{1-3}$ alkoxy,
(10) phenyloxy,
(11) hydroxycarbonyl,
(12) hydroxy,
(13) cyano,
(14) nitro,
(15) trifluoromethoxy, and
(16) trifluoromethyl, or, $R^4$ and $R^5$ together form an oxo group or =CH—$R^6$ or a spiro $C_{3-7}$ cycloalkyl ring substituted with $R^6$.

In a class of this embodiment of the present invention, $R^4$ and $R^5$ are each independently selected from
(1) hydrogen,
(2) fluoro,
(3) chloro,
(4) methyl,
(5) ethyl,
(6) methoxy,
(7) hydroxy,
(8) trifluoromethoxy, and
(9) trifluoromethyl,
or $R^4$ and $R^5$ together form an oxo group.

In a subclass of this class, $R^4$ and $R^5$ are each hydrogen.

In one embodiment of the present invention $R^6$ is selected from hydrogen and methyl. In one class of this subclass, $R^6$ is hydrogen.

In embodiment of the present invention, $R^7$ is selected from hydrogen, perfluoro $C_{1-8}$ alkyl, and $C_{1-8}$ alkyl, unsubstituted or substituted with one to three fluoro or chloro substituents.

In class of this embodiment, $R^7$ is selected from hydrogen, perfluoro $C_{1-3}$ alkyl, and $C_{1-3}$ alkyl. In a subclass of this class, $R^7$ is selected from hydrogen, trifluoromethyl, and methyl. In a further subclass of the present invention, $R^7$ is hydrogen.

In one embodiment of the present invention, n is 2. In another embodiment of the present invention, n is 0. In yet another embodiment of the present invention, n is 1.

Particular compounds of structural formula (I) include:
(1) 4-methyl-17β-(2-trifluoromethylbenzamido)-4-aza-5α-androst-1-ene-3-one;
(2) 4-methyl-17β-(3-trifluoromethylbenzamido)-4-aza-5α-androst-1-ene-3-one;
(3) 4-methyl-17β-(2-methoxybenzamido)-4-aza-5α-androst-1-ene-3-one;
(4) 4-methyl-17β-(3-methoxybenzamido)-4-aza-5α-androst-1-ene-3-one;
(5) 4-methyl-17β-(4-methoxybenzamido)-4-aza-5α-androst-1-ene-3-one;
(6) 4-methyl-17β-(4-cyanobenzamido)-4-aza-5α-androst-1-ene-3-one;
(7) 4-methyl-17β-(2-chloro-pyrid-3-yl-amido)-4-aza-5α-androst-1-ene-3-one;
(8) 4-methyl-17β-(pyrid-2-yl-amido)-4-aza-5α-androst-1-ene-3-one;
(9) 4-methyl-17β-(pyrid-4-yl-amido)-4-aza-5α-androst-1-ene-3-one;
(10) 4-methyl-17β-(4-(carboxymethyl)benzamido)-4-aza-5α-androst-1-ene-3-one;
(11) 4-methyl-17β-(pyrid-3-yl-amido)-4-aza-5α-androst-1-ene-3-one;
(12) 4-methyl-17β-(2-fluorobenzamido)-4-aza-5α-androst-1-ene-3-one;
(13) 4-methyl-17β-(3-fluorobenzamido)-4-aza-5α-androst-1-ene-3-one;
(14) 4-methyl-17β-(4-fluorobenzamido)-4-aza-5α-androst-1-ene-3-one;
(15) 4-methyl-17β-(2,4-difluorobenzamido)-4-aza-5α-androst-1-ene-3-one;
(16) 4-methyl-17β-(4-chlorobutyramido)-4-aza-5α-androst-1-ene-3-one;
(17) 4-methyl-17β-(4-bromobutyramido)-4-aza-5α-androst-1-ene-3-one;
(18) Carbamic acid, [(5α,17β)-3-oxo-4-methyl-azaandrost-1-ene-17-yl]-2-bromoethyl ester;
(19) 4-methyl-17β-(2-methylpropamido)-4-aza-5α-androst-1-ene-3-one;
(20) 4-methyl-17β-(2-methoxyacetamido)-4-aza-5α-androst-1-ene-3-one;
(21) 4-methyl-17β-(cyclopropamido)-4-aza-5α-androst-1-ene-3-one;
(22) 4-methyl-17β-(acetamido)-4-aza-5α-androst-1-ene-3-one;
(23) 4-methyl-17β-(trifluoroacetamido)-4-aza-5α-androst-1-ene-3-one;
(24) 4-methyl-17β-(3,3,3-trifluoropropionamido)-4-aza-5α-androst-1-ene-3-one;
(25) 4-methyl-17β-(2-cyanoacetamido)-4-aza-5α-androst-1-ene-3-one;
(26) 4-methyl-17β-(2-methyl-2-hydroxypropamido)-4-aza-5α-androst-1-ene-3-one;
(27) 4-methyl-17β-(thiazo-4-yl-amido)-4-aza-5α-androst-1-ene-3-one;
(28) 4-methyl-17β-(pyrimid-2-yl-amido)-4-aza-5α-androst-1-ene-3-one;
(29) 4-methyl-17β-(pyrimid-4-yl-amido)-4-aza-5α-androst-1-ene-3-one;
(30) 4-methyl-17β-(oxazo-5-yl-amido)-4-aza-5α-androst-1-ene-3-one;
(31) 4-methyl-17β-(1-methyl-imidazo-2-yl-amido)-4-aza-5α-androst-1-ene-3-one;
(32) 4-methyl-17β-(furan-3-yl-amido)-4-aza-5α-androst-1-ene-3-one;
(33) 4-methyl-17β-(furan-2-yl-amido)-4-aza-5α-androst-1-ene-3-one;
(34) 4-methyl-17β-(thiophene-2-yl-amido)-4-aza-5α-androst-1-ene-3-one;
(35) 4-methyl-17β-(thiophene-3-yl-amido)-4-aza-5α-androst-1-ene-3-one;
(36) 4-methyl-17β-(pyridazin-2-yl-amido)-4-aza-5α-androst-1-ene-3-one;
(37) 4-methyl-17β-(5-methyl-pyridin-2-yl-amido)-4-aza-5α-androst-1-ene-3-one;
(38) 4-methyl-17β-(5-chloro-pyridin-2-yl-amido)-4-aza-5α-androst-1-ene-3-one;
(39) 4-methyl-17β-(quinoline-2-yl-amido)-4-aza-5α-androst-1-ene-3-one;
(40) 4-methyl-17β-(quinoline-8-yl-amido)-4-aza-5α-androst-1-ene-3-one;
(41) 4-methyl-17β-(isoquinoline-8-yl-amido)-4-aza-5α-androst-1-ene-3-one;
(42) 4-methyl-17β-(2-chlorobenzamido)-4-aza-5α-androst-1-ene-3-one;

(43) 4-methyl-17β-(3-chlorobenzamido)-4-aza-5α-androst-1-ene-3-one;
(44) 4-methyl-17β-(4-chlorobenzamido)-4-aza-5α-androst-1-ene-3-one;
(45) 4-methyl-17β-(formamido)-4-aza-5α-androst-1-ene-3-one;
(46) 4-methyl-17β-[(2-trifluoromethylphenyl)acetamido]-4-aza-5α-androst-1-ene-3-one;
(47) 4-methyl-17β-[(4-trifluoromethylphenyl)acetamido]-4-aza-5α-androst-1-ene-3-one;
(48) 4-methyl-17β-[(2-chlorophenyl)acetamido]-4-aza-5α-androst-1-ene-3-one;
(49) 4-methyl-17β-[(3-chlorophenyl)acetamido]-4-aza-5α-androst-1-ene-3-one;
(50) 4-methyl-17β-[(4-chlorophenyl)acetamido]-4-aza-5α-androst-1-ene-3-one;
(51) 4-methyl-17β-[(2,4-dichlorophenyl)acetamido]-4-aza-5α-androst-1-ene-3-one;
(52) 4-methyl-17β-[(3-fluorophenyl)acetamido]4-aza-5α-androst-1-ene-3-one;
(53) 4-methyl-17β-[(4-fluorophenyl)acetamido]-4-aza-5α-androst-1-ene-3-one;
(54) 4-methyl-17β-[(2-methoxyphenyl)acetamido]-4-aza-5α-androst-1-ene-3-one;
(55) 4-methyl-17β-[(3-methoxyphenyl)acetamido]-4-aza-5α-androst-1-ene-3-one;
(56) 4-methyl-17β-[(2,5-dimethoxyphenyl)acetamido]-4-aza-5α-androst-1-ene-3-one;
(57) 4-methyl-17β-[(3,5-difluorophenyl)acetamido]-4-aza-5α-androst-1-ene-3-one;
(58) 4-methyl-17β-[(3-nitrophenyl)acetamido]-4-aza-5α-androst-1-ene-3-one;
(59) 4-methyl-17β-(tetrahydrofuran-2-yl-amido)-4-aza-5α-androst-1-ene-3-one;
(60) 4-methyl-17β-(tetrahydrofuran-3-yl-amido)-4-aza-5α-androst-1-ene-3-one;
(61) 4-methyl-17β-(4-ethyl-pyridin-2-yl-amido)-4-aza-5α-androst-1-ene-3-one;
(62) 4-methyl-17β-(3-methyl-pyridin-2-yl-amido)4-aza-5α-androst-1-ene-3-one;
(63) 4-methyl-17β-(3-bromo-pyridin-2-yl-amido)-4-aza-5α-androst-1-ene-3-one;
(64) 4-methyl-17β-(4-bromo-pyridin-2-yl-amido)-4-aza-5α-androst-1-ene-3-one;
(65) 4-methyl-17β-[(2-phenylcyclopropyl)amido]-4-aza-5α-androst-1-ene-3-one;
(66) 4-methyl-17β-[(2-fluorophenyl)acetamido]-4-aza-5α-androst-1-ene-3-one;
(67) 4-methyl-17β-[(pyrid-2-yl)acetamido]-4-aza-5α-androst-1-ene-3-one;
(68) 4-methyl-17β-[(pyrid-3-yl)acetamido]-4-aza-5α-androst-1-ene-3-one;
(69) 4-methyl-17β-[(4-methoxyphenyl)acetamido]-4-aza-5α-androst-1-ene-3-one;
(70) 4-methyl-17β-[3-(2-fluorophenyl)propionamido]-4-aza-5α-androst-1-ene-3-one;
(71) 4-methyl-17β-[3-(4-fluorophenyl)propionamido]-4-aza-5α-androst-1-ene-3-one;
(72) 4-methyl-17β-[3-(4-rifluoromethylphenyl)propionamido]-4-aza-5α-androst-1-ene-3-one;
(73) 4-methyl-17β-[3-(2-chlorophenyl)propionamido]-4-aza-5α-androst-1-ene-3-one;
(74) 4-methyl-17β-[3-(3-chlorophenyl)propionamido]-4-aza-5α-androst-1-ene-3-one;
(75) 4-methyl-17β-[3-(4-chlorophenyl)propionamido]-4-aza-5α-androst-1-ene-3-one;
(76) 4-methyl-17β-[2-trifluoromethylcinnamido]-4-aza-5α-androst-1-ene-3-one;
(77) 4-methyl-17β-[2-chlorocinnamido]-4-aza-5α-androst-1-ene-3-one;
(78) 4-methyl-17β-[2-fluorocinnamido]-4-aza-5α-androst-1-ene-3-one;
(79) 4-methyl-17β-[4-(2,5-dichlorophenyl)butanamido]-4-aza-5α-androst-1-ene-3-one;
(80) 4-methyl-17β-[4-(2-nitrophenyl)butanamido]-4-aza-5α-androst-1-ene-3-one;
(81) 4-methyl-17β-[4-(3,4-dimethoxyphenyl)butanamido]-4-aza-5α-androst-1-ene-3-one;
(82) 4-methyl-17β-[propionamido]-4-aza-5α-androst-1-ene-3-one;
(83) 4-methyl-17β-[butyramido]-4-aza-5α-androst-1-ene-3-one;
(84) 4-methyl-17β-[(2-methyl)cyclopropamido]-4-aza-5α-androst-1-ene-3-one;
(85) Carbamic acid, [(5α,17β)-3-oxo-4-methyl-azaandrost-1-ene-17-yl]-phenyl ester;
(86) Carbamic acid, [(5α,17β)-3-oxo-4-methyl-azaandrost-1-ene-17-yl]4-chlorophenyl ester;
(87) Carbamic acid, [(5α,17β)-3-oxo-4-methyl-azaandrost-1-ene-17-yl]4-nitrophenyl ester;
(88) Carbamic acid, [(5α,17β)-3-oxo-4-methyl-azaandrost-1-ene-17-yl]-4-methylphenyl ester;
(89) Carbamic acid, [(5α,17β)-3-oxo-4-methyl-azaandrost-1-ene-17-yl]4-bromophenyl ester;
(90) Carbamic acid, [(5α,17β)-3-oxo-4-methyl-azaandrost-1-ene-17-yl]-4-fluorophenyl ester;
(91) Carbamic acid, [(5α,17β)-3-oxo-4-methyl-azaandrost-1-ene-17-yl]-4-methoxophenyl ester;
(92) Carbamic acid, [(5α,17β)-3-oxo-4-methyl-azaandrost-1-ene-17-yl]-2-nitrophenyl ester;
(93) Carbamic acid, [(5α,17β)-3-oxo-4-methyl-azaandrost-1-ene-17-yl]-3-naphthyl ester;
(94) Carbamic acid, [(5α,17β)-3-oxo-4-methyl-azaarndrost-1-ene-17-yl]-3-trifluoromethylphenyl ester;
(95) Carbamic acid, [(5α,17β)-3-oxo-4-methyl-azaandrost-1-ene-17-yl]-ethyl ester;
(96) Carbamic acid, [(5α,17β)-3-oxo-4-methyl-azaandrost-1-ene-17-yl]-benzyl ester;
(97) Carbamic acid, [(5α,17β)-3-oxo-4-methyl-azaandrost-1-ene-17-yl]-2,2,2-trifluoroethyl ester;
(98) Carbamic acid, [(5α,17β)-3-oxo-4-methyl-azaandrost-1-ene-17-yl]-2-methoxyethyl ester;
(99) Carbamic acid, [(5α,17β)-3-oxo-4-methyl-azaandrost-1-ene-17-yl]-(2,2-dimethylpropy) ester;
(100) Carbamic acid, [(5α,17β)-3-oxo-4-methyl-azaandrost-1-ene-17-yl]-2-fluoroethyl ester;
(101) Carbamic acid, [(5α,17β)-3-oxo-4-methyl-azaandrost-1-ene-17-yl]-allyl ester;
(102) Carbamic acid, [(5α,17β)-(3)-3-oxo-4-methyl-azaandrost-1-ene-17-yl]-methyl ester;
(103) Carbamic acid, [(5α,17β)-3-oxo-4-methyl-azaandrost-1-ene-17-yl]-1-propynoic ester;
(104) Carbamic acid, [(5α,17β)-3-oxo-4-methyl-azaandrost-1-ene-17-yl]-(2-methyl-2-butyl) ester;
(105) Carbamic acid, [(5α,17β)-3-oxo-4-methyl-azaandrost-1-ene-17-yl]-2-(trifluoromethyl)phenyl ester;
(106) Carbamic acid, [(5α,17β)-3-oxo-4-methyl-azaandrost-1-ene-17-yl]-4-(trifluoromethyl)phenyl ester;
(107) Carbamic acid, [(5α,17β)-3-oxo-4-methyl-azaandrost-1-ene-17-yl]-2-fluorophenyl ester;
(108) Carbamic acid, [(5α,17β)-3-oxo-4-methyl-azaandrost-1-ene-17-yl]-3-fluorophenyl ester;

(109) Carbamic acid, [(5α,17β)-3-oxo-4methyl-azaandrost-1-ene-17-yl]-(2-hydroxy-1-ethyl) ester;
(110) Carbamic acid, [(5α,17β)-3-oxo-4-methyl-azaandrost-1-ene-17-yl]-2-methoxyphenyl ester;
(111) Carbamic acid, [(5α,17β)-3-oxo-4-methyl-azaandrost-1-ene-17-yl]-3-methoxyphenyl ester;
(112) Carbamic acid, [(5α,17β)-3-oxo-4-methyl-azaandrost-1-ene-17-yl]-2-ethoxyphenyl ester;
(113) Carbamic acid, [(5α,17α)-3-oxo-4-methyl-azaandrost-1-ene-17-yl]-3-ethoxyphenyl ester;
(114) Carbamic acid, [(5α,17β)-3-oxo-4-methyl-azaandrost-1-ene-17-yl]-4-ethoxyphenyl ester;
(115) Carbamic acid, [(5α,17β)-3-oxo-4-methyl-azaandrost-1-ene-17-yl]-4-chlorophenyl ester;
(116) Carbamic acid, [(5α,17β)-3-oxo-4-methyl-azaandrost-1-ene-17-yl]-3-chlorophenyl ester;
(117) Carbamic acid, [(5α,17β)-3-oxo-4-methyl-azaandrost-1-ene-17-yl]-3-(trifluoromethoxy)phenyl ester;
(118) Carbamic acid, [(5α,17β)-3-oxo-4-methyl-azaandrost-1-ene-17-yl]-4-(trifluoromethoxy)phenyl ester;
(119) Carbamic acid, [(5α,17β)-3-oxo-4-methyl-azaandrost-1-ene-17-yl]-2-propyl ester;
(120) Carbamic acid, [(5α,17β)-3-oxo-4-methyl-azaandrost-1-ene-17-yl]-1-propyl ester;
(121) Carbamic acid, [(5α,17β)-3-oxo-4-methyl-azaandrost-1-ene-17-yl]-1-butyl ester;
(122) Carbamic acid, [(5α,17β)-3-oxo-4-methyl-azaandrost-1-ene-17-yl]-1-hexyl ester;
(123) 4-methyl-17β-(phenylsulfonamido)-4-aza-5α-androst-1-ene-3-one;
(124) 4-methyl-17β-(2-trifluoromethylphenylsulfonamido)-4-aza-5α-androst-1-ene-3-one;
(125) 4-methyl-17β-(3-trifluoromethylphenylsulfonamido)-4-aza-5α-androst-1-ene-3-one;
(126) 4-methyl-17β-(2-chlorophenylsulfonamido)-4-aza-5α-androst-1-ene-3-one;
(127) 4-methyl-17β-(3-chlorophenylsulfonamido)-4-aza-5α-androst-1-ene-3-one;
(128) 4-methyl-17β-(2-trifluoromethoxyphenylsulfonamido)-4-aza-5α-androst-1-ene-3-one;
(129) 4-methyl-17β-(2-cyanophenylsulfonamido)-4-aza-5α-androst-1-ene-3-one;
(130) 4-methyl-17β-(4-methoxyphenylsulfonamido)-4-aza-5α-androst-1-ene-3-one;
(131) 4-methyl-17β-(3-bromo-5-methoxyphenylsulfonamido)-4-aza-5α-androst-1-ene-3-one;
(132) 4-methyl-17β-(8-quinolylsulfonamido)-4-aza-5α-androst-1-ene-3-one;
(133) 4-methyl-17β-(3-cyanophenylsulfonamido)-4-aza-5α-androst-1-ene-3-one;
(134) 4-methyl-17β-(4-chlorophenylsulfonamido)-4-aza-5α-androst-1-ene-3-one;
(135) 4-methyl-17β-[(2-methylsufonyl)phenyl]sulfonamido)-4-aza-5α-androst-1-ene-3-one;
(136) N-[(5α,17β)-4-methyl-3-oxo-4-azaandrost-1-en-17-yl]-N'-phenyl urea;
(137) N-[(5α,17β)-4-methyl-3-oxo-4-azaandrost-1-en-17-yl]-N'-(2-trifluoromethyl)phenyl urea;
(138) N-[(5α,17β)-4-methyl-3-oxo-4-azaandrost-1-en-17-yl]-N'-(3-trifluoromethyl)phenyl urea;
(139) N-[(5α,17β)-4-methyl-3-oxo-4-azaandrost-1-en-17-yl]-N'-3-chlorophenyl urea;
(140) N-[(5α,17β)-4-methyl-3-oxo-4-azaandrost-1-en-17-yl]-N'-(4-chloro-2-trifluoromethylphenyl)urea;
(141) N-[(5αa,17β)-4-methyl-3-oxo-4-azaandrost-1-en-17-yl]-N'-3-acetylphenyl urea;
(142) N-[(5α,17β)-4-methyl-3-oxo-4-azaandrost-1-en-17-yl]-N'-(5-chloro-2-trifluoromethylphenyl)urea;
(143) N-[(5α,17β)-4-methyl-3-oxo-4-azaandrost-1-en-17-yl]-N'-(2,4-[bistrifluoromethyl]phenyl)urea;
(144) N-[(5α,17β)-4-methyl-3-oxo-4-azaandrost-1-en-17-yl]-N'-(3,4-difluorophenyl)urea;
(145) N-[(5α,17β)-4-methyl-3-oxo-4-azaandrost-1-en-17-yl]-N'-(2,3-dichlorophenyl)urea;
(146) N-[(5α,17β)-4-methyl-3-oxo-4-azaandrost-1-en-17-yl]-N'-(2,4-dichlorophenyl)urea;
(147) N-[(5α,17β)-4-methyl-3-oxo-4-azaandrost-1-en-17-yl]-N'-(3,4-dichlorophenyl)urea;
(148) N-[(5α,17β)-4-methyl-3-oxo-4-azaandrost-1-en-17-yl]-N'-2-chlorophenyl)urea;
(149) N-[(5α,17β)-4-methyl-3-oxo-4-azaandrost-1-en-17-yl]-N'-(2-chloro-5-trifluoromethylphenyl)urea;
(150) N-[(5α,17β)-4-methyl-3-oxo-4-azaandrost-1-en-17-yl]-N'-(4-chloro-3-trifluoromethylphenyl)urea;
(151) N-[(5α,17β)-4-methyl-3-oxo-4-azaandrost-1-en-17-yl]-N'-(4-trifluoromethyl)phenyl urea;
(152) N-[(5α,17β)-4-methyl-3-oxo-4-azaandrost-1-en-17-yl]-N'-(2,3-dimethylpheny)urea;
(153) N-[(5α,17β)-4-methyl-3-oxo-4-azaandrost-1-en-17-yl]-N'-methyl urea;
(154) N-[(5α,17β)-4-methyl-3-oxo-4-azaandrost-1-en-17-yl]-N'-ethyl urea;
(155) N-[(5α,17β)-4-methyl-3-oxo-4-azaandrost-1-en-17-yl]-N'-dimethyl urea;
(156) N-[(5α,17β)-4-methyl-3-oxo-4-azaandrost-1-en-17-yl]-N'-diethyl urea;
(157) N-[(5α,17β)-4-methyl-3-oxo-4-azaandrost-1-en-17-yl] urea;

The term "alkyl" shall mean straight or branched chain alkanes of one to ten total carbon atoms, or any number within this range (i.e., methyl, ethyl, 1-propyl, 2-propyl, n-butyl, s-butyl, t-butyl, etc.). The term "$C_0$ alkyl" (as in "$C_{0-8}$ alkylaryl") shall refer to the absence of an alkyl group.

The term "alkenyl" shall mean straight or branched chain alkenes of two to ten total carbon atoms, or any number within this range.

The term "alkynyl" shall mean straight or branched chain alkynes of two to ten total carbon atoms, or any number within this range.

The term "cycloalkyl" shall mean cyclic rings of alkanes of three to eight total carbon atoms, or any number within this range (i.e., cyclopropyl, cyclobutyl, cyclopentyl, cyclohexyl, cycloheptyl or cyclooctyl).

The term "cycloheteroalkyl," as used herein, shall mean a 3- to 8-membered fully saturated heterocyclic ring containing one or two heteroatoms chosen from N, O, or S and optionally fused to another fully saturated ring. Examples of cycloheteroalkyl groups include, but are not limited to piperidinyl, pyrrolidinyl, azetidinyl, morpholinyl, piperazinyl, tetrahydrofuranyl, and octahydroquinolizinyl. In one embodiment of the present invention cycloheteroalkyl is selected from piperidinyl, pyrrolidinyl, tetrahydrofuranyl, and morpholinyl.

The term "alkoxy," as used herein, refers to straight or branched chain alkoxides of the number of carbon atoms specified (e.g., $C_{1-5}$ alkoxy), or any number within this range (i.e., methoxy, ethoxy, etc.).

The term "aryl," as used herein, refers to a monocyclic or bicyclic system comprising at least one aromatic ring, wherein the monocylic or bicyclic system contains 0, 1, 2, 3, or 4 heteroatoms chosen from N, O, or S, and wherein the monocylic or bicyclic system is either unsubstituted or substituted with one or more groups independently selected from hydrogen, halogen, aryl, $C_{1-8}$ alkyl, $C_{3-8}$ cycloalkyl, $C_{3-8}$ cycloheteroalkyl, aryl $C_{1-6}$alkyl, amino $C_{0-6}$alkyl, $C_{1-6}$ alkylamino $C_{0-6}$alkyl, $(C_{1-6}$ alkyl$)_2$amino $C_{0-6}$alkyl, aryl $C_{0-6}$ alkylamino $C_{0-6}$alkyl, (aryl $C_{0-6}$ alkyl$)_2$amino $C_{0-6}$alkyl, $C_{1-6}$ alkylthio, aryl $C_{0-6}$alkylthio, $C_{1-6}$ alkylsulfinyl, aryl $C_{0-6}$alkylsulfinyl, $C_{1-6}$ alkylsulfonyl, aryl $C_{0-6}$alkylsulfonyl, $C_{1-6}$ alkoxy $C_{0-6}$alkyl, aryl $C_{0-6}$ alkoxy $C_{0-6}$alkyl, hydroxycarbonyl $C_{0-6}$alkyl, $C_{1-6}$ alkoxycarbonyl $C_{0-6}$alkyl, aryl $C_{0-6}$ alkoxycarbonyl $C_{0-6}$alkyl, hydroxycarbonyl $C_{1-6}$ alkyloxy, hydroxy $C_{0-6}$alkyl, cyano, nitro, perfluoro$C_{1-4}$alkyl, perfluoro$C_{1-4}$alkoxy, oxo, $C_{1-6}$ alkylcarbonyloxy, aryl $C_{0-6}$alkylcarbonyloxy, $C_{1-6}$ alkylcarbonylamino, aryl $C_{0-6}$ alkylcarbonylamino, $C_{1-6}$ alkylsulfonylamino, aryl $C_{0-6}$alkylsulfonylamino, $C_{1-6}$ alkoxycarbonylamino, aryl $C_{0-6}$ alkoxycarbonylamino, $C_{1-6}$alkylaminocarbonylamino, aryl $C_{0-6}$alkylaminocarbonylamino, $(C_{1-6}$alkyl$)_2$ aminocarbonylamino, (aryl $C_{0-6}$ alkyl$)_2$ aminocarbonylamino, $(C_{1-6}$alkyl$)_2$ aminocarbonyloxy, (aryl $C_{0-6}$alkyl$)_2$ aminocarbonyloxy, and $C_{0-6}$alkylcarbonyl $C_{0-6}$ alkyl. Examples of aryl include, but are not limited to, phenyl, naphthyl, pyridyl, pyrrolyl, pyrazolyl, pyrazinyl, pyrimidinyl, imidazolyl, benzimidazolyl, benzthiazolyl, benzoxazolyl, indolyl, thiophenyl, furanyl, dihydrobenzofuranyl, benzo(1,3)dioxolanyl, benzo(1,4)dioxanyl, oxazolyl, isoxazolyl, thiazolyl, quinolinyl, isothiazolyl, indanyl, isoquinolinyl, dihydroisoquinolinyl, tetrahydronaphthyridinyl, benzothienyl, imidazopyridinyl, tetrahydrobenzazepinyl, quinoxalinyl, imidazopyrimidinyl, cyclopentenopyridinyl, phthalazinyl, tetrahydroquinolinyl, oxindolyl, isoquinolinyl, imidazothiazolyl, dihydroimidazothiazolyl, tetrazolyl, triazolyl, pyridazinyl, piperidinyl, piperazinyl, oxadiazolyl, thiadiazolyl, triazinyl, indazolyl, indazolinone, dihydrobenzofuranyl, phthalide, phthalimide, coumarin, chromone, tetrahydroisoquindine, naphthyridinyl, tetrahydronaphthyridinyl, isoindolinyl, triazanaphthalinyl, pteridinyl, and purinyl, which are either unsubstituted or substituted with one or more groups independently selected from hydrogen, halogen, aryl, $C_{1-8}$ alkyl, $C_{3-8}$ cycloalkyl, $C_{3-8}$ cycloheteroalkyl, aryl $C_{1-6}$alkyl, amino $C_{0-6}$alkyl, $C_{1-6}$ alkylamino $C_{0-6}$alkyl, $(C_{1-6}$ alkyl$)_2$amino $C_{0-6}$alkyl, aryl $C_{0-6}$ alkylamino $C_{0-6}$alkyl, (aryl $C_{0-6}$ alkyl$)_2$amino $C_{0-6}$alkyl, $C_{1-6}$ alkylthio, aryl $C_{0-6}$alkylthio, $C_{1-6}$ alkylsulfinyl, aryl $C_{0-6}$alkylsulfinyl, $C_{1-6}$ alkylsulfonyl, aryl $C_{0-6}$alkylsulfonyl, $C_{1-6}$ alkoxy $C_{0-6}$alkyl, aryl $C_{0-6}$ alkoxy $C_{0-6}$alkyl, hydroxycarbonyl $C_{0-6}$alkyl, $C_{1-6}$ alkoxycarbonyl $C_{0-6}$alkyl, aryl $C_{0-6}$ alkoxycarbonyl $C_{0-6}$alkyl, hydroxycarbonyl $C_{1-6}$ alkyloxy, hydroxy $C_{0-6}$alkyl, cyano, nitro, perfluoro$C_{1-4}$alkyl, perfluoro$C_{1-4}$alkoxy, oxo, $C_{1-6}$ alkylcarbonyloxy, aryl $C_{0-6}$alkylcarbonyloxy, $C_{1-6}$ alkylcarbonylamino, aryl $C_{0-6}$ alkylcarbonylamino, $C_{1-6}$ alkylsulfonylamino, aryl $C_{0-6}$alkylsulfonylamino, $C_{1-6}$ alkoxycarbonylamino, aryl $C_{0-6}$ alkoxycarbonylamino, $C_{1-6}$alkylaminocarbonylamino, aryl $C_{0-6}$alkylaminocarbonylamino, $(C_{1-6}$alkyl$)_2$ aminocarbonylamino, (aryl $C_{0-6}$ alkyl$)_2$ aminocarbonylamino, $(C_{1-6}$alkyl$)_2$ aminocarbonyloxy, (aryl $C_{0-6}$alkyl$)_2$ aminocarbonyloxy, and $C_{0-6}$alkylcarbonyl $C_{0-6}$alkyl. In one embodiment of the present invention, aryl is selected from phenyl, pyridyl, pyrazolyl, benzamidazolyl, imidazolyl, furanyl, napthyl, indolyl, indanyl, thiophenyl, pyrazinyl, benzothienyl, 3,4dihydro-1(1H)-isoquinolinyl, 1-8-tetrahydronaphthyridinyl, imidazo[1,2-a]pyridinyl, 2-oxo-2,3,4,5-tetrahydro-1H-benzo[B]azepinyl, quinoxalinyl, imidazo[1,2-a]pyrimidinyl, 2-3-cyclopentenopyridinyl, 1-(2H)-phthalazinyl, 1,2,3,4-tetrahydroquinolinyl, oxindolyl, isoquinolinyl, imidazo[2,1-b][1,3]thiazolyl, 2,3-dihydroimidazo[2,1-b][1,3]thiazolyl, and quinolinyl. Preferably, the aryl group is unsubstituted, mono-, di-, or tri-substituted with one to three of the above-named substituents; more preferably, the aryl group is unsubstituted, mono- or di-substituted with one to two of the above-named substituents.

Whenever the term "alkyl" or "aryl" or either of their prefix roots appears in a name of a substituent (e.g., aryl $C_{0-8}$ alkyl), it shall be interpreted as including those limitations given above for "alkyl" and "aryl." Designated numbers of carbon atoms (e.g., $C_{0-8}$) shall refer independently to the number of carbon atoms in an alkyl or cyclic alkyl moiety or to the alkyl portion of a larger substituent in which alkyl appears as its prefix root.

The terms "arylalkyl" and "alkylaryl" include an alkyl portion where alkyl is as defined above and to include an aryl portion where aryl is as defined above. Examples of arylalkyl include, but are not limited to, benzyl, fluorobenzyl, chlorobenzyl, phenylethyl, phenylpropyl, fluorophenylethyl, chlorophenylethyl, methyl, thiophenylethyl, and thiophenylpropyl. Examples of alkylaryl include, but are not limited to, toluene, ethylbenzene, propylbenzene, methylpyridine, ethylpyridine, propylpyridine and butylpyridine.

The term "halogen" shall include iodine, bromine, chlorine, and fluorine.

The term "oxy" means an oxygen (O) atom. The term "thio" means a sulfur (S) atom. The term "oxo" means "=O". The term "carbonyl" means "C=O."

The term "substituted" shall be deemed to include multiple degrees of substitution by a named substituent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

When any variable (e.g., $R^3$, $R^4$, etc.) occurs more than one time in any constituent or in formula I, its definition on each occurrence is independent of its definition at every other occurrence. Also, combinations of substituents and/or variables are permissible only if such combinations result in stable compounds.

Under standard nomenclature used throughout this disclosure, the terminal portion of the designated side chain is described first, followed by the adjacent functionality toward the point of attachment. For example, a $C_{1-5}$ alkylcarbonylamino $C_{1-6}$ alkyl substituent is equivalent to

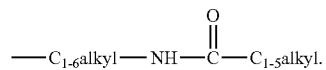

In choosing compounds of the present invention, one of ordinary skill in the art will recognize that the various substituents, i.e. $R^1$, $R^2$, $R^3$, etc., are to be chosen in conformity with well-known principles of chemical structure connectivity.

The term "substituted" shall be deemed to include multiple degrees of substitution by a named substituent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

Representative compounds of the present invention typically display submicromolar affinity for the androgen receptor. Compounds of this invention are therefore useful in treating mammals suffering from disorders related to androgen receptor function. Pharmacologically effective amounts of the compound, including the pharmaceutically effective salts thereof, are administered to the mammal, to treat disorders related to androgen receptor function, or which can be improved by the addition of additional androgen, such as osteoporosis, osteopenia, glucocorticoid-induced osteoporosis, periodontal disease, HIV-wasting, cancer cachexia, bone fracture, bone damage following bone reconstructive surgery, muscular dystrophies, sarcopenia, frailty, aging skin, male hypogonadism, post-menopausal symptoms in women, female sexual dysfunction, premature ovarian failure, autoimmune disease, atherosclerosis, hypercholesterolemia, hyperlipidemia, aplastic anemia and other hematopoietic disorders, pancreatic cancer, renal cancer, arthritis and joint repair. Still further, the compounds of the present invention are useful in treating insulin resistance, including NIDDM, obesity and growth retardation associated with obesity, hyperinsulinemia, as well as Metabolic Syndrome, or "Syndrome X" as defined in Johannsson, J. Clin Endocrin. Metabl 82: 727-34 (1997).

It is generally preferable to administer compounds of the present invention as enantiomerically pure formulations. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

As used herein, a compound that binds to an intracellular receptor, such as the androgen receptor, and mimics the effect of the natural ligand is referred to as an "agonist"; whereas, a compound that inhibits the effect of the natural ligand is called an "antagonist." The term "tissue selective androgen receptor modulator" refers to to an androgen receptor ligand that mimics the action of the natural ligand in some tissues but not in others.

Compounds according to the present invention may be prepared according to the procedures outlined in Scheme A and as detailed in the Examples.

SCHEME A

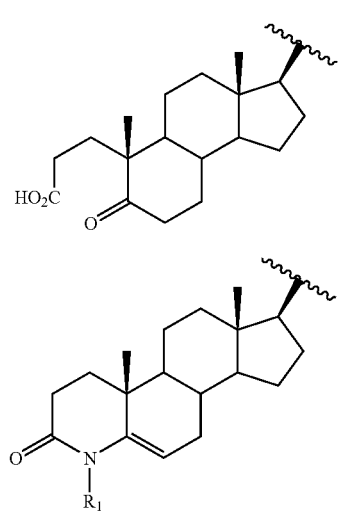

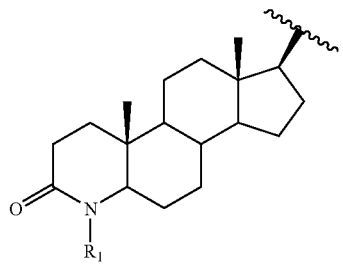

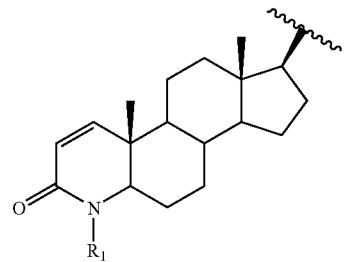

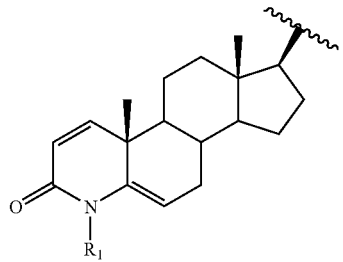

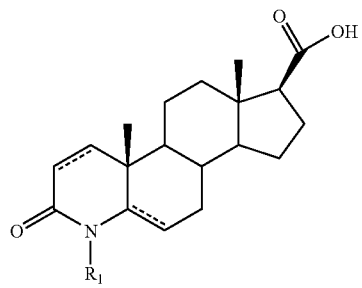

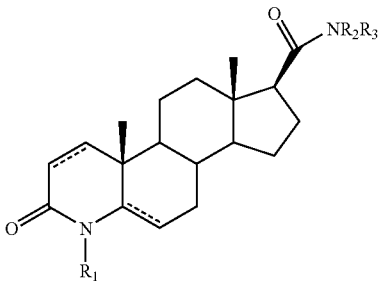

Following procedures described by Rasmusson et al. (J. Med. Chem., 1986, 29, 2298-2315), the keto-acid II may be reacted with an amine in a solvent such as ethylene glycol at elevated temperature to produce compounds of structure III. When ammonia is used as the amine the product is an unsubstituted lactam. In this case (III, $R^1$=H), the nitrogen may then be alkylated by treatment of the lactam with a base such as sodium hydride in an aprotic solvent (e.g. tetrahydrofuran, "THF") followed by reaction with an appropriate electrophile. 4-Azasteroids of structure IV may be obtained by reduction of the 5,6-double bond of III using hydrogen gas and a catalyst such as palladium on carbon in an organic solvent. Such solvents include ethyl acetate, ethanol and methanol. Alternatively, the 5,6-double bond may be saturated using a reducing agent such as sodium cyanoborohydride in the presence of an acid, for example trifluoroacetic acid, in a suitable organic solvent. A second route to compounds of structure IV involves the catalytic reduction of the 1,2-double bond of V.

The preparation of 4-azasteroids of general structure V involves the dehydrogenation of compound IV. Methods to achieve this are described in U.S. Pat. No. 5,302,621. Similarly, the introduction of a 1,2-double bond into III will yield the 1,2 and 5,6-unsaturated 4-aza steroids VI. Such methods include dehydrogenation using 2,3-dichloro-5,6-dicyano-p-benzoquinone in the presence of a silylating agent. A second method requires the treatment of IV (or III) with benzeneseleninic anhydride in an inert solvent at elevated temperature. Alternatively, reaction of IV (or III) with a base such as diisopropyl lithium amide followed by treatment with a diaryl sulfide allows the introduction of a 2-arylthioether. This 2-arylthioether may then be oxidized (e.g. with a peracid) to produce a sulfoxide which is then eliminated to yield V (or VI). 4-Unsubstituted 4-azasteroids (III-VI) can be alkylated on nitrogen to produce 4-substituted 4-azasteroids. This transformation can be accomplished using a base such as sodium hydride in an aprotic solvent (e.g., THF) followed by reaction with an electrophile such as an alkylbromide or alkyliodide.

Formation of the C-17 amide bond to give VIII is readily achieved from the corresponding acid VII by activation of the acid and then reaction with the required amine (U.S. Pat. No. 5,302,621). Methods used to activate the acid include treatment with 1,2-dichloroethane "EDC" and 1-hydroxybenzotriazole "HOBT" (or 1-hydroxy-7-azabenzotriazole "HOAT") in a solvent such as dimethylformamide "DMF". A second method involves the formation of a thiopyridylester followed by displacement with an amine which may be aided by the presence of silver salts (e.g. silver triflate). A third method requires the formation of the acid chloride from the acid. A fourth method involves the use of carbonyldiimidazole to generate the imidazolide intermediate (U.S. Pat. No. 5,237,061). Reaction of this with a substituted amino magnesium regent then generates the desired C-17 amide. Additionally, it is possible to form a mixed anhydride and then use this to generate the amide by methods readily appreciated by one of ordinary skill in the art.

The term "pharmaceutically acceptable salt" is intended to include all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or pro-drug formulations.

The term "therapeutically effective amount" means the amount the compound of structural formula I that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts.

By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

The administration of the compound of structural formula I in order to practice the present methods of therapy is carried out by administering an effective amount of the compound of structural formula I to the patient in need of such treatment or prophylaxis. The need for a prophylactic administration according to the methods of the present invention is determined via the use of well known risk factors. The effective amount of an individual compound is determined, in the final analysis, by the physician in charge of the case, but depends on factors such as the exact disease to be treated, the severity of the disease and other diseases or conditions from which the patient suffers, the chosen route of administration other drugs and treatments which the patient may concomitantly require, and other factors in the physician's judgment.

Generally, the daily dosage of the compound of structural formula I may be varied over a wide range from 0.01 to 1000 mg per adult human per day. Most preferably, dosages range from 0.1 to 200 mg/day. For oral administration, the compositions are preferably provided in the form of tablets containing 0.01 to 1000 mg, particularly 0.01, 0.05, 0.1, 0.5, 1.0, 2.5, 3.0, 5.0, 6.0, 10.0, 15.0, 25.0, 50.0, 75, 100, 125, 150, 175, 180, 200, 225, and 500 milligrams of the active ingredient for the symptomatic adjustment of the dosage to the patient to be treated.

The dose may be administered in a single daily dose or the total daily dosage may be administered in divided doses of two, three or four times daily. Furthermore, based on the properties of the individual compound selected for administration, the dose may be administered less frequently, e.g., weekly, twice weekly, monthly, etc. The unit dosage will, of course, be correspondingly larger for the less frequent administration.

When administered via intranasal routes, transdermal routes, by rectal or vaginal suppositories, or through a continual intravenous solution, the dosage administration will, of course, be continuous rather than intermittent throughout the dosage regimen.

Exemplifying the invention is a pharmaceutical composition comprising any of the compounds described above and a pharmaceutically acceptable carrier. Also exemplifying the invention is a pharmaceutical composition made by combining any of the compounds described above and a pharmaceutically acceptable carrier. An illustration of the invention is a process for making a pharmaceutical composition comprising combining any of the compounds described above and a pharmaceutically acceptable carrier.

Formulations of the tissue selective androgen receptor modulator employed in the present method for medical use comprise the compound of structural formula I together with an acceptable carrier thereof and optionally other therapeutically active ingredients. The carrier must be pharmaceutically acceptable in the sense of being compatible with the other ingredients of the formulation and not deleterious to the recipient subject of the formulation.

The present invention, therefore, further provides a pharmaceutical formulation comprising the compound of structural formula I together with a pharmaceutically acceptable carrier thereof.

The formulations include those suitable for oral, rectal, intravaginal, topical or parenteral (including subcutaneous, intramuscular and intravenous administration). Preferred are those suitable for oral administration.

The formulations may be presented in a unit dosage form and may be prepared by any of the methods known in the art of pharmacy. All methods include the step of bringing the active compound in association with a carrier which constitutes one or more ingredients. In general, the formulations are prepared by uniformly and intimately bringing the active compound in association with a liquid carrier, a waxy solid carrier or a finely divided solid carrier, and then, if needed, shaping the product into desired dosage form.

Formulations of the present invention suitable for oral administration may be presented as discrete units such as capsules, cachets, tablets or lozenges, each containing a predetermined amount of the active compound; as a powder or granules; or a suspension or solution in an aqueous liquid or non-aqueous liquid, e.g., a syrup, an elixir, or an emulsion.

A tablet may be made by compression or molding, optionally with one or more accessory ingredients. Compressed tablets may be prepared by compressing in a suitable machine the active compound in a free flowing form, e.g., a powder or granules, optionally mixed with accessory ingredients, e.g., binders, lubricants, inert diluents, disintegrating agents or coloring agents. Molded tablets may be made by molding in a suitable machine a mixture of the active compound, preferably in powdered form, with a suitable carrier. Suitable binders include, without limitation, starch, gelatin, natural sugars such as glucose or beta-lactose, corn sweeteners, natural and synthetic gums such as acacia, tragacanth or sodium alginate, carboxymethyl-cellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

Oral liquid forms, such as syrups or suspensions in suitably flavored suspending or dispersing agents such as the synthetic and natural gums, for example, tragacanth, acacia, methyl cellulose and the like may be made by adding the active compound to the solution or suspension. Additional dispersing agents which may be employed include glycerin and the like.

Formulations for vaginal or rectal administration may be presented as a suppository with a conventional carrier, i.e., a base that is nontoxic and nonirritating to, mucous membranes, compatible with the compound of structural formula I, and is stable in storage and does not bind or interfere with the release of the compound of structural formula I. Suitable bases include: cocoa butter (theobroma oil), polyethylene glycols (such as carbowax and polyglycols), glycol-surfactant combinations, polyoxyl 40 stearate, polyoxyethylene sorbitan fatty acid esters (such as Tween, Myrj, and Arlacel), glycerinated gelatin, and hydrogenated vegetable oils. When glycerinated gelatin suppositories are used, a preservative such as methylparaben or propylparaben may be employed.

Topical preparations containing the active drug component can be admixed with a variety of carrier materials well known in the art, such as, e.g., alcohols, aloe vera gel, allantoin, glycerine, vitamin A and E oils, mineral oil, PPG2 myristyl propionate, and the like, to form, e.g., alcoholic solutions, topical cleansers, cleansing creams, skin gels, skin lotions, and shampoos in cream or gel formulations.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinyl-pyrrolidone, pyran copolymer, polyhydroxypropylmethacrylamide-phenol, polyhydroxy-ethylaspartamidephenol, or polyethylene-oxide polylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Formulations suitable for parenteral administration include formulations that comprise a sterile aqueous preparation of the active compound which is preferably isotonic with the blood of the recipient. Such formulations suitably comprise a solution or suspension of a compound that is isotonic with the blood of the recipient subject. Such formulations may contain distilled water, 5% dextrose in distilled water or saline and the active compound. Often it is useful to employ a pharmaceutically and pharmacologically acceptable acid addition salt of the active compound that has appropriate solubility for the solvents employed. Useful salts include the hydrochloride isothionate and methanesulfonate salts. Useful formulations also comprise concentrated solutions or solids comprising the active compound which on dilution with an appropriate solvent give a solution suitable for parenteral administration.

The compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

The pharmaceutical composition and method of the present invention may further comprise other therapeutically active compounds usually applied in the treatment of the above mentioned conditions, including: osteoporosis, osteopenia, glucocorticoid-induced osteoporosis, periodontal disease, HIV-wasting, cancer cachexia, bone fracture, bone damage following bone reconstructive surgery, muscular dystrophies, sarcopenia, frailty, aging skin, male hypogonadism, post-menopausal symptoms in women, female sexual dysfunction, premature ovarian failure, autoimmune disease, atherosclerosis, hypercholesterolemia, hyperlipidemia, aplastic anemia and other hematopoietic disorders, pancreatic cancer, renal cancer, arthritis and joint repair. Still further, the pharmaceutical composition and method of the present invention may further comprise other therapeutically active compounds usually applied in the treatment of insulin resistance, including NIDDM, obesity and growth retardation associated with obesity, hyperinsulinemia, as well as Metabolic Syndrome, or "Syndrome X" as defined in Johannsson, J. Clin Endocrin. Metabl 82: 727-34 (1997).

For the treatment and prevention of osteoporosis, the compounds of the present invention may be administered in combination with a bone-strengthening agent selected from: resorption inhibitors, osteoanabolic agents, and other agents beneficial for the skeleton through the mechanisms which are not precisely defined, such as calcium supplements, flavenoids and vitamin D analogues. For example, the compounds of the instant invention may be effectively administered in combination with effective amounts of other agents such as estrogens, bisphosphonates, SERMs, cathepsin K inhibitors, osteoclast integrin inhibitors, vacuolar proton pump inhibitors, VEGF, thiazolidinediones, calcitonin, protein kinase inhibitors, parathyroid hormone and derivatives, calcium receptor antagonists, growth hormone secretagogues, growth hormone releasing hormone, insulin-like growth factor, bone morphogenic protein (BMP), inhibitors of BMP antagonism, prostaglandin derivatives, fibroblast growth factors, vitamin D and derivatives thereof, Vitamin K and derivatives thereof, soy isoflavones, calcium, and fluoride salts. The conditions of periodontal disease, bone fracture, bone damage following bone reconstructive surgery may also benefit from these combined treatments.

In the treatment of osteoporosis, the activity of the compounds of the present invention are distinct from that of the resorption inhibitors: estrogens, bisphosphonates, SERMs, calcitonin and cathepsin K inhibitors, vacuolar proton pump inhibitors, agents interfering with the RANK/RANKL/Osteoprotegerin pathway, p38 inhibitors or any other inhibitors of osteoclast generation or osteoclast activation Rather than inhibiting bone resorption, the compounds of structural formula I stimulate bone formation, acting preferentially on cortical bone, which is responsible for a significant part of bone strength. The thickening of cortical bone substantially contributes to a reduction in fracture risk, especially fractures of the hip. The combination of the tissue selective androgen receptor modulators of structural formula I with resorption inhibitors such as estrogen, bisphosphonates, antiestrogens, SERMs, calcitonin, osteoclast integrin inhibitors HMG-CoA reductase inhibitors, proton pump inhibitors, and cathepsin K inhibitors is particularly useful because of the complementarity of the bone anabolic and antiresorptive actions.

Bone antiresportive agents are those agents which are known in the art to inhibit the resorption of bone and include, for example, estrogen and estrogen derivatives which include steroidal compounds having estrogenic activity such as, for example, 17β-estradiol, estrone, conjugated estrogen (PREMARIN®), equine estrogen, 17β-ethynyl estradiol, and the like. The estrogen or estrogen derivative may be employed alone or in combination with a progestin or progestin derivative. Nonlimiting examples of progestin derivatives are norethindrone and medroxy-progesterone acetate.

Bisphosphonates are also bone anti-resorptive agents. Bisphosphonate compounds may also be employed in combination with the compound of structural formula I of the present invention include:
4-amino-1-hydroxybutylidene-1,1-bisphosphonic acid,
N-methyl-4-amino-hydroxybutylidene-1,1-bisphosphonic acid,
4-(N,N-dimethylamino-1-hydroxybutylidene-1,1-bisphosphonic acid,
3-amino-1-hydroxypropylidene-1,1-bisphosphonic acid,
3-(N,N-dimethylamino)-1-hydroxypropylidene-1,1-bisphosphonic acid,
1-hydroxy-3-(N-methyl-N-pentylamino)propylidene-1,1-bisphosphonic acid,
1-hydroxy-2-(3-pyridyl)ethylidene-1,1-bisphosphonic acid,
4-(hydroxymethylene-1,1-bisphosphonic acid)piperidine,
(1-hydroxyethylidene)-bisphosphonate,
(dichloromethylene)-bisphosphonate,
[1-hydroxy-2-imidazopyridin-(1,2-a)-3-ylethylidene]bisphosphonate,
(6-amino-1-hydroxyheylidene)bisphosphonate,
[1-hydroxy-2-(1H-imidazole-1-yl)ethylidene]bisphosphonate;

and their pharmaceutically acceptable salts. Especially preferred is alendronate, 4-amino-1-hydroxybutylidene-1,1-bisphosphonic acid monosodium salt, trihydrate. Methods for the preparation of bisphosphonic acids may be found in, e.g., U.S. Pat. No. 3,251,907; U.S. Pat. No. 3,422,137; U.S. Pat. No. 3,584,125; U.S. Pat. No. 3,940,436; U.S. Pat. No. 3,944,599; U.S. Pat. No. 3,962,432; U.S. Pat. No. 4,054,598; U.S. Pat. No. 4,267,108; U.S. Pat. No. 4,327,039; U.S. Pat. No. 4,407,761; U.S. Pat. No. 4,578,376; U.S. Pat. No. 4,621,077; U.S. Pat. No. 4,624,947; U.S. Pat. No. 4,746,654; U.S. Pat. No. 4,761,406; U.S. Pat. No. 4,922,077. In particular, methods for the preparation of 4-amino-1-hydroxybutylidene-1,1-bisphosphonic acid monosodium salt trihydrate may be found in U.S. Pat. No. 4,407,761 and U.S. Pat. No. 4,621,077.

Still further, antiestrogenic compounds such as raloxifene (see, e.g., U.S. Pat. No. 5,393,763) clomiphene, zuclomiphene, enclomiphene, nafoxidene, CI-680, CI-628, CN-55, 945-27, Mer-25, U-11, 555A, U-100A, and salts thereof, and the like (see, e.g., U.S. Pat. Nos. 4,729,999 and 4,894,373) may be employed in combination with the compound of structural formula I in the methods and compositions of the present invention. These agents are also known as SERMs, or selective estrogen receptor modulators, agents known in the art to prevent bone loss by inhibiting bone resorption via pathways believed to be similar to those of estrogens. These agents may beneficially be used in combination with the compounds of the present invention to beneficially treat bone disorders including osteoporosis. Such agents include, for example: tamoxifen, raloxifene, lasofoxifene, toremifene, azorxifene, EM-800, EM-652, TSE 424, clomiphene, droloxifene, idoxifene and levormeloxifene. (Goldstein, et al., A pharmacological review of selective oestrogen receptor modulators. Human Reproduction Update, 6: 212-224, 2000, and Lufkin, et al., The role of selective estrogen receptor modulators in the prevention and treatment of Osteoporosis. Rheumatic Disease Clinics of North America. 27 (1): 163-185, 2001.)

Osteoclast integrin inhibitors, also called vitronectin inhibitors and αvβ3antagonists, suppress bone resorption and may be employed in combination with the tissue selective androgen receptor modulators of structural formula I for the treatment of bone disorders including osteoporosis. Peptidyl as well as peptidomimetic antagonists of the αvβ3 integrin receptor have been described both in the scientific and patent literature. For example, reference is made to W. J. Hoekstra and B. L. Poulter, Curr. Med. Chem. 5: 195-204, 1998 and references cited therein; WO 95/32710; WO 95/37655; WO 97/01540; WO 97/37655; WO 98/08840; WO 98/18460; WO 98/18461; WO 98/25892; WO 98/31359; WO 98/30542; WO 99/15506; WO 99/15507; WO 00/03973; EP 853084; EP 854140; EP 854145; U.S.

Pat. Nos. 5,204,350; 5,217,994; 5,639,754; 5,741,796; 5,780,426; 5,929,120; 5,952,341; 6,017,925; and 6,048,861. Evidence of the ability of αvβ3 integrin receptor antagonists to prevent bone resorption in vitro and in vivo has been presented (V. W. Engleman, et al., "A Peptidomimetic Antagonist of the αvβ3 Integrin Inhibits Bone Resorption In Vitro and Prevents Osteoporosis In Vivo," J. Clin. Invest. 99: 2284-2292, 1997; S. B. Rodan, et al., "A High Affinity Non-Peptide αvβ3 Ligand Inhibits Osteoclast Activity In Vitro and In Vivo," J. Bone Miner. Res. 11: S289, 1996; J. F. Gourvest, et al., "Prevention of OVX-Induced Bone Loss With a Non-peptidic Ligand of the αvβ3 Vitronectin Receptor," Bone 23: S612, 1998; M. W. Lark, et al., "An Orally Active Vitronectin Receptor αvβ3 Antagonist Prevents Bone Resorption In Vitro and In Vivo in the Ovariectomized Rat," Bone 23: S219, 1998). Other αvβ3 antagonists are described in R. M. Keenan, et al., "Discovery of Potent Nonpeptide Vitronectin Receptor (αvβ3) Antagonists," J. Med. Chem. 40: 2289-2292, 1997; R. M. Keenan, et al., "Benzimidazole Derivatives As Arginine Mimetics in 1,4-Benzodiazepine Nonpeptide Vitronectin Receptor (αvβ3) Antagonists," Bioorg. Med. Chem. Lett. 8: 3165-3170, 1998; and R. M. Keenan, et al., "Discovery of an Imidazopyridine-Containing 1,4-Benzodiazepine Nonpeptide Vitronectin Receptor (αvβ3) Antagonist With Efficacy in a Restenosis Model," Bioorg. Med. Chem. Lett. 8: 3171-3176, 1998. Still other benzazepine, benzodiazepine and benzocycloheptene αvβ3 integrin receptor antagonists are described in the following patent publications: WO 96/00574, WO 96/00730, WO 96/06087, WO 96/26190, WO 97/24119, WO 97/24122, WO 97/24124, WO 98/14192, WO 98/15278, WO 99/05107, WO 99/06049, WO 99/15170, WO 99/15178, WO 99/15506, and U.S. Pat. No. 6,159,964, and WO 97/34865. αvβ3 integrin receptor antagonists having dibenzocycloheptene, dibenzocycloheptane and dibenzoxazepine scaffolds have been described in WO 97/01540, WO 98/30542, WO 99/11626, WO 99/15508, WO 00/33838, U.S. Pat. Nos. 6,008,213, and 6,069,158. Other osteoclast integrin receptor antagonists incorporating backbone conformational ring constraints have been described in the patent literature. Published patent applications or issued patents disclosing antagonists having a phenyl constraint include WO 98/00395, WO 99/32457, WO 99/37621, WO 99/44994, WO 99/45927, WO 99/52872, WO 99/52879, WO 99/52896, WO 00/06169, EP 0 820,988, EP 0 820,991, U.S. Pat. Nos. 5,741,796; 5,773,644; 5,773,646; 5,843,906; 5,852,210; 5,929,120; 5,952,381; 6,028,223; and 6,040,311. Published patent applications or issued patents disclosing antagonists having a monocyclic ring constraint include WO 99/26945, WO 99/30709, WO 99/30713, WO 99/31099, WO 99/59992, WO 00/00486, WO 00/09503, EP 0 796,855, EP 0 928,790, EP 0 928,793, U.S. Pat. Nos. 5,710,159; 5,723,480; 5,981,546; 6,017,926; and 6,066,648. Published patent applications or issued patents disclosing antagonists having a bicyclic ring constraint include WO 98/23608, WO 98/35949, WO 99/33798, EP 0 853,084, U.S. Pat. Nos. 5,760,028; 5,919,792; and 5,925,655. Reference is also made to the following reviews for additional scientific and patent literature that concern alpha v integrin antagonists: M. E. Duggan, et al., "Ligands to the integrin receptor αvβ3," Exp. Opin. Ther. Patents, 10: 1367-1383, 2000; M. Gowen, et al., "Emerging therapies for osteoporosis," Emerging Drugs, 5: 1-43, 2000; J. S. Kerr, et al., "Small molecule αv integrin antagonists: novel anticancer agents," Exp. Opin. Invest. Drugs, 9: 1271-1291, 2000; and W. H. Miller, et al., "Identification and in vivo efficacy of small-molecule antagonists of integrin αvβ3 (the vitronectin receptor)," Drug Discovery Today, 5: 397-408, 2000.

Cathepsin K, formerly known as cathepsin O2, is a cysteine protease and is described in PCT International Application Publication No. WO 96/13523, published May 9, 1996; U.S. Pat. No. 5,501,969, issued Mar. 3, 1996; and U.S. Pat. No. 5,736,357, issued Apr. 7, 1998, all of which are incorporated by reference herein in their entirety. Cysteine proteases, specifically cathepsins, are linked to a number of disease conditions, such as tumor metastasis, inflammation, arthritis, and bone remodeling. At acidic pH's, cathepsins can degrade type-I collagen. Cathepsin protease inhibitors can inhibit osteoclastic bone resorption by inhibiting the degradation of collagen fibers and are thus useful in the treatment of bone resorption diseases, such as osteoporosis.

Members of the class of HMG-CoA reductase inhibitors, known as the "statins," have been found to trigger the growth of new bone, replacing bone mass lost as a result of osteoporosis (*The Wall Street Journal*, Friday, Dec. 3, 1999, page B1). Therefore, the statins hold promise for the treatment of bone resorption. Examples of HMG-CoA reductase inhibitors include statins in their lactonized or dihydroxy open acid forms and pharmaceutically acceptable salts and esters thereof, including but not limited to lovastatin (see U.S. Pat. No. 4,342,767); simvastatin (see U.S. Pat. No. 4,444,784); dihydroxy open-acid simvastatin, particularly the ammonium or calcium salts thereof; pravastatin, particularly the sodium salt thereof (see U.S. Pat. No. 4,346,227); fluvastatin particularly the sodium salt thereof (see U.S. Pat. No. 5,354,772); atorvastatin, particularly the calcium salt thereof (see U.S. Pat. No. 5,273,995); cerivastatin, particularly the sodium salt thereof (see U.S. Pat. No. 5,177,080), rosuvastatin, also known as ZD4522 (see U.S. Pat. No. 5,260,440) and pitavastatin also referred to as NK-104 or nisvastatin (see PCT international publication number WO 97/23200).

Osteoclast vacuolar ATPase inhibitors, also called proton pump inhibitors, may also be employed together with the tissue selective androgen receptor modulator of structural formula I. The proton ATPase which is found on the apical membrane of the osteoclast has been reported to play a significant role in the bone resorption process. Therefore, this proton pump represents an attractive target for the design of inhibitors of bone resorption which are potentially useful for the treatment and prevention of osteoporosis and related metabolic diseases (C. Farina, et al., "Selective inhibitors of the osteoclast vacuolar proton ATPase as novel bone resorption inhibitors," DDT, 4: 163-172, 1999).

The angiogenic factor VEGF has been shown to stimulate the bone-resorbing activity of isolated mature rabbit osteoclasts via binding to its receptors on osteoclasts (M. Nakagawa, et al., "Vascular endothelial growth factor (VEGF) directly enhances osteoclastic bone resorption and survival of mature osteoclasts," *FEBS Letters*, 473: 161-164, 2000). Therefore, the development of antagonists of VEGF binding to osteoclast receptors, such as KDR/Flk-1 and Flt-1, may provide yet a further approach to the treatment or prevention of bone resorption.

Activators of the peroxisome proliferator-activated receptor-γ (PPARγ), such as the thiazolidinediones (TZD's), inhibit osteoclast-like cell formation and bone resorption in vitro. Results reported by R. Okazaki, et al. in *Endocrinology*, 140, pp 5060-5065, 1999 point to a local mechanism on bone marrow cells as well as a systemic one on glucose metabolism. Nonlimiting examples of PPARγ activators include troglitazone, pioglitazone, rosiglitazone, and BRL 49653.

Calcitonin may also be employed together with the tissue selective androgen receptor modulator of structural formula I. Calcitonin is preferentially administered as nasal spray. Azra, et al., Calcitonin, 1996, In: J. P. Bilezikian, et al. Ed. Principles of Bone Biology, San Diego: Academic Press; and Silverman. Calcitonin,. Rheumatic Disease Clinics of North America 27:187-196, 2001).

Protein kinase inhibitors may also be employed together with the tissue selective androgen receptor modulator of structural formula I. Kinase inhibitors include those disclosed in WO 0117562 and are in one embodiment selected from inhibitors of P-38. Specific embodiments of P-38 inhibitors useful in the present invention include: SB 203580 (Badger, et al., Pharmacological profile of SB 203580, a selective inhibitor of cytokine suppressive binding protein/p38 kinase, in animal models of arthritis, bone resorption, endotoxin shock and immune function, J. Pharmacol. Exp. Ther. 279: 1453-1461, 1996).

Osteoanabolic agents are those agents that are known in the art to build bone by increasing the production of the bone matrix. Such osteoanabolic agents include, for example, the various forms of parathyroid hormone (PTH) such as naturally occurring PTH (1-84), PTH (1-34), analogs thereof, native or with substitutions and particularly parathyroid hormone subcutaneous injection. PTH has been found to increase the activity of osteoblasts, the cells that form bone, thereby promoting the synthesis of new bone (*Modern Drug Discovery*, Vol. 3, No. 8, 2000). In studies reported at the First World Congress on Osteoporosis held in Chicago in June 2000, women in combined PTH-estrogen therapy exhibited a 12.8% increase in spinal bone mass and a 4.4% increase in total hip mass. Another study presented at the same meeting showed that PTH could increase bone size as well as density. A clinical trial of the effect of the human parathyroid hormone 1-34 fragment [hPTH(1-34)] on post-menopausal osteoporotic women resulted in ≧65% reduction in spine fractures and a 54% reduction in nonvertebral fractures, after a median of 22 months of treatment (J. M. Hock, *Bone,* 27: 467-469, 2000 and S. Mohan, et al., *Bone,* 27: 471-478, 2000, and references cited therein). Thus, PTH and fragments thereof, such as hPTH(1-34), may prove to be efficacious in the treatment of osteoporosis alone or in combination with other agents, such as the tissue selective androgen receptor modulators of the present invention.

Also useful in combination with the SARMs of the present invention are calcium receptor antagonists which induce the secretion of PTH as described by Gowen, et al., in Antagonizing the parathyroid calcium receptor stimulates parathyroid hormone secretion and bone formation in osteopenic rats, J Clin Invest. 105 :1595-604, 2000.

Growth hormone secretagogues, growth hormone, growth hormone releasing hormone and insulin-like growth factor and the like are also osteoanabolic agents which may be employed with the compounds according to structural formula I for the treatment of osteoporosis. Representative growth hormone secretagogues are disclosed in U.S. Pat. No. 3,239,345; U.S. Pat. No. 4,036,979; U.S. Pat. No. 4,411,890; U.S. Pat. No. 5,206,235; U.S. Pat. No. 5,283,241; U.S. Pat. No. 5,284,841; U.S. Pat. No. 5,310,737; U.S. Pat. No. 5,317,017; U.S. Pat. No. 5,374,721; U.S. Pat. No. 5,430,144; U.S. Pat. No. 5,434,261; U.S. Pat. No. 5,438,136; U.S. Pat. No. 5,494,919; U.S. Pat. No. 5,494,920; U.S. Pat. No. 5,492,916; U.S. Pat. No. 5,536,716; EPO Patent Pub. No. 0,144,230; EPO Patent Pub. No. 0,513,974; PCT Patent Pub. No. WO 94/07486; PCT Patent Pub. No. WO 94/08583; PCT Patent Pub. No. WO 94/11012; PCT Patent Pub. No. WO 94/13696; PCT Patent Pub. No. WO 94/19367; PCT Patent Pub. No. WO 95/03289; PCT Patent Pub. No. WO 95/03290; PCT Patent Pub. No. WO 95/09633; PCT Patent Pub. No. WO 95/11029; PCT Patent Pub. No. WO 95/12598; PCT Patent Pub. No. WO 95/13069; PCT Patent Pub. No. WO 95/14666; PCT Patent Pub. No. WO 95/16675; PCT Patent Pub. No. WO 95/16692; PCT Patent Pub. No. WO 95/17422; PCT Patent Pub. No. WO 95/17423; PCT Patent Pub. No. WO 95/34311; PCT Patent Pub. No. WO 96/02530; *Science* 260, 1640-1643, Jun. 11, 1993; *Ann. Rep. Med. Chem.,* 28, 177-186 (1993); *Bioorg. Med. Chem. Ltrs.,* 4(22), 2709-2714, 1994; and *Proc. Natl. Acad. Sci. USA* 92, 7001-7005, July 1995.

Insulin-like growth factor (IGF) may also be employed together with the tissue selective androgen receptor modulator of structural formula I. Insulin-like growth factors may be selected from Insulin-like Growth Factor I, alone or in combination with IGF binding protein 3 and IGF II. (Johannson and Rosen, The IGFs as potential therapy for metabolic bone diseases, 1996, In: Bilezikian, et. al. Ed. Principles of Bone Biology. San Diego: Academic Press; and Ghiron, et al., Effects of recombinant insulin-like growth factor-I and growth hormone on bone turnover in elderly women, J Bone Miner Res. 10:1844-52, 1995).

Bone morphogenic protein (BMP) may also be employed together with the tissue selective androgen receptor modulator of structural formula I. Bone morphogenic protein includes BMP 2, 3, 5, 6, 7, as well as related molecules TGF beta and GDF 5. Rosen, et al., Bone morphogenetic proteins. 1996. In: J. P. Bilezikian, et. al. Ed. Principles of Bone Biology, San Diego: Academic Press; and Wang E A, Bone morphogenetic proteins (BMPs): therapeutic potential in healing bony defects. Trends Biotechnol. 11:379-83, 1993.

Inhibitors of BMP antagonism may also be employed together with the tissue selective androgen receptor modulator of structural formula I. BMP antagonist inhibitors are in one embodiment selected from inhibitors of the BMP antagonists SOST, noggin, chordin, gremlin, and dan (Massague and Chen Controlling TGF-beta signaling, Genes Dev. 14:627-44, 2000; Aspenberg, et al., The bone morphogenetic proteins antagonist Noggin inhibits membranous ossification, J Bone Miner Res. 16:497-500, 2001; Brunkow, et al., Bone dysplasia sclerostenosis results from loss of the SOST gene product, a novel cystine knot-containing protein, Am J Hum Genet. 68: 577-89, 2001).

Prostaglandin derivatives may also be employed together with the tissue selective androgen receptor modulator of structural formula I. Prostaglandin derivatives are in one embodiment selected from agonists of prostaglandin receptor EP1, EP2, EP4, FP and IP or a derivative thereof. Pilbeam, et al., Prostaglandins and bone metabolism, 1996, In: Bilezikian, et al. Ed. Principles of Bone Biology. San Diego: Academic Press; Weinreb, et al., Expression of the prostaglandin E(2) (PGE(2)) receptor subtype EP(4) and its regulation by PGE(2) in osteoblastic cell lines and adult rat bone tissue(1), Bone. 28(3):275-81, 2001.

Fibroblast growth factors may also be employed together with the tissue selective androgen receptor modulator of structural formula I. Fibroblast growth factors include aFGF, bFGF and related peptides with FGF activity. Hurley Florkiewicz; Fibroblast growth factor and vascular endothelial growth factor families. 1996. In: J. P. Bilezikian, et. al. Ed. Principles of Bone Biology. San Diego: Academic Press.

In addition to bone resorption inhibitors and osteoanabolic agents, there are also other agents known to be beneficial for the skeleton through the mechanisms which are not precisely defined. These agents may also be favorably combined with the tissue selective androgen receptor modulator of structural formula I.

Vitamin D and Vitamin D derivatives may also be employed together with the tissue selective androgen receptor modulator of structural formula I. Vitamin D and Vitamin D derivatives include: natural vitamin D, 25-OH-vitamin D3, 1α,25(OH)2 vitamin D3, 1α-OH-vitamin D3, 1α-OH-vitamin D2, dihydrotachysterol, 26,27-F6-1α,25(OH)2 vitamin D3, 19-nor-1α,25(OH)2 vitamin D3, 22-oxacalcitriol, calcipotriol, 1α,25(OH)2-16-ene-23-yne-vitamin D3 (Ro 23-7553), EB1089, 20-epi-1α,25(OH)2 vitamin D3, KH1060, ED71, 1α,24(S)—(OH)2 vitamin D3, 1α,24(R)—(OH)2 vitamin D3. Jones G. Pharmacological mechanisms of therapeutics: vitamin D and analogs. 1996. In: J. P. Bilezikian, et. al. Ed. Principles of Bone Biology. San Diego: Academic Press.

Vitamin K and Vitamin K derivatives may also be employed together with the tissue selective androgen receptor modulator of structural formula I. Vitamin K and Vitamin K derivatives include: menatetrenone (vitamin K2). Shiraki, et al., Vitamin K2 (menatetrenone) effectively prevents fractures and sustains lumbar bone mineral density in osteoporosis, J Bone Miner Res. 15: 515-21.

Soy isoflavones including ipriflavone may be employed together with the tissue selective androgen receptor modulator of structural formula I.

Fluoride salts, including sodium fluoride (NaF) or monosodium fluorophosphate (WFP) may also be employed together with the tissue selective androgen receptor modulator of structural formula I. Dietary calcium supplements may also be employed together with the tissue selective androgen receptor modulator of structural formula I. Dietary calcium supplements include calcium carbonate, calcium citrate and natural calcium salts. Heaney, Calcium, 1996, In: J. P. Bilezikian, et. al. Ed. Principles of Bone Biology. San Diego: Academic Press.

Daily dosage ranges for bone resorption inhibitors, osteoanabolic agents and other agents which may be used to benefit the skeleton when used in combination with the compounds of structural formula I are those which are known in the art. In such combinations, generally the daily dosage range for the tissue selective androgen receptor modulator of structural formula I is 0.01 to 1000 mg per adult human per day, more preferably from 0.1 to 200 mg/day. However, adjustments to decrease the dose of each agent may be made due to the increased efficacy of the combined agent.

In particular, when a bisphosphonate is employed, dosages of 2.5 to 100 mg/day (measured as the free bisphosphonic acid) are appropriate for treatment, more preferably 5 to 20 mg/day, especially about 10 mg/day. Prophylactically, doses of about 2.5 to about 10 mg/day and especially about 5 mg/day should be employed. For reduction in side-effects, it may be desirable to administer the combination of the compound of structural formula I and the bisphosphonate once a week. For once weekly administration, doses of about 15 mg to 700 mg per week of bisphosphonate and 0.07 to 7000 mg of the compound of structural formula I may be employed, either separately, or in a combined dosage form. The compound of structural formula I may be favorably administered in a controlled-release delivery device, particularly for once weekly administration.

For the treatment of atherosclerosis, hypercholesterolemia, hyperlipidemia, the compounds of structural formula I may be effectively administered in combination with one or more additional active agents. The additional active agent or agents can be lipid altering compounds such as HMG-CoA reductase inhibitors, or agents having other pharmaceutical activities, or agents that have both lipid-altering effects and other pharmaceutical activities. Examples of HMG-CoA reductase inhibitors include statins in their lactonized or dihydroxy open acid forms and pharmaceutically acceptable salts and esters thereof, including but not limited to lovastatin (see U.S. Pat. No. 4,342,767); simvastatin (see U.S. Pat. No. 4,444,784); dihydroxy open-acid simvastatin, particularly the ammonium or calcium salts thereof; pravastatin, particularly the sodium salt thereof (see U.S. Pat. No. 4,346,227); fluvastatin particularly the sodium salt thereof (see U.S. Pat. No. 5,354,772); atorvastatin, particularly the calcium salt thereof (see U.S. Pat. No. 5,273,995); cerivastatin, particularly the sodium salt thereof (see U.S. Pat. No. 5,177,080), and nisvastatin also referred to as NK-104 (see PCT international publication number WO 97/23200). Additional active agents which may be employed in combination with a compound of structural formula I include, but are not limited to, HMG-CoA synthase inhibitors; squalene epoxidase inhibitors; squalene synthetase inhibitors (also known as squalene synthase inhibitors), acyl-coenzyme A: cholesterol acyltransferase (ACAT) inhibitors including selective inhibitors of ACAT-1 or ACAT-2 as well as dual inhibitors of ACAT1 and -2; microsomal triglyceride transfer protein (MTP) inhibitors; probucol; niacin; cholesterol absorption inhibitors such as SCH-58235 also known as ezetimibe and 1-(4-fluorophenyl)-3(R)-[3(S)-(4-fluorophenyl)-3-hydroxypropyl)]-4(S)-(4-hydroxyphenyl)-2-azetidinone, which is described in U.S. Pat. Nos. 5,767,115 and 5,846,966; bile acid sequestrants; LDL (low density lipoprotein) receptor inducers; platelet aggregation inhibitors, for example glycoprotein IIb/IIIa fibrinogen receptor antagonists and aspirin; human peroxisome proliferator activated receptor gamma (PPARγ) agonists including the compounds commonly referred to as glitazones for example troglitazone, pioglitazone and rosiglitazone and, including those compounds included within the structural class known as thiazolidinediones as well as those PPARγ agonists outside the thiazolidinedione structural class; PPARα agonists such as clofibrate, fenofibrate including micronized fenofibrate, and gemfibrozil; PPAR dual α/γ agonists; vitamin $B_6$ (also known as pyridoxine) and the pharmaceutically acceptable salts thereof such as the HCl salt; vitamin $B_{12}$ (also known as cyanocobalamin); folic acid or a pharmaceutically acceptable salt or ester thereof such as the sodium salt and the methylglucamine salt; anti-oxidant vitamins such as vitamin C and E and beta carotene; beta-blockers; angiotensin II antagonists such as losartan; angiotensin converting enzyme inhibitors such as enalapril and captopril; calcium channel blockers such as nifedipine and diltiazam; endothelian antagonists; agents such as LXR ligands that enhance ABC1 gene expression; bisphosphonate compounds such as alendronate sodium; and cyclooxygenase-2 inhibitors such as rofecoxib and celecoxib as well as other agents known to be useful in the treatment of these conditions.

Daily dosage ranges for HMG-CoA reductase inhibitors when used in combination with the compounds of structural formula I correspond to those which are known in the art. Similarly, daily dosage ranges for the HMG-CoA synthase inhibitors; squalene epoxidase inhibitors; squalene synthetase inhibitors (also known as squalene synthase inhibitors), acyl-coenzyme A: cholesterol acyltransferase (ACAT) inhibitors including selective inhibitors of ACAT-1 or ACAT-2 as well as dual inhibitors of ACAT1 and -2; microsomal triglyceride transfer protein (MTP) inhibitors; probucol; niacin; cholesterol absorption inhibitors including ezetimibe; bile acid sequestrants; LDL (low density lipoprotein) receptor inducers; platelet aggregation inhibitors, including glycoprotein IIb/IIIa fibrinogen receptor antagonists and aspirin; human peroxisome proliferator activated receptor gamma (PPARγ) agonists; PPARα agonists; PPAR dual α/γ agonists; vitamin $B_6$; vitamin $B_{12}$; folic acid; anti-oxidant vitamins; beta-blockers; angiotensin II antagonists; angiotensin converting enzyme inhibitors; calcium channel blockers; endothelian antagonists; agents such as LXR ligands that enhance ABC1 gene expression; bisphosphonate compounds; and cyclooxygenase-2 inhibitors also correspond to those which are known in the art, although due to the combined action with the compounds of structural formula I, the dosage may be somewhat lower when administered in combination.

In accordance with the method of the present invention, the individual components of the combination can be administered separately at different times during the course of therapy or concurrently in divided or single combination forms. The instant invention is therefore to be understood as embracing all such regimes of simultaneous or alternating treatment and the term "administering" is to be interpreted accordingly. It will be understood that the scope of combinations of the compounds of this invention with other agents useful for treating diseases caused by androgen deficiency or that can be ameliorated by addition of androgen.

The following examples are provided to further illustrate details for the preparation and use of the compounds of the present invention. The examples are not intended to be limitations on the scope of the instant invention in any way, and they should not be so construed. Furthermore, the compounds described in the following examples are not to be construed as forming the only genus that is considered as the invention, and any combination of the compounds or their moieties may itself form a genus. Those skilled in the art will readily understand that known variations of the conditions and processes of the following preparative procedures can be used to prepare these compounds. All temperatures are in degrees Celsius unless noted otherwise.

Abbreviations: Ac represents acetyl; AR is the androgen receptor; cPr is cyclopropyl; ddWater is distilled, deionized water; DMEM is Dulbecco's Modified Eagle Media; DMF is dimethyl formamide; EDTA is ethylenediaminetetraacetic acid; EGTA is ethylene bis(oxyethylenenitrolo)tetraacetic acid; Et represents ethyl; FCS is fetal calf serum; HAP is hydroxylapatite; hAR is the human androgen receptor; iPr is isopropyl; Me is methyl; MEM is Minimum Essential Media; min. is minute; NMM is N-methyl morpholine; PBS is phosphate buffered saline (8 g NaCl, 0.2 g KCl, 1.44 g Na$_2$HPO$_4$, 0.24 KH$_2$PO$_4$ dissolve into H$_2$O to make 1 L and adjust pH to 7.4 with HCl); Ph is phenyl; pQCT is peripheral quantitative computer tomography; R1881 is methyltrienolone, an androgen receptor agonist; RhAR is the rhesus androgen receptor; SARM is a tissue selective androgen receptor modulator; SEAP is secreted alkaline phosphatase; TAC is triamcinolone acetonide; THF is tetrahydrofuran.

EXAMPLE 1

Preparation of 4-methyl-17β-(2-trifluoromethylbenzamido)-4-aza-5α-androst-1-ene-3one (1-3)

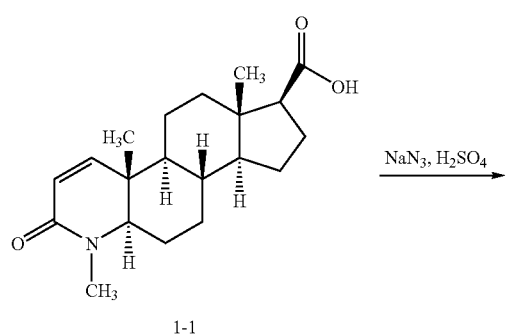

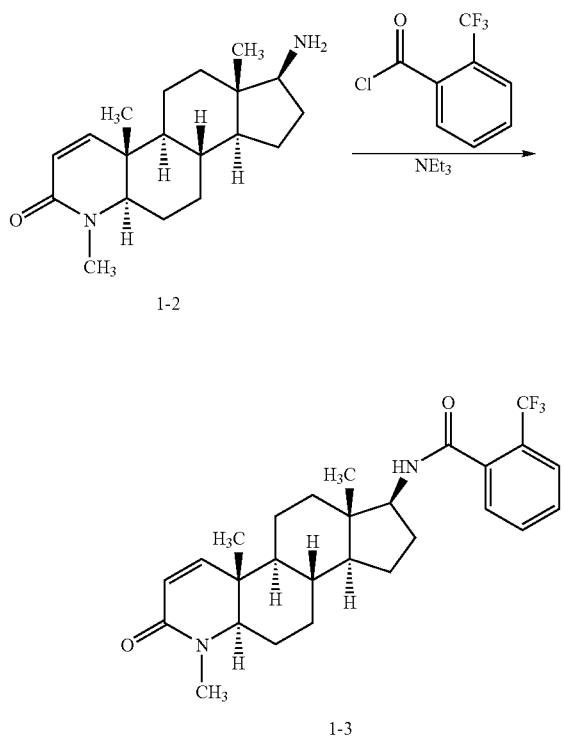

4-methyl-17β-amino-4-aza-5α-androst-1-ene-3-one (1-2).

Acid 1-1 (7.6 g, 22.9 mmol; prepared as described in WO 93/23420), CHCl$_3$ (72 mL) and H$_2$SO$_4$ (36 mL) was heated to 52° C. Sodium azide (3.1 g, 48.4 mmol) was added in three portions over 15 minutes. After the last addition, the mixture was heated to 60° C. for 30 minutes. The mixture was then allowed to cool to ambient temperature and poured into 200 g of ice. To this mixture was then added 200 mL of CHCl$_3$ and then 50% w/w NaOH until the aqueous pH=12. The organic portion was separated. The aqueous portion was extracted with CHCl$_3$ (2×200 mL). The combined organic portions were washed with 1/4 5 M NaOH/brine (70 mL), dried (MgSO$_4$) and then concentrated to provide the amine 1-2 as a white solid.

HRMS (FAB, M+1) found 303.2437.

4-methyl-17β-(2-trifluoromethylbenzamido)-4-aza-5α-androst-1-ene-3-one (1-3).

Amine 1-2 (250 mg, 0.828 mmol), NEt$_3$ (250 μL, 1.6 mmol), 2-trifluoromethylbenzoyl chloride (173 mg) and CH$_2$Cl$_2$ (1 mL) were combined and then stirred overnight. The reaction was diluted with 1 mL CH$_2$Cl$_2$ and then washed with saturated aqueous K$_2$CO$_3$. The organic portion was separated and purified by flash chromatography (silica, hexanes→EtOAc) provided compound 1-3 as a white solid.

HRMS (FAB, M+1) found 475.2597

Utilizing the same general procedure as described for compound 1-3 in Example 1, and by varying the acid chloride reagent, compounds 1-4 through 1-86 were prepared (Table 1); mass spectral characterization of these compounds is listed in Table 2.

TABLE 1
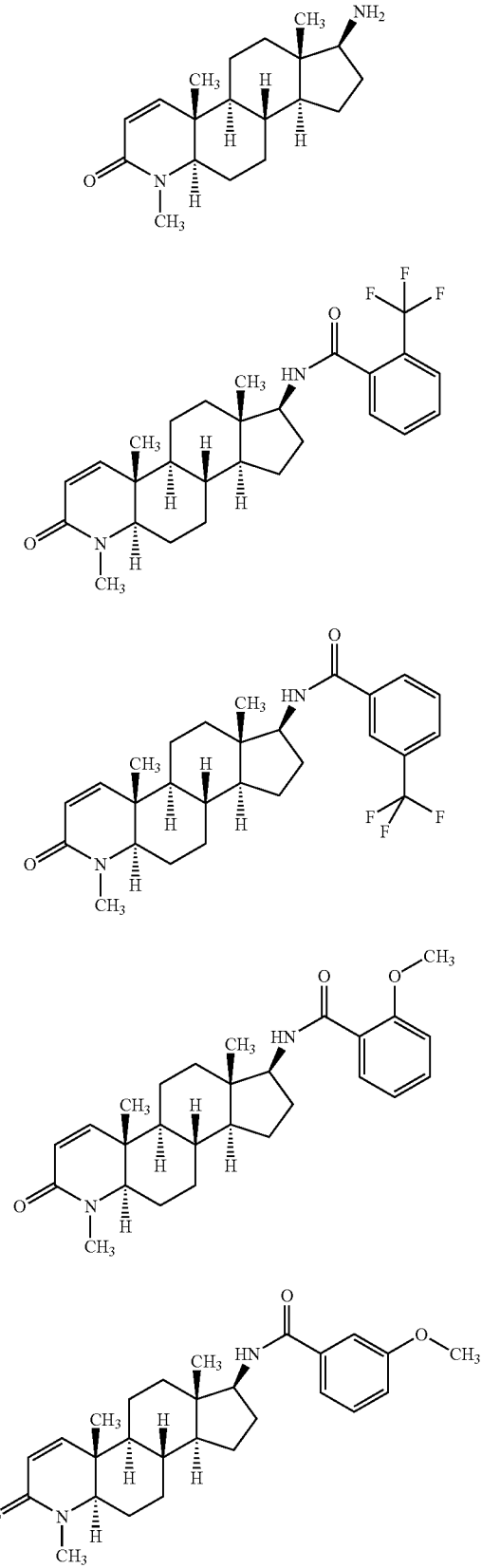
TABLE 1-continued
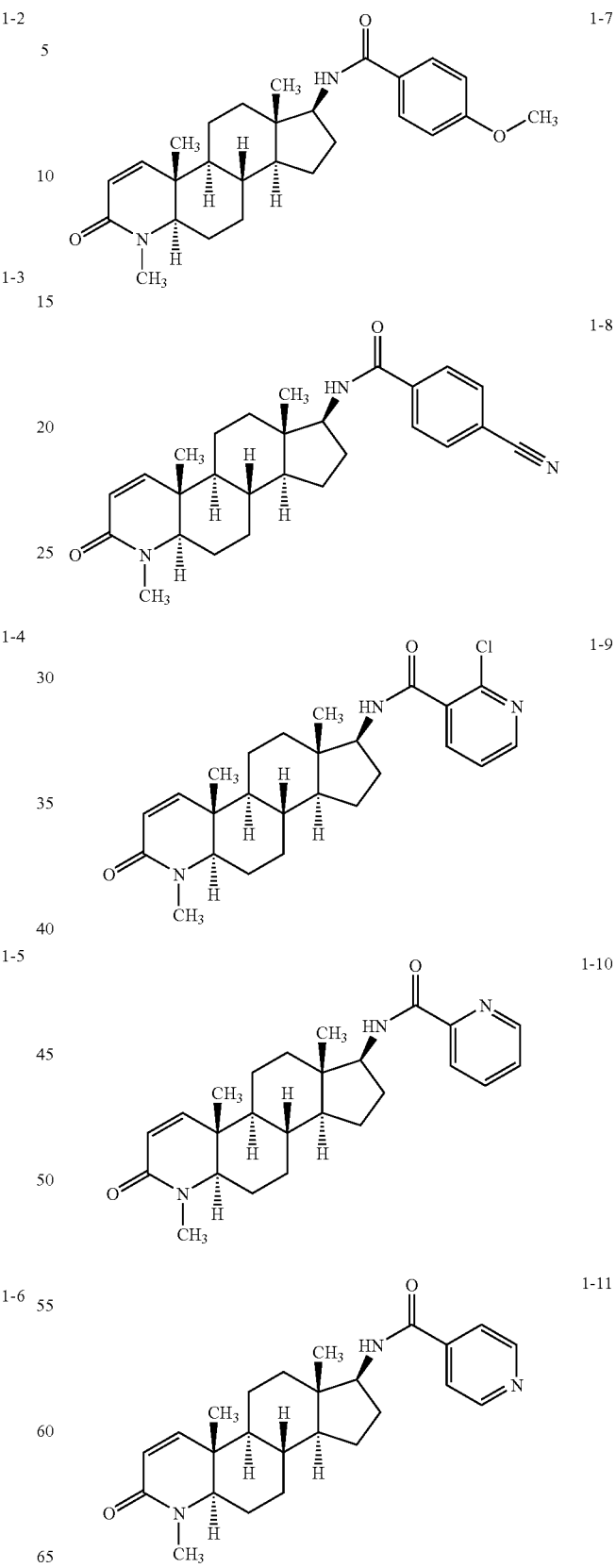

TABLE 1-continued
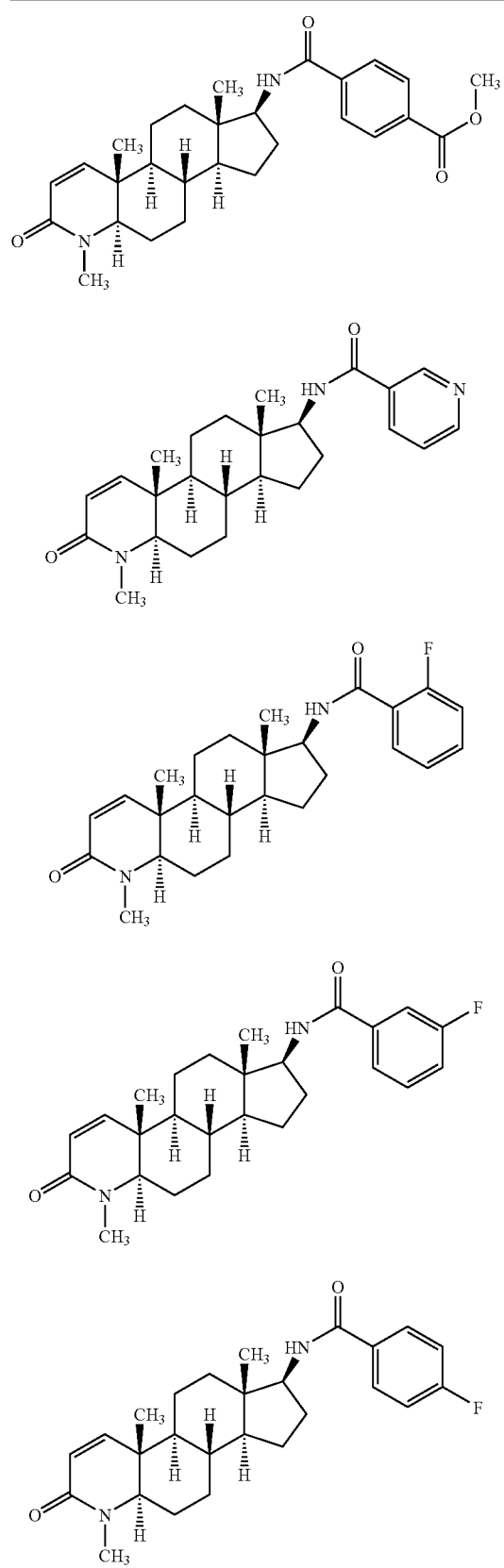
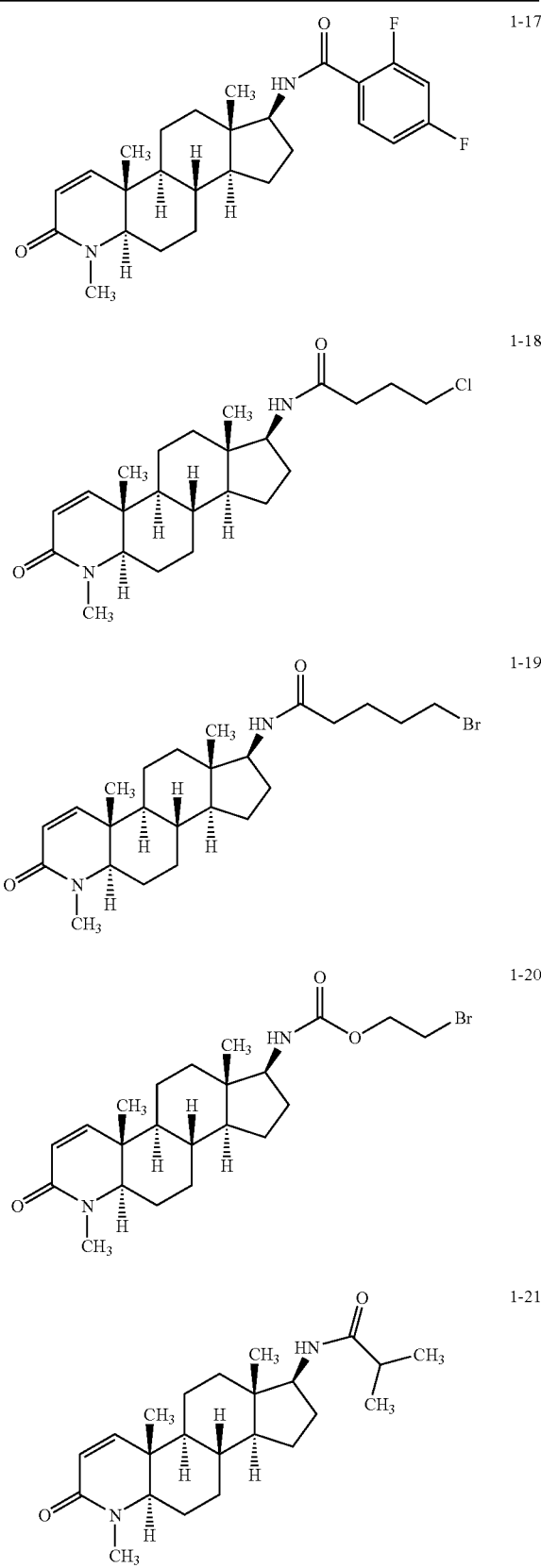

TABLE 1-continued
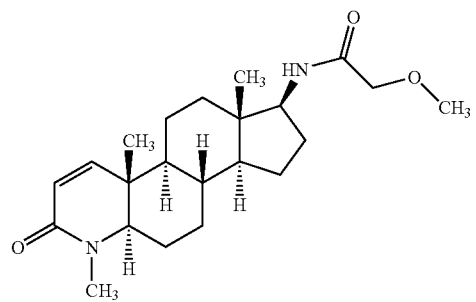
1-22
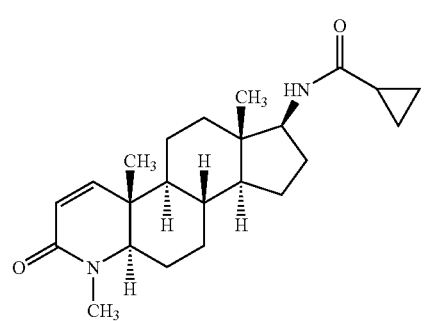
1-23
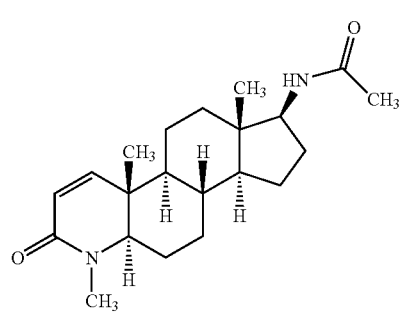
1-24
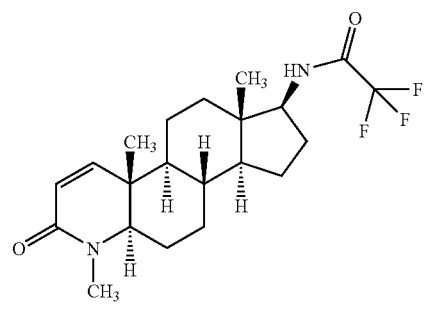
1-25
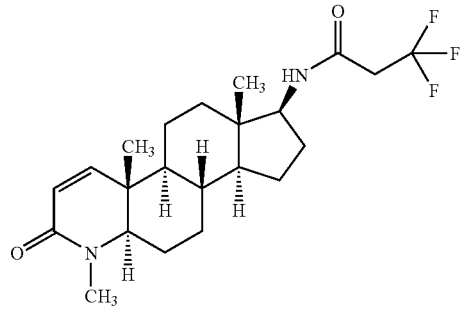
1-26
TABLE 1-continued
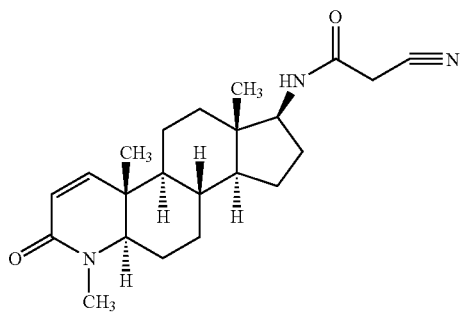
1-27
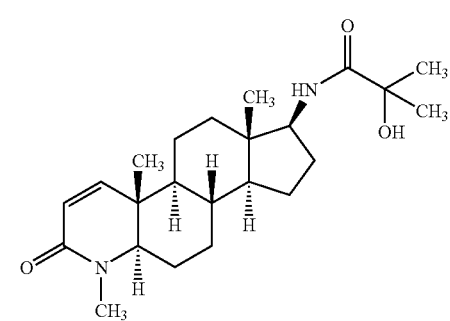
1-28
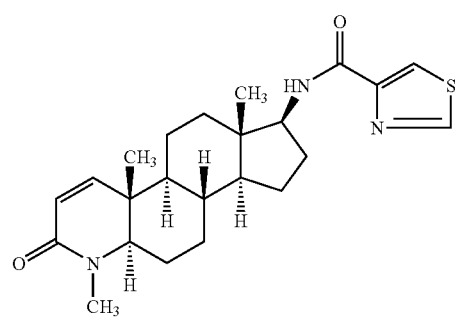
1-29
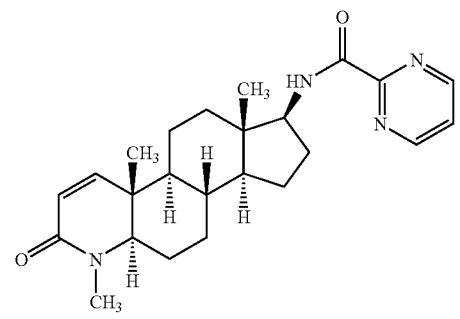
1-30
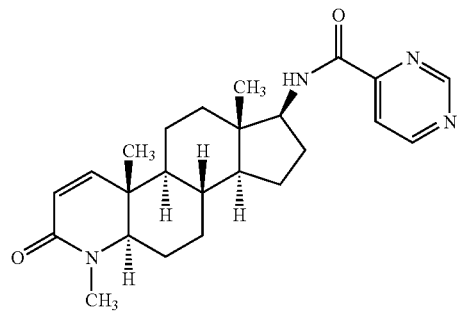
1-31

TABLE 1-continued
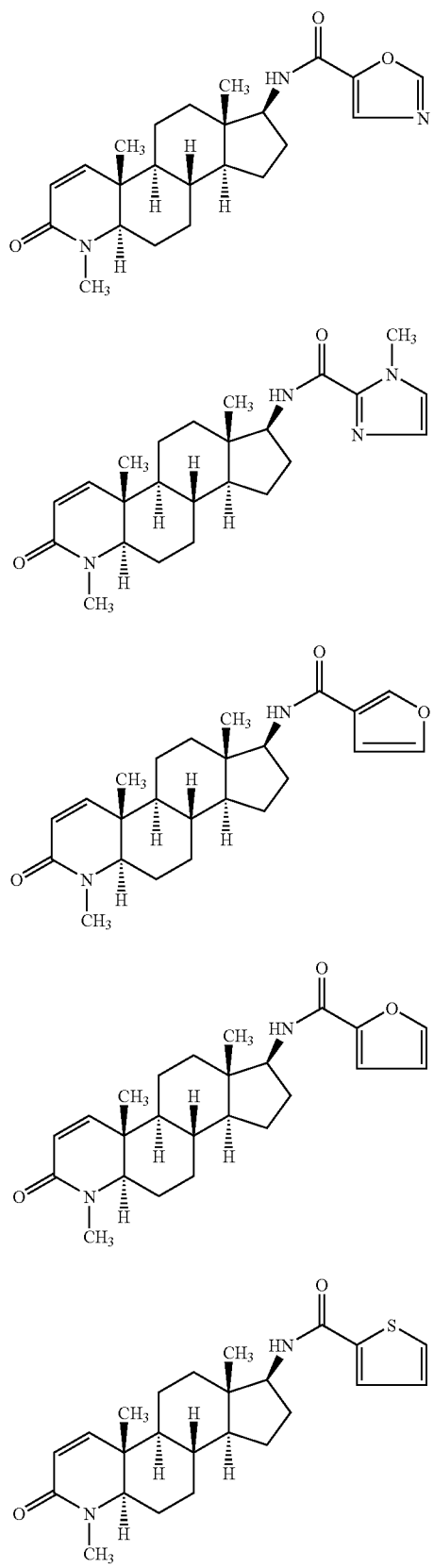
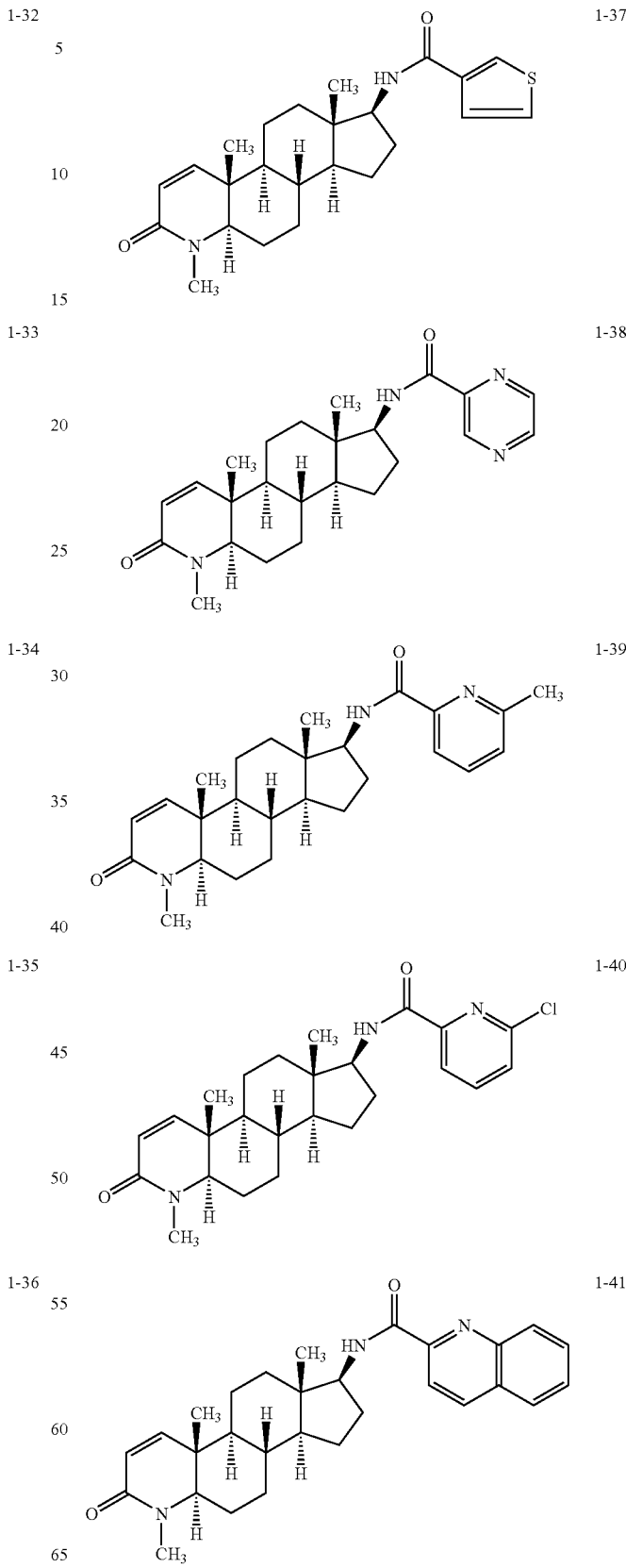

TABLE 1-continued
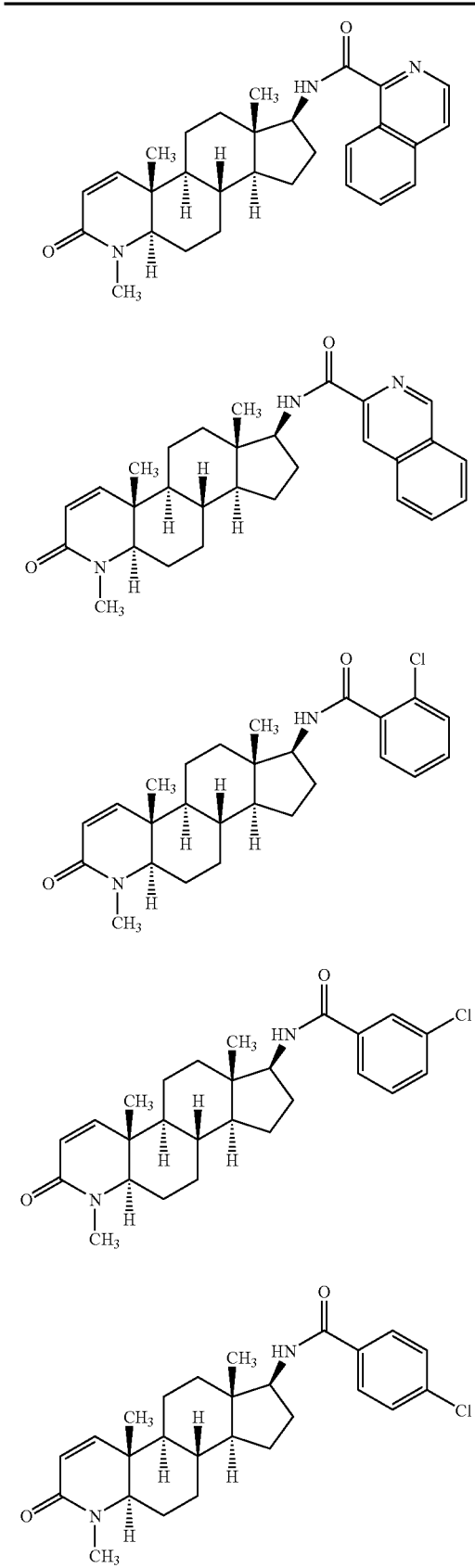
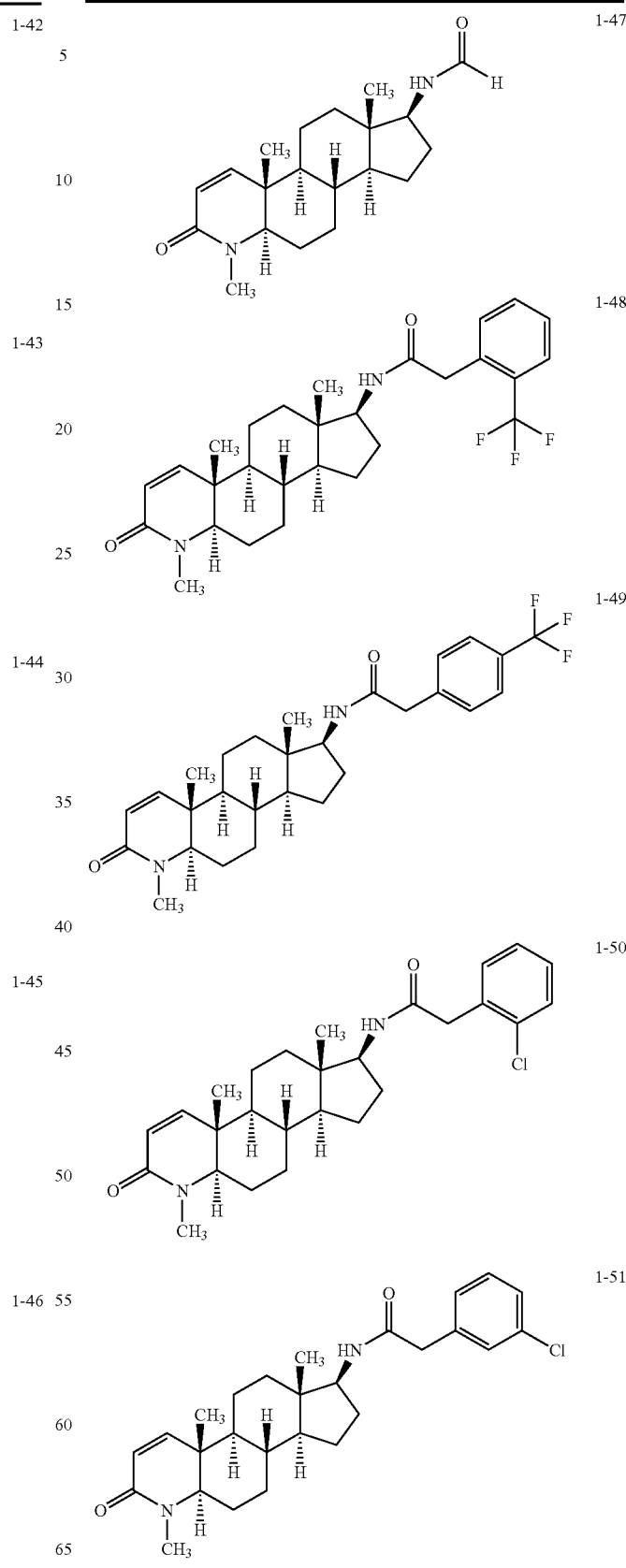

TABLE 1-continued
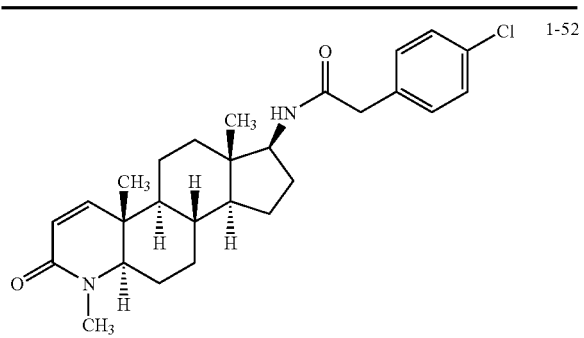
1-52
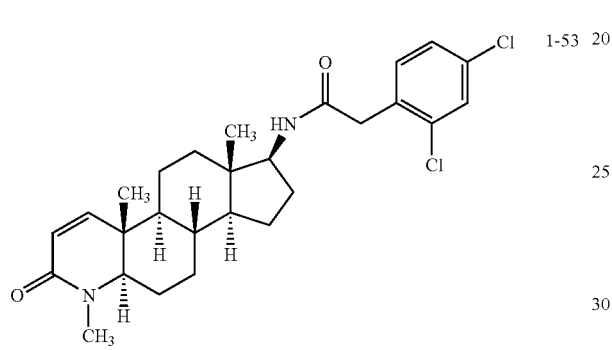
1-53
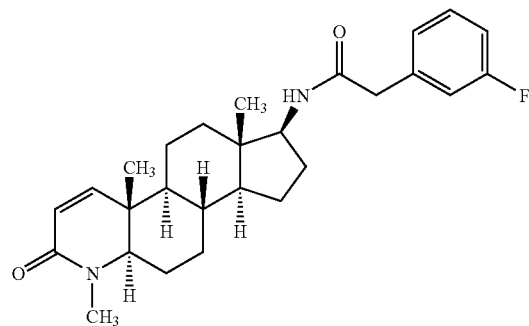
1-54
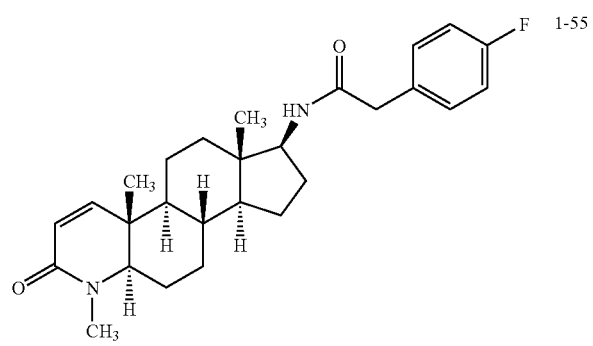
1-55
TABLE 1-continued
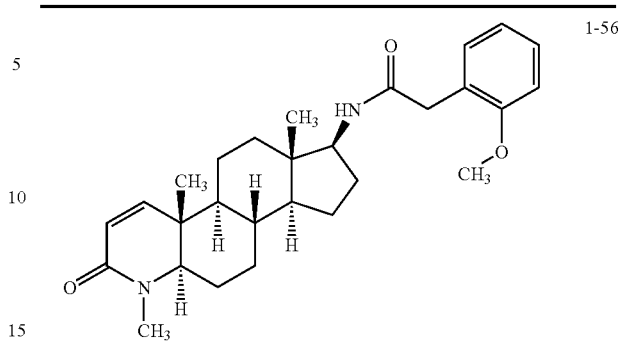
1-56
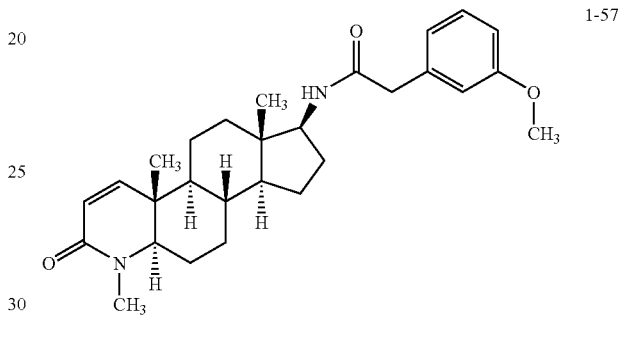
1-57
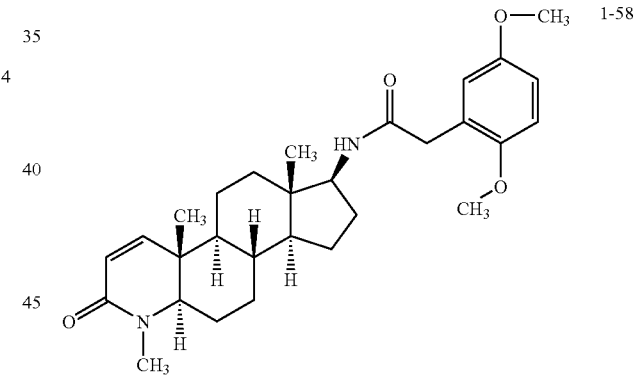
1-58
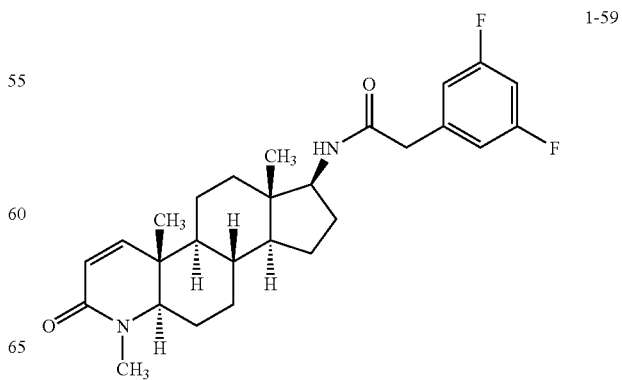
1-59

TABLE 1-continued
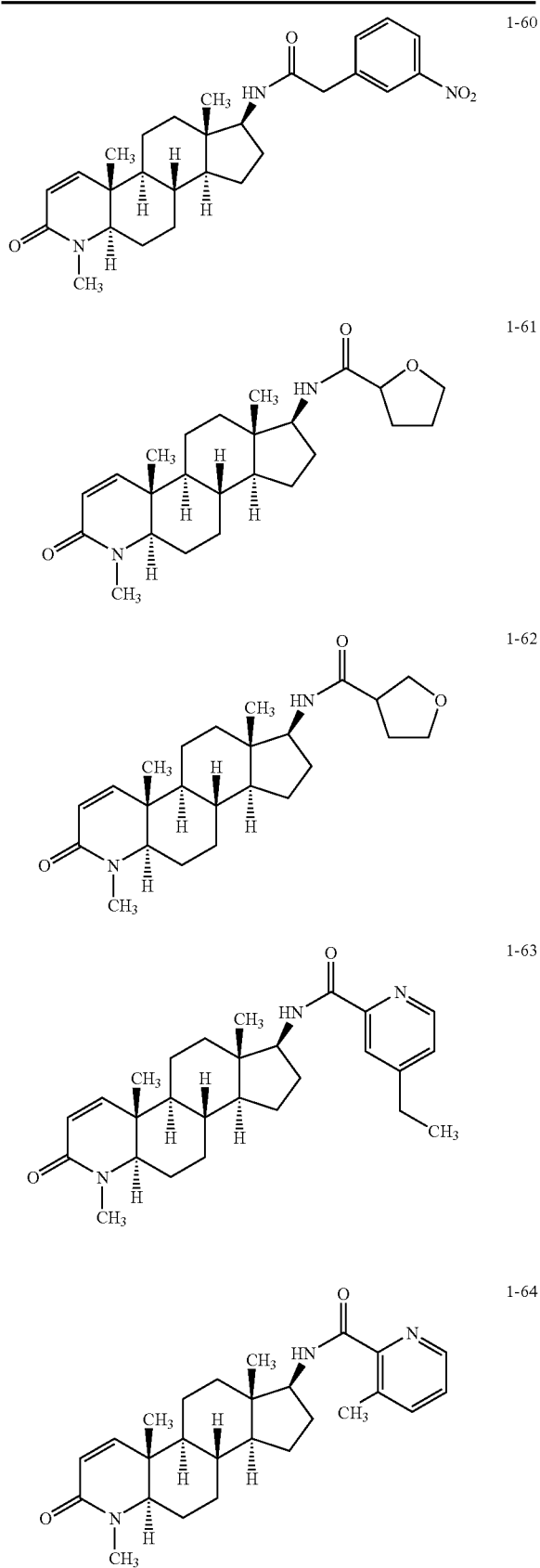

TABLE 1-continued
1-70 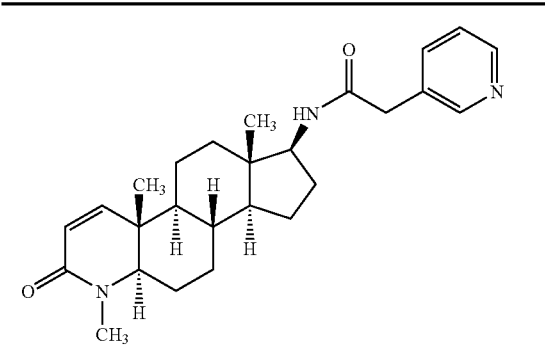
1-71 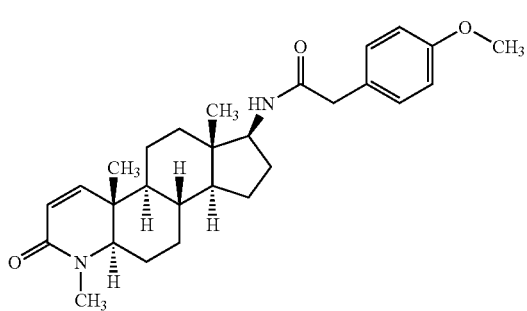
1-72 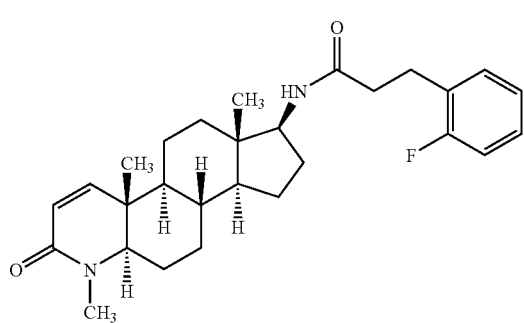
1-73 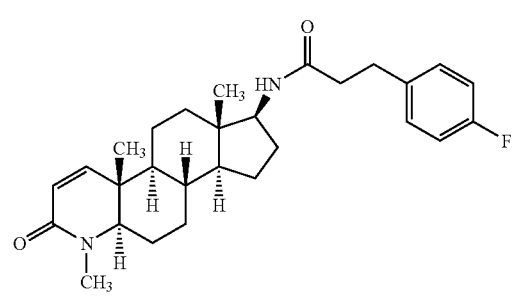
1-74 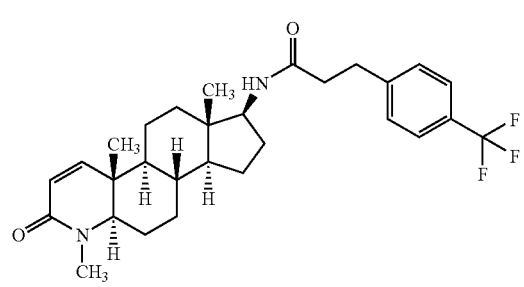
TABLE 1-continued
1-75 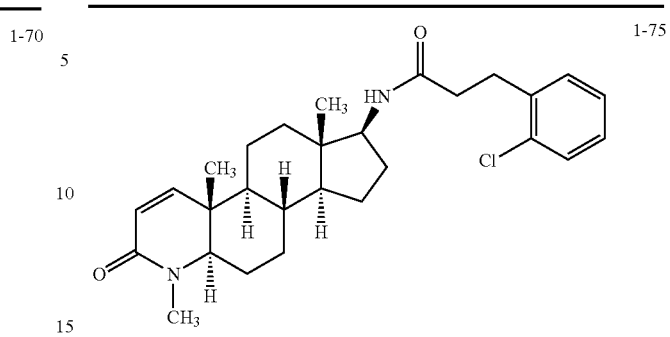
1-76 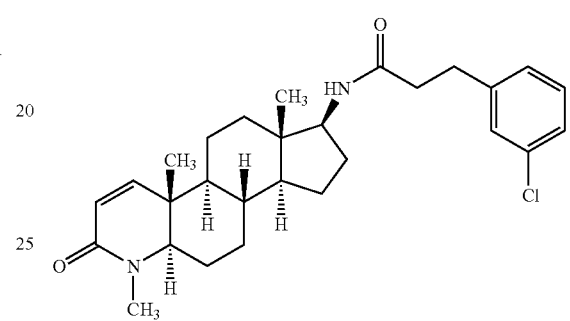
1-77 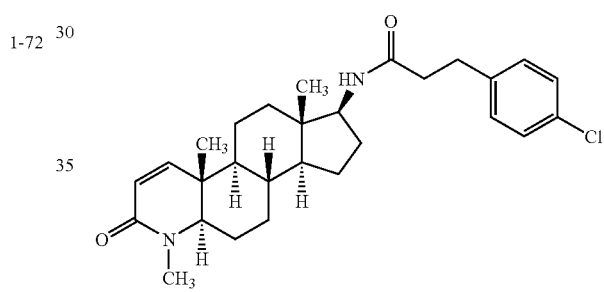
1-78 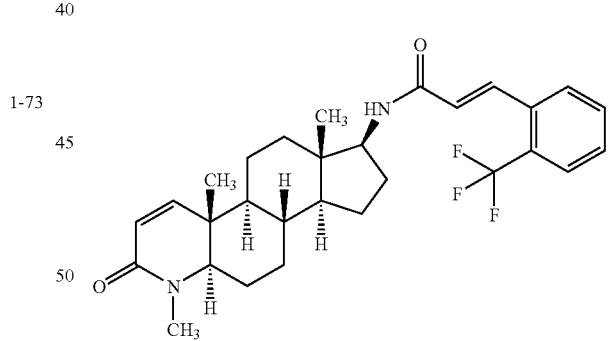
1-79 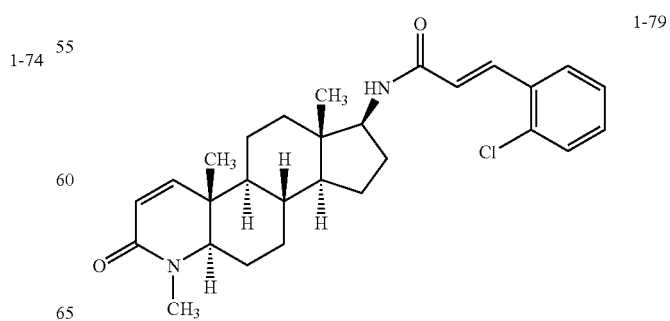

TABLE 1-continued

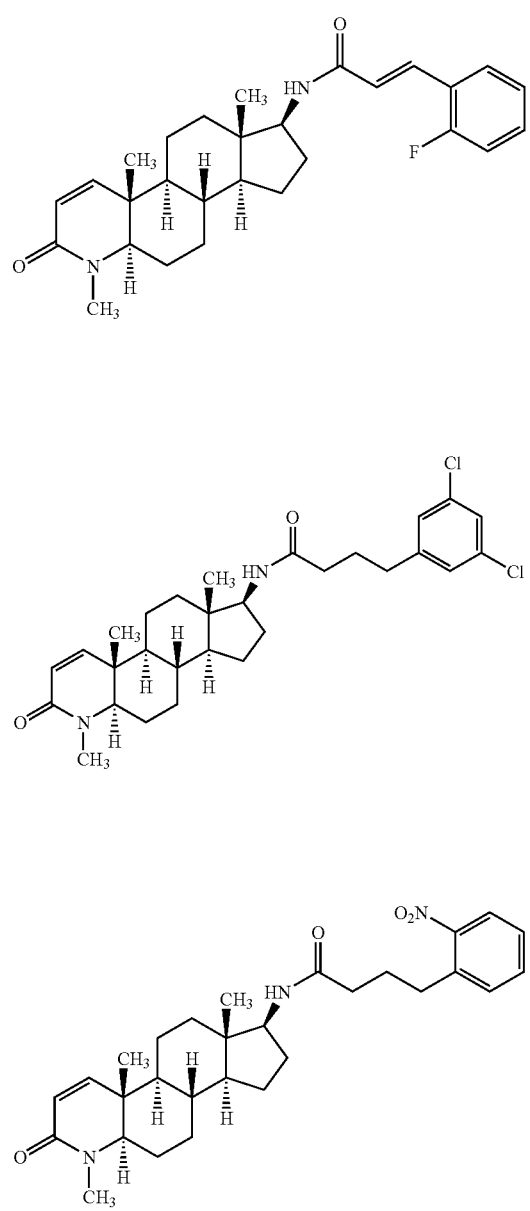

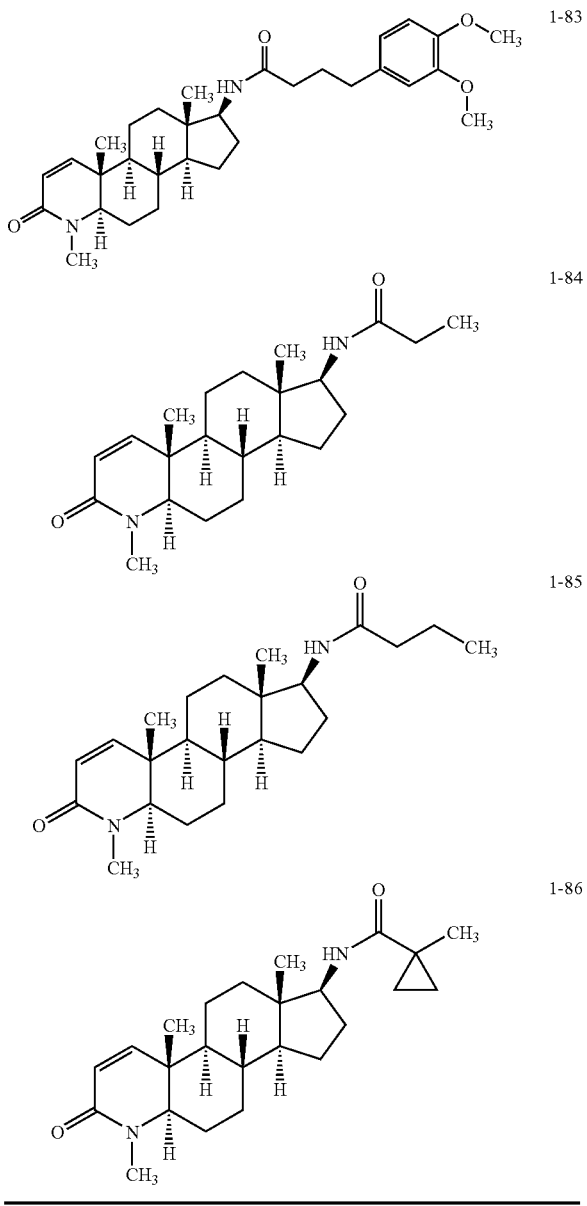

TABLE 2

| Compound Number | Name | [M + H]+ Found |
|---|---|---|
| 1-2 | 4-methyl-17β-amino-4-aza-5α-androst-1-ene-3-one | 303.2437 |
| 1-3 | 4-methyl-17β-(2-trifluoromethylbenzamido)-4-aza-5α-androst-1-ene-3-one | 475.2597 |
| 1-4 | 4-methyl-17β-(3-trifluoromethylbenzamido)-4-aza-5α-androst-1-ene-3-one | 475.2587 |
| 1-5 | 4-methyl-17β-(2-methoxybenzamido)-4-aza-5α-androst-1-ene-3-one | 437.2813 |
| 1-6 | 4-methyl-17β-(3-methoxybenzamido)-4-aza-5α-androst-1-ene-3-one | 437.2807 |
| 1-7 | 4-methyl-17β-(4-methoxybenzamido)-4-aza-5α-androst-1-ene-3-one | 437.2794 |
| 1-8 | 4-methyl-17β-(4-cyanobenzamido)-4-aza-5α-androst-1-ene-3-one | 432.2630 |

TABLE 2-continued

| Compound Number | Name | [M + H]+ Found |
|---|---|---|
| 1-9 | 4-methyl-17β-(2-chloro-pyrid-3-yl-amido)-4-aza-5α-androst-1-ene-3-one | 442.2246 |
| 1-10 | 4-methyl-17β-(pyrid-2-yl-amido)-4-aza-5α-androst-1-ene-3-one | 408.2655 |
| 1-11 | 4-methyl-17β-(pyrid-4-yl-amido)-4-aza-5α-androst-1-ene-3-one | 408.2655 |
| 1-12 | 4-methyl-17β-(4-(carboxymethyl)benzamido)-4-aza-5α-androst-1-ene-3-one | 465.2734 |
| 1-13 | 4-methyl-17β-(pyrid-3-yl-amido)-4-aza-5α-androst-1-ene-3-one | 408.2650 |
| 1-14 | 4-methyl-17β-(2-fluorobenzamido)-4-aza-5α-androst-1-ene-3-one | 425.2617 |
| 1-15 | 4-methyl-17β-(3-fluorobenzamido)-4-aza-5α-androst-1-ene-3-one | 425.2598 |
| 1-16 | 4-methyl-17β-(4-fluorobenzamido)-4-aza-5α-androst-1-ene-3-one | 425.2603 |
| 1-17 | 4-methyl-17β-(2,4-difluorobenzamido)-4-aza-5α-androst-1-ene-3-one | 443.2511 |
| 1-18 | 4-methyl-17β-(4-chlorobutyramido)-4-aza-5α-androst-1-ene-3-one | 407.2485 |
| 1-19 | 4-methyl-17β-(4-bromobutyramido)-4-aza-5α-androst-1-ene-3-one | 465.2126 |
| 1-20 | Carbamic acid, [(5α,17β)-3-oxo-4-methyl-azaandrost-1-ene-17-yl]-2-bromoethyl ester | 453.1757 |
| 1-21 | 4-methyl-17β-(2-methylpropamido)-4-aza-5α-androst-1-ene-3-one | 373.2871 |
| 1-22 | 4-methyl-17β-(2-methoxyacetamido)-4-aza-5α-androst-1-ene-3-one | 375.2661 |
| 1-23 | 4-methyl-17β-(cyclopropamido)-4-aza-5α-androst-1-ene-3-one | 371.2707 |
| 1-24 | 4-methyl-17β-(acetamido)-4-aza-5α-androst-1-ene-3-one | 345.2558 |
| 1-25 | 4-methyl-17β-(trifluoroacetamido)-4-aza-5α-androst-1-ene-3-one | 399.2257 |
| 1-26 | 4-methyl-17β-(3,3,3-trifluoropropionamido)-4-aza-5α-androst-1-ene-3-one | 413.2411 |
| 1-27 | 4-methyl-17β-(2-cyanoacetamido)-4-aza-5α-androst-1-ene-3-one | 370.2490 |
| 1-28 | 4-methyl-17β-(2-methyl-2-hydroxypropamido)-4-aza-5α-androst-1-ene-3-one | 389.2792 |
| 1-29 | 4-methyl-17β-(thiazo-4-yl-amido)-4-aza-5α-androst-1-ene-3-one | 414.2185 |
| 1-30 | 4-methyl-17β-(pyrimid-2-yl-amido)-4-aza-5α-androst-1-ene-3-one | 409.2591 |
| 1-31 | 4-methyl-17β-(pyrimid-4-yl-amido)-4-aza-5α-androst-1-ene-3-one | 409.2578 |
| 1-32 | 4-methyl-17β-(oxazo-5-yl-amido)-4-aza-5α-androst-1-ene-3-one | 398.2410 |
| 1-33 | 4-methyl-17β-(1-methyl-imidazo-2-yl-amido)-4-aza-5α-androst-1-ene-3-one | 411.2743 |
| 1-34 | 4-methyl-17β-(furan-3-yl-amido)-4-aza-5α-androst-1-ene-3-one | 397.2461 |
| 1-35 | 4-methyl-17β-(furan-2-yl-amido)-4-aza-5α-androst-1-ene-3-one | 397.2472 |
| 1-36 | 4-methyl-17β-(thiophene-2-yl-amido)-4-aza-5α-androst-1-ene-3-one | 413.2231 |
| 1-37 | 4-methyl-17β-(thiophene-3-yl-amido)-4-aza-5α-androst-1-ene-3-one | 413.2229 |
| 1-38 | 4-methyl-17β-(pyridazin-2-yl-amido)-4-aza-5α-androst-1-ene-3-one | 409.2581 |
| 1-39 | 4-methyl-17β-(5-methyl-pyridin-2-yl-amido)-4-aza-5α-androst-1-ene-3-one | 422.2787 |
| 1-40 | 4-methyl-17β-(5-chloro-pyridin-2-yl-amido)-4-aza-5α-androst-1-ene-3-one | 442.2228 |
| 1-41 | 4-methyl-17β-(quinoline-2-yl-amido)-4-aza-5α-androst-1-ene-3-one | 458.2786 |
| 1-42 | 4-methyl-17β-(quinoline-8-yl-amido)-4-aza-5α-androst-1-ene-3-one | 458.2788 |
| 1-43 | 4-methyl-17β-(isoquinoline-8-yl-amido)-4-aza-5α-androst-1-ene-3-one | 458.2793 |
| 1-44 | 4-methyl-17β-(2-chlorobenzamido)-4-aza-5α-androst-1-ene-3-one | 441.2299 |

TABLE 2-continued

| Compound Number | Name | [M + H]+ Found |
|---|---|---|
| 1-45 | 4-methyl-17β-(3-chlorobenzamido)-4-aza-5α-androst-1-ene-3-one | 441.2292 |
| 1-46 | 4-methyl-17β-(4-chlorobenzamido)-4-aza-5α-androst-1-ene-3-one | 441.2292 |
| 1-47 | 4-methyl-17β-(formamido)-4-aza-5α-androst-1-ene-3-one | 331.2375 |
| 1-48 | 4-methyl-17β-[(2-trifluoromethylphenyl)acetamido]-4-aza-5α-androst-1-ene-3-one | 489.2724 |
| 1-49 | 4-methyl-17β-[(4-trifluoromethylphenyl)acetamido]-4-aza-5α-androst-1-ene-3-one | 489.2724 |
| 1-50 | 4-methyl-17β-[(2-chlorophenyl)acetamido]-4-aza-5α-androst-1-ene-3-one | 455.2460 |
| 1-51 | 4-methyl-17β-[(3-chlorophenyl)acetamido]-4-aza-5α-androst-1-ene-3-one | 455.2460 |
| 1-52 | 4-methyl-17β-[(4-chlorophenyl)acetamido]-4-aza-5α-androst-1-ene-3-one | 455.2460 |
| 1-53 | 4-methyl-17β-[(2,4-dichlorophenyl)acetamido]-4-aza-5α-androst-1-ene-3-one | 489.2070 |
| 1-54 | 4-methyl-17β-[(3-fluorophenyl)acetamido]-4-aza-5α-androst-1-ene-3-one | 439.2756 |
| 1-55 | 4-methyl-17β-[(4-fluorophenyl)acetamido]-4-aza-5α-androst-1-ene-3-one | 439.2756 |
| 1-56 | 4-methyl-17β-[(2-methoxyphenyl)acetamido]-4-aza-5α-androst-1-ene-3-one | 451.2955 |
| 1-57 | 4-methyl-17β-[(3-methoxyphenyl)acetamido]-4-aza-5α-androst-1-ene-3-one | 451.2955 |
| 1-58 | 4-methyl-17β-[(2,5-dimethoxyphenyl)acetamido]-4-aza-5α-androst-1-ene-3-one | 481.3061 |
| 1-59 | 4-methyl-17β-[(3,5-difluorophenyl)acetamido]-4-aza-5α-androst-1-ene-3-one | 457.2661 |
| 1-60 | 4-methyl-17β-[(3-nitrophenyl)acetamido]-4-aza-5α-androst-1-ene-3-one | 466.2701 |
| 1-61 | 4-methyl-17β-(tetrahydrofuran-2-yl-amido)-4-aza-5α-androst-1-ene-3-one | 401.2799 |
| 1-62 | 4-methyl-17β-(tetrahydrofuran-3-yl-amido)-4-aza-5α-androst-1-ene-3-one | 401.2799 |
| 1-63 | 4-methyl-17β-(4-ethyl-pyridin-2-yl-amido)-4-aza-5α-androst-1-ene-3-one | 436.2959 |
| 1-64 | 4-methyl-17β-(3-methyl-pyridin-2-yl-amido)-4-aza-5α-androst-1-ene-3-one | 422.2802 |
| 1-65 | 4-methyl-17β-(3-bromo-pyridin-2-yl-amido)-4-aza-5α-androst-1-ene-3-one | 486.1751 |
| 1-66 | 4-methyl-17β-(4-bromo-pyridin-2-yl-amido)-4-aza-5α-androst-1-ene-3-one | 486.1751 |
| 1-67 | 4-methyl-17β-[(2-phenylcyclopropyl)amido]-4-aza-5α-androst-1-ene-3-one | 447.3006 |
| 1-68 | 4-methyl-17β-[(2-fluorophenyl)acetamido]-4-aza-5α-androst-1-ene-3-one | 439.2756 |
| 1-69 | 4-methyl-17β-[(pyrid-2-yl)acetamido]-4-aza-5α-androst-1-ene-3-one | 422.2802 |
| 1-70 | 4-methyl-17β-[(pyrid-3-yl)acetamido]-4-aza-5α-androst-1-ene-3-one | 422.2802 |
| 1-71 | 4-methyl-17β-[(4-methoxyphenyl)acetamido]-4-aza-5α-androst-1-ene-3-one | 451.2955 |
| 1-72 | 4-methyl-17β-[3-(2-fluorophenyl)propionamido]-4-aza-5α-androst-1-ene-3-one | 453.2924 |
| 1-73 | 4-methyl-17β-[3-(4-fluorophenyl)propionamido]-4-aza-5α-androst-1-ene-3-one | 453.2931 |
| 1-74 | 4-methyl-17β-[3-(4-trifluoromethylphenyl)propionamido]-4-aza-5α-androst-1-ene-3-one | 503.2874 |
| 1-75 | 4-methyl-17β-[3-(2-chlorophenyl)propionamido]-4-aza-5α-androst-1-ene-3-one | 469.2635 |
| 1-76 | 4-methyl-17β-[3-(3-chlorophenyl)propionamido]-4-aza-5α-androst-1-ene-3-one | 469.2633 |
| 1-77 | 4-methyl-17β-[3-(4-chlorophenyl)propionamido]-4-aza-5α-androst-1-ene-3-one | 469.2638 |
| 1-78 | 4-methyl-17β-[2-trifluoromethylcinnamido]-4-aza-5α-androst-1-ene-3-one | 501.2723 |
| 1-79 | 4-methyl-17β-[2-chlorocinnamido]-4-aza-5α-androst-1-ene-3-one | 467.2478 |
| 1-80 | 4-methyl-17β-[2-fluorocinnamido]-4-aza-5α-androst-1-ene-3-one | 451.2752 |
| 1-81 | 4-methyl-17β-[4-(2,5-dichlorophenyl)butanamido]-4-aza-5α-androst-1-ene-3-one | 517.2381 |

TABLE 2-continued

| Compound Number | Name | [M + H]+ Found |
|---|---|---|
| 1-82 | 4-methyl-17β-[4-(2-nitrophenyl)butanamido]-4-aza-5α-androst-1-ene-3-one | 494.3009 |
| 1-83 | 4-methyl-17β-[4-(3,4-dimethoxyphenyl)butanamido]-4-aza-5α-androst-1-ene-3-one | 509.336 |
| 1-84 | 4-methyl-17β-[propionamido]-4-aza-5α-androst-1-ene-3-one | 359.2707 |
| 1-85 | 4-methyl-17β-[butyramido]-4-aza-5α-androst-1-ene-3-one | 373.2844 |
| 1-86 | 4-methyl-17β-[(2-methyl)cyclopropamido]-4-aza-5α-androst-1-ene-3-one | 385.2842 |

EXAMPLE 2

Preparation of 4-methyl-17β-(2-trifluoromethylbenzamido)-4-aza-5α-androst-1-ene-3-one (2-2)

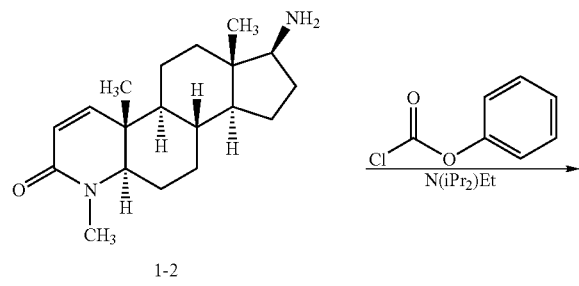

1-2

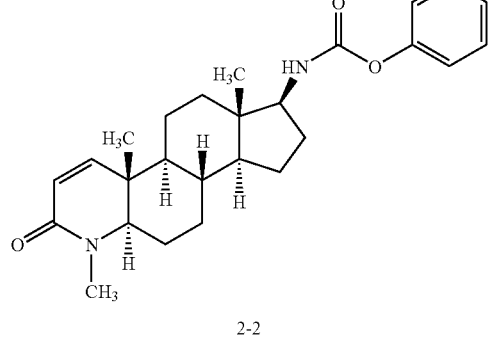

2-2

Amine 1-2 (100 mg, 0.331 mmol), diisopropylethylamine (120 μL, 0.662 mmol), phenyl chloroformate (50 μL, 0.397 mmol) and CH$_2$Cl$_2$ (1 mL) were combined and then stirred overnight. The organic portion was separated, dried over magnesium sulfate, and evaporated. The resulting residue was and purified by flash chromatography (silica, hexanes→EtOAc) providing compound 2-2 as a white solid.

HRMS (FAB, M+1) found 423.2672

Utilizing the same general procedure as described for compound 2-2 in Example 2, and by varying the chloroformate reagent, compounds 2-3 through 2-40 were prepared (Table 3); mass spectral characterization of these compounds is listed in Table 4.

TABLE 3

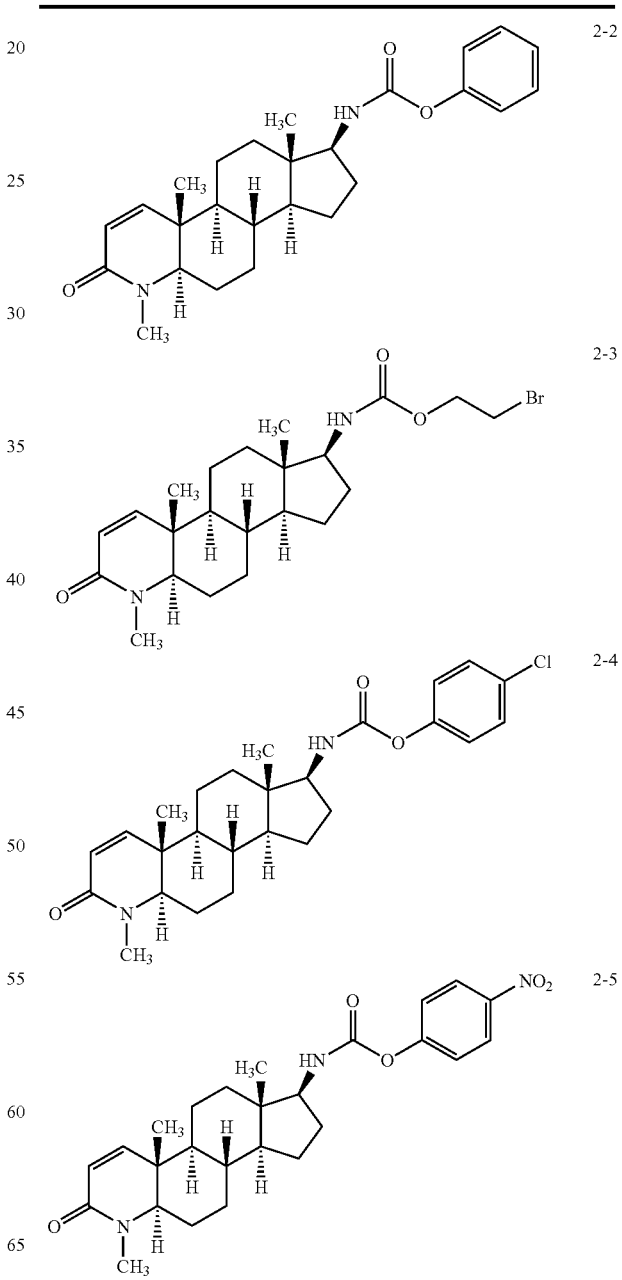

TABLE 3-continued
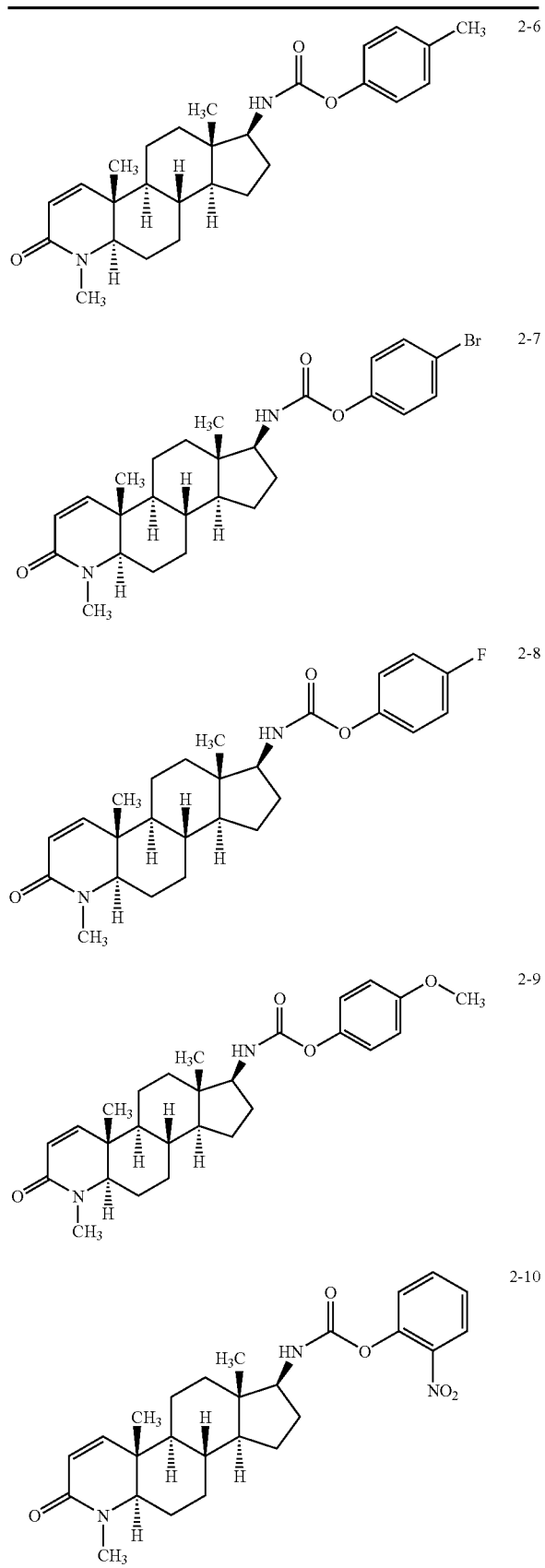
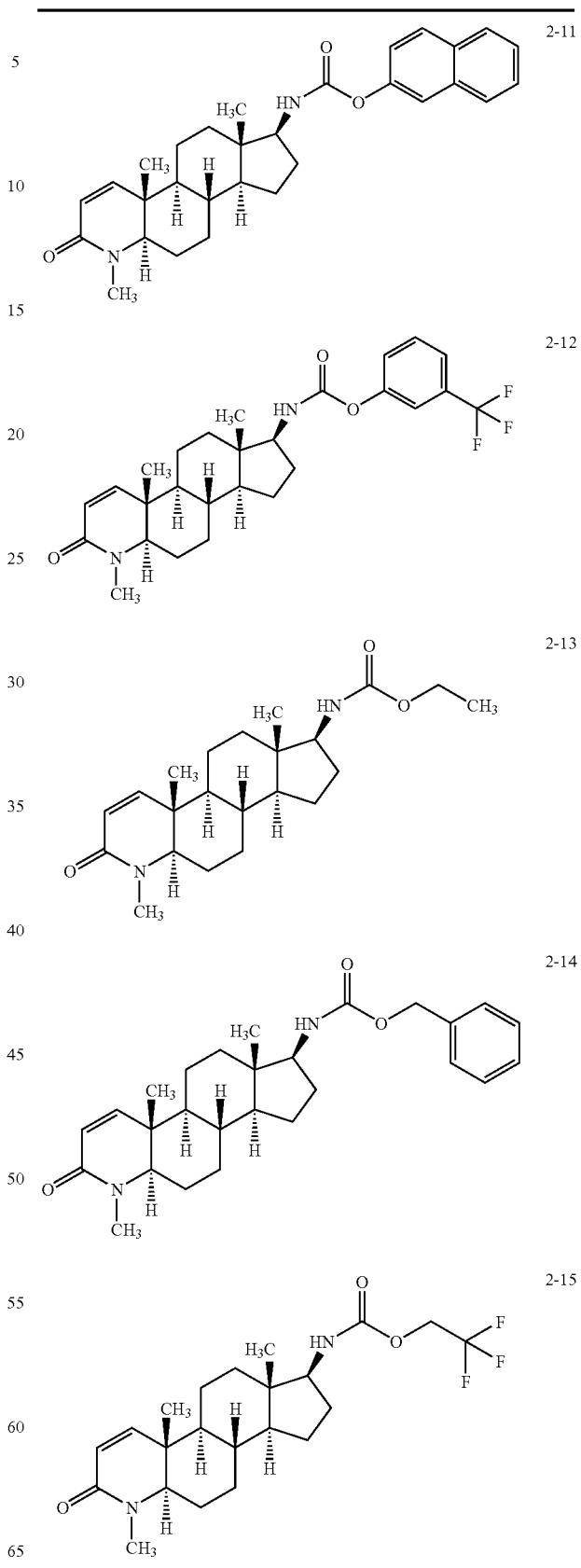

TABLE 3-continued
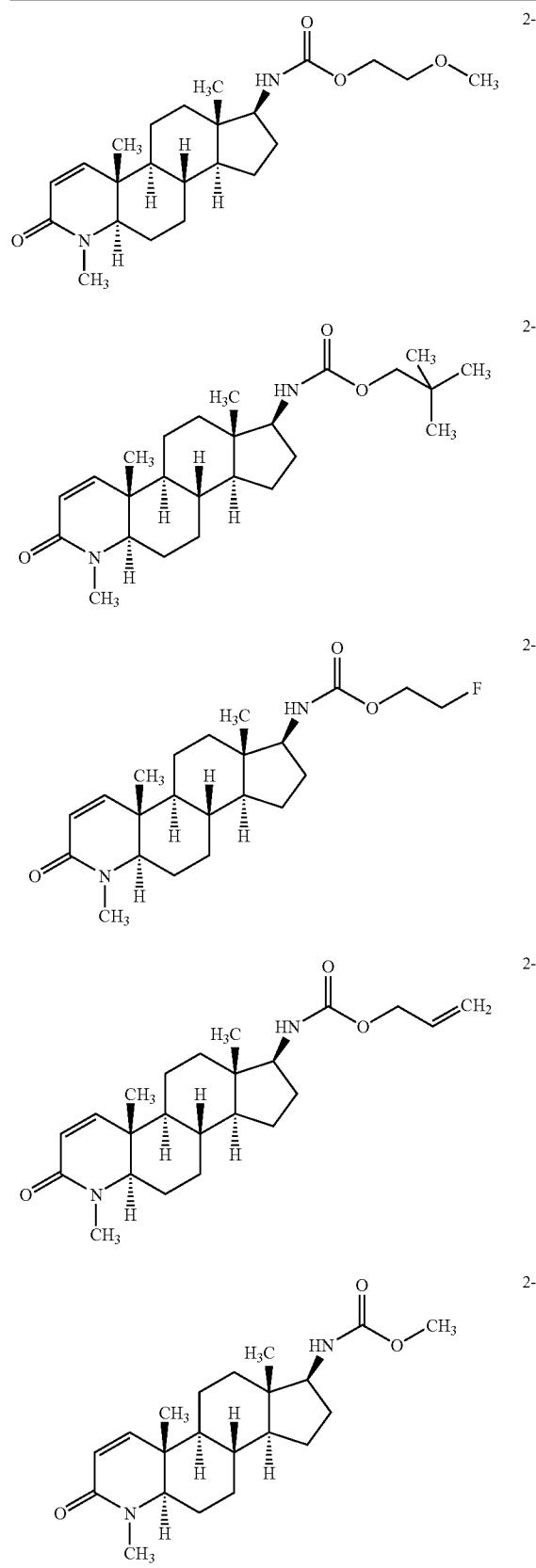
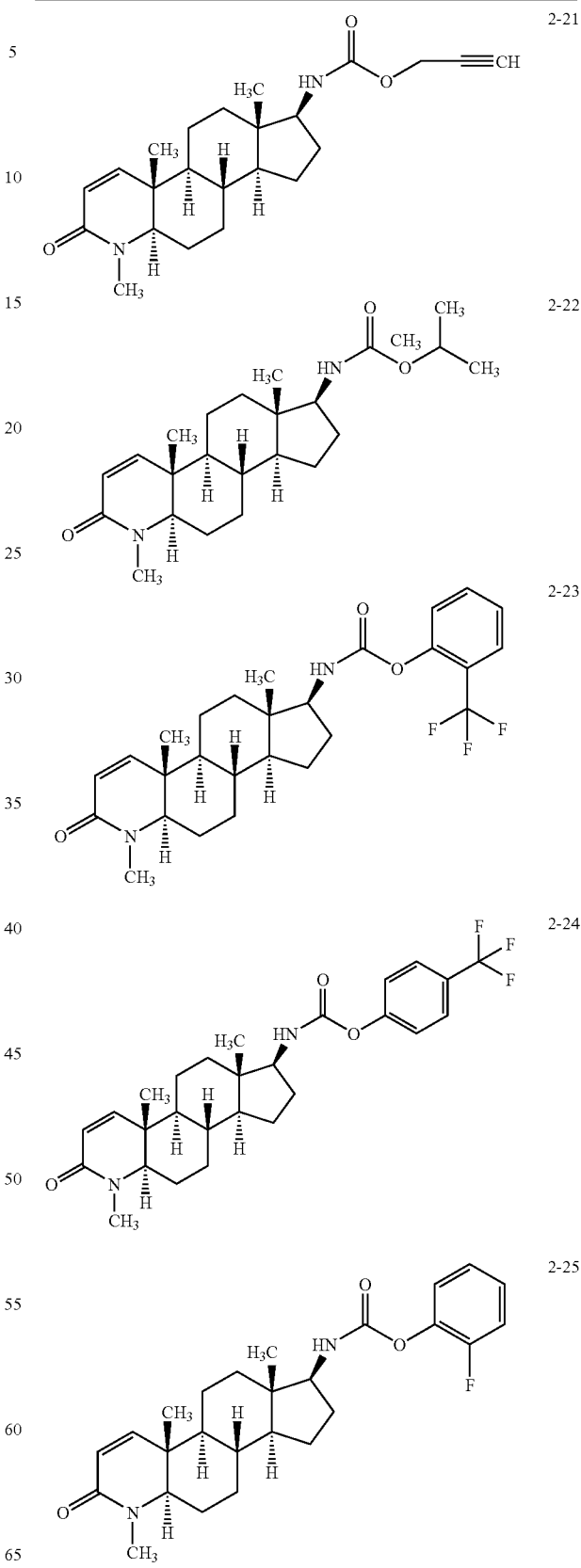

TABLE 3-continued
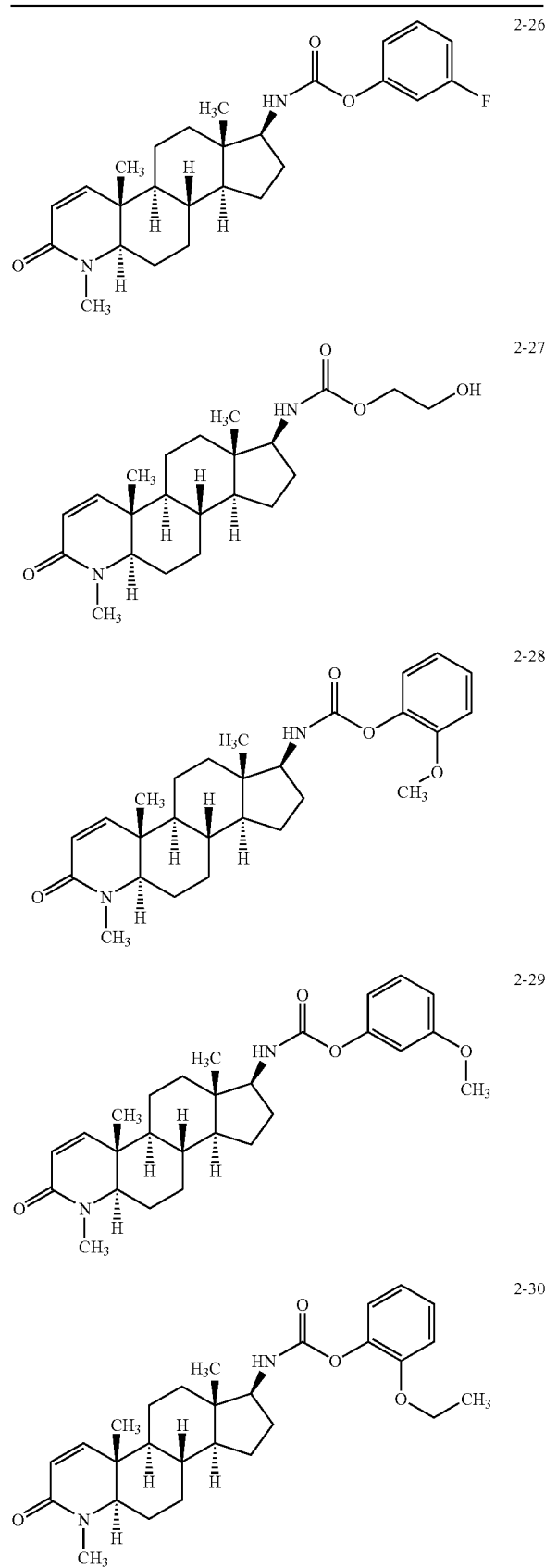
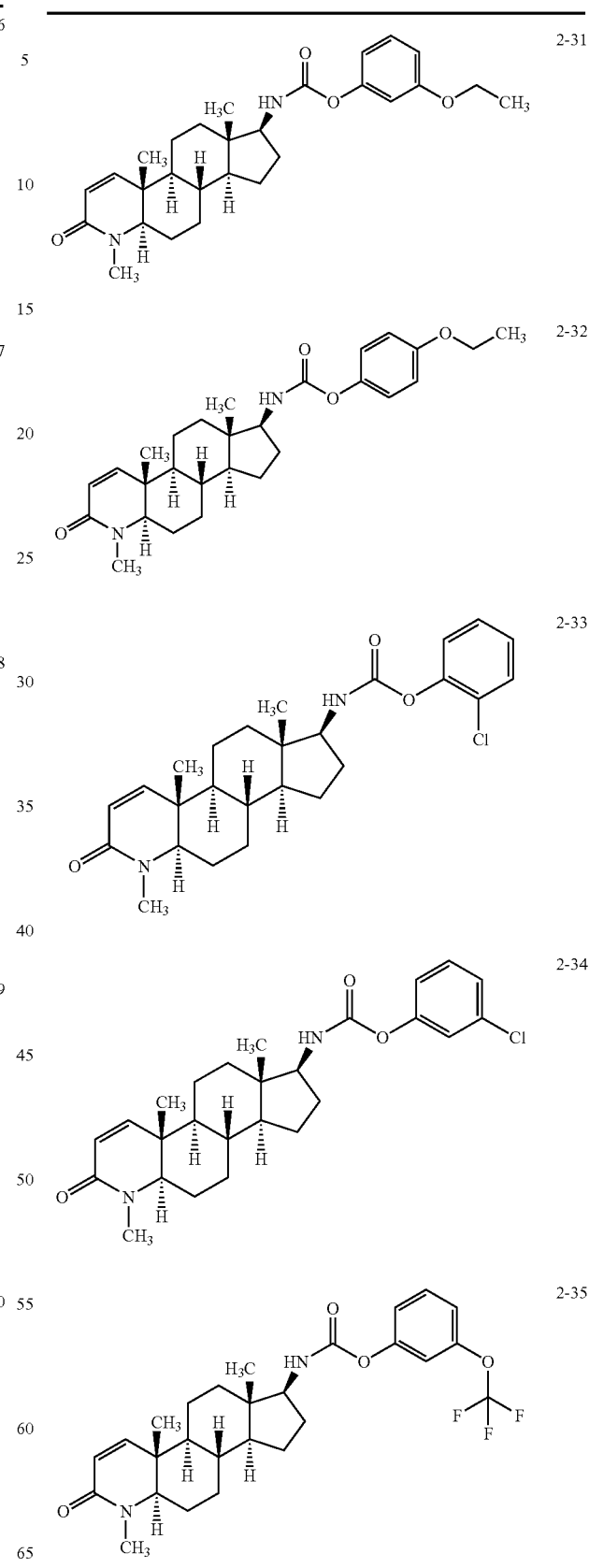

TABLE 3-continued 2-36 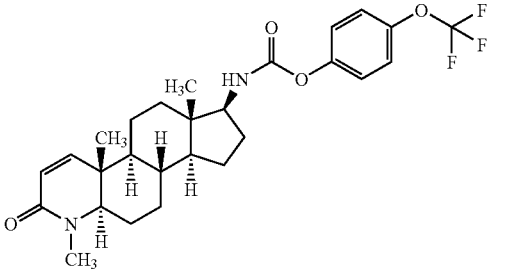

2-37 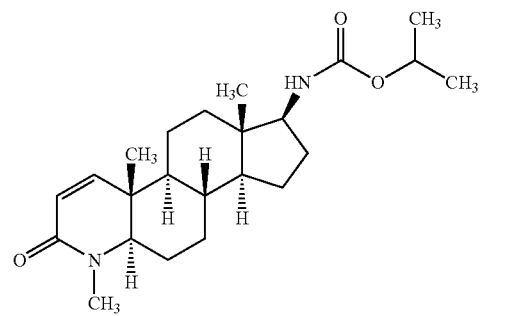

2-38 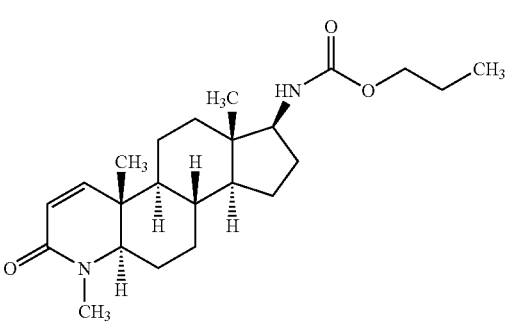

2-39 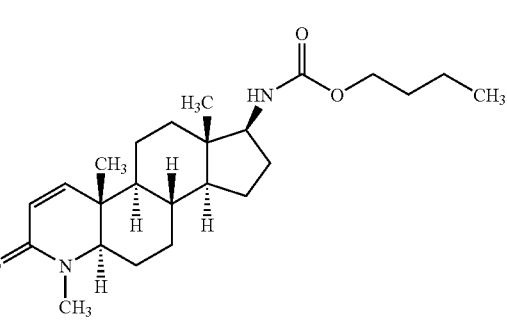

2-40 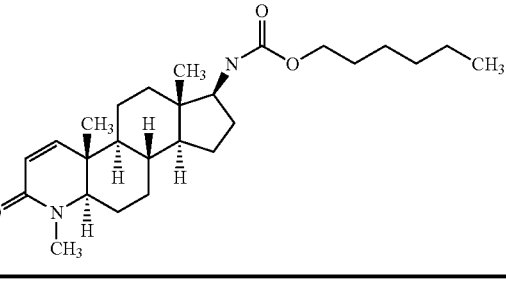

TABLE 4

| Compound Number | Name | Found [M + H]+ |
|---|---|---|
| 2-2 | Carbamic acid, [(5α,17β)-3-oxo-4-methyl-azaandrost-1-ene-17-yl]-phenyl ester | 423.2672 |
| 2-3 | Carbamic acid, [(5α,17β)-3-oxo-4-methyl-azaandrost-1-ene-17-yl]-2-bromoethyl ester | 453.1757 |
| 2-4 | Carbamic acid, [(5α,17β)-3-oxo-4-methyl-azaandrost-1-ene-17-yl]-4-chlorophenyl ester | 457.2283 |
| 2-5 | Carbamic acid, [(5α,17β)-3-oxo-4-methyl-azaandrost-1-ene-17-yl]-4-nitrophenyl ester | 468.2535 |
| 2-6 | Carbamic acid, [(5α,17β)-3-oxo-4-methyl-azaandrost-1-ene-17-yl]-4-methylphenyl ester | 437.2810 |
| 2-7 | Carbamic acid, [(5α,17β)-3-oxo-4-methyl-azaandrost-1-ene-17-yl]-4-bromophenyl ester | 501.1792 |
| 2-8 | Carbamic acid, [(5α,17β)-3-oxo-4-methyl-azaandrost-1-ene-17-yl]-4-fluorophenyl ester | 441.2574 |
| 2-9 | Carbamic acid, [(5α,17β)-3-oxo-4-methyl-azaandrost-1-ene-17-yl]-4-methoxphenyl ester | 453.2775 |
| 2-10 | Carbamic acid, [(5α,17β)-3-oxo-4-methyl-azaandrost-1-ene-17-yl]-2-nitrophenyl ester | 468.2531 |
| 2-11 | Carbamic acid, [(5α,17β)-3-oxo-4-methyl-azaandrost-1-ene-17-yl]-3-naphthyl ester | 473.2840 |
| 2-12 | Carbamic acid, [(5α,17β)-3-oxo-4-methyl-azaandrost-1-ene-17-yl]-3-trifluoromethylphenyl ester | 491.2551 |
| 2-13 | Carbamic acid, [(5α,17β)-3-oxo-4-methyl-azaandrost-1-ene-17-yl]-ethyl ester | 375.2661 |
| 2-14 | Carbamic acid, [(5α,17β)-3-oxo-4-methyl-azaandrost-1-ene-17-yl]-benzyl ester | 437.2818 |
| 2-15 | Carbamic acid, [(5α,17β)-3-oxo-4-methyl-azaandrost-1-ene-17-yl]-2,2,2-trifluoroethyl ester | 429.3256 and 429.2411 |
| 2-16 | Carbamic acid, [(5α,17β)-3-oxo-4-methyl-azaandrost-1-ene-17-yl]-2-methoxyethyl ester | 417.3107 |
| 2-17 | Carbamic acid, [(5α,17β)-3-oxo-4-methyl-azaandrost-1-ene-17-yl]-(2,2-dimethylpropy) ester | 393.2553 |
| 2-18 | Carbamic acid, [(5α,17β)-3-oxo-4-methyl-azaandrost-1-ene-17-yl]-2-fluoroethyl ester | 387.2666 |
| 2-18 | Carbamic acid, [(5α,17β)-3-oxo-4-methyl-azaandrost-1-ene-17-yl]-allyl ester | 361.2514 |
| 2-20 | Carbamic acid, [(5α,17β)-3-oxo-4-methyl-azaandrost-1-ene-17-yl]-methyl ester | 385.2514 |
| 2-21 | Carbamic acid, [(5α,17β)-3-oxo-4-methyl-azaandrost-1-ene-17-yl]-1-propynoic ester | 403.2986 |
| 2-22 | Carbamic acid, [(5α,17β)-3-oxo-4-methyl-azaandrost-1-ene-17-yl]-(2-methyl-2-butyl) ester | 442.2344 |
| 2-23 | Carbamic acid, [(5α,17β)-3-oxo-4-methyl-azaandrost-1-ene-17-yl]-2-(trifluoromethyl)phenyl ester | 491.2510 |
| 2-24 | Carbamic acid, [(5α,17β)-3-oxo-4-methyl-azaandrost-1-ene-17-yl]-4-(trifluoromethyl)phenyl ester | 491.2523 |
| 2-25 | Carbamic acid, [(5α,17β)-3-oxo-4-methyl-azaandrost-1-ene-17-yl]-2-fluorophenyl ester | 441.2583 |
| 2-26 | Carbamic acid, [(5α,17β)-3-oxo-4-methyl-azaandrost-1-ene-17-yl]-3-fluorophenyl ester | 441.2595 |
| 2-27 | Carbamic acid, [(5α,17β)-3-oxo-4-methyl-azaandrost-1-ene-17-yl]-(2-hydroxy-1-ethyl) ester | 391.2629 |
| 2-28 | Carbamic acid, [(5α,17β)-3-oxo-4-methyl-azaandrost-1-ene-17-yl]-2-methoxyphenyl ester | 453.2745 |
| 2-29 | Carbamic acid, [(5α,17β)-3-oxo-4-methyl-azaandrost-1-ene-17-yl]-3-methoxyphenyl ester | 453.2775 |
| 2-30 | Carbamic acid, [(5α,17β)-3-oxo-4-methyl-azaandrost-1-ene-17-yl]-2-ethoxyphenyl ester | 467.291 |
| 2-31 | Carbamic acid, [(5α,17β)-3-oxo-4-methyl-azaandrost-1-ene-17-yl]-3-ethoxyphenyl ester | 467.2862 |
| 2-32 | Carbamic acid, [(5α,17β)-3-oxo-4-methyl-azaandrost-1-ene-17-yl]-4-ethoxyphenyl ester | 467.2865 |
| 2-33 | Carbamic acid, [(5α,17β)-3-oxo-4-methyl-azaandrost-1-ene-17-yl]-4-chlorophenyl ester | 457.2229 |
| 2-34 | Carbamic acid, [(5α,17β)-3-oxo-4-methyl-azaandrost-1-ene-17-yl]-3-chlorophenyl ester | 457.2216 |
| 2-35 | Carbamic acid, [(5α,17β)-3-oxo-4-methyl-azaandrost-1-ene-17-yl]-3-(trifluoromethoxy)phenyl ester | 507.2434 |

TABLE 4-continued

| Compound Number | Name | Found [M + H]+ |
|---|---|---|
| 2-36 | Carbamic acid, [(5α,17β)-3-oxo-4-methyl-azaandrost-1-ene-17-yl]-4-(trifluoromethoxy)phenyl ester | 507.2487 |
| 2-37 | Carbamic acid, [(5α,17β)-3-oxo-4-methyl-azaandrost-1-ene-17-yl]-2-propyl ester | 389.281 |
| 2-38 | Carbamic acid, [(5α,17β)-3-oxo-4-methyl-azaandrost-1-ene-17-yl]-1-propyl ester | 389.2847 |
| 2-39 | Carbamic acid, [(5α,17β)-3-oxo-4-methyl-azaandrost-1-ene-17-yl]-1-butyl ester | 403.2998 |
| 2-40 | Carbamic acid, [(5α,17β)-3-oxo-4-methyl-azaandrost-1-ene-17-yl]-1-hexyl ester | 431.3301 |

EXAMPLE 3

Preparation of 4-methyl-17β-(phenylsulfonamido)-4-aza-5α-androst-1-ene-3-one (3-1)

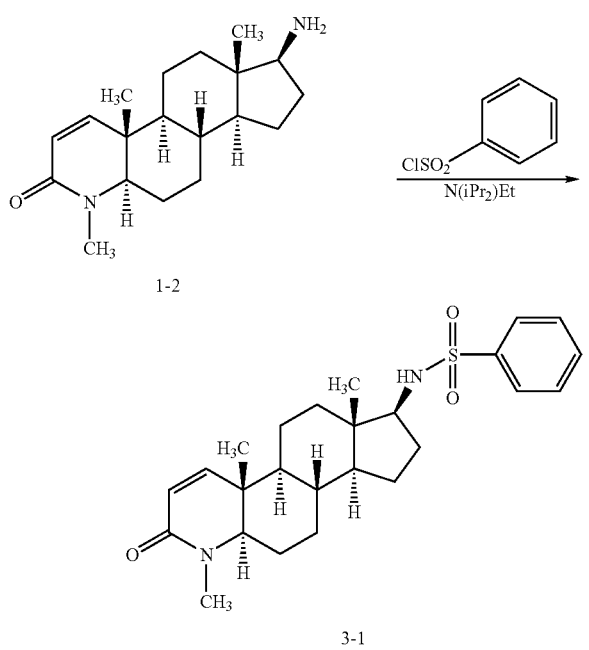

Amine 1-2 (150 mg, 0.497 mmol), diisopropylethylamine (80 µL), phenylsulfonyl chloride (70 µL, 0.550 mmol) and CH₂Cl₂ (3 mL) were combined and then stirred for 1 hour. The reaction was diluted with CH₂Cl₂ and then washed with 10% aqueous KHSO₄. The organic portion was separated, dried over magnesium sulfate, and evaporated. The resulting residue was purified by flash chromatography (silica, hexanes→EtOAc) providing compound 3-1 (0.100 g, 45% yield) as a yellow solid.

HRMS (FAB, M+1) found 443.2376.

Utilizing the same general procedure as described for compound 3-1 in Example 3, and by varying the sulfonyl chloride reagent, compounds 3-2 through 3-13 were prepared (Table 5); mass spectral characterization of these compounds is listed in Table 6.

TABLE 5

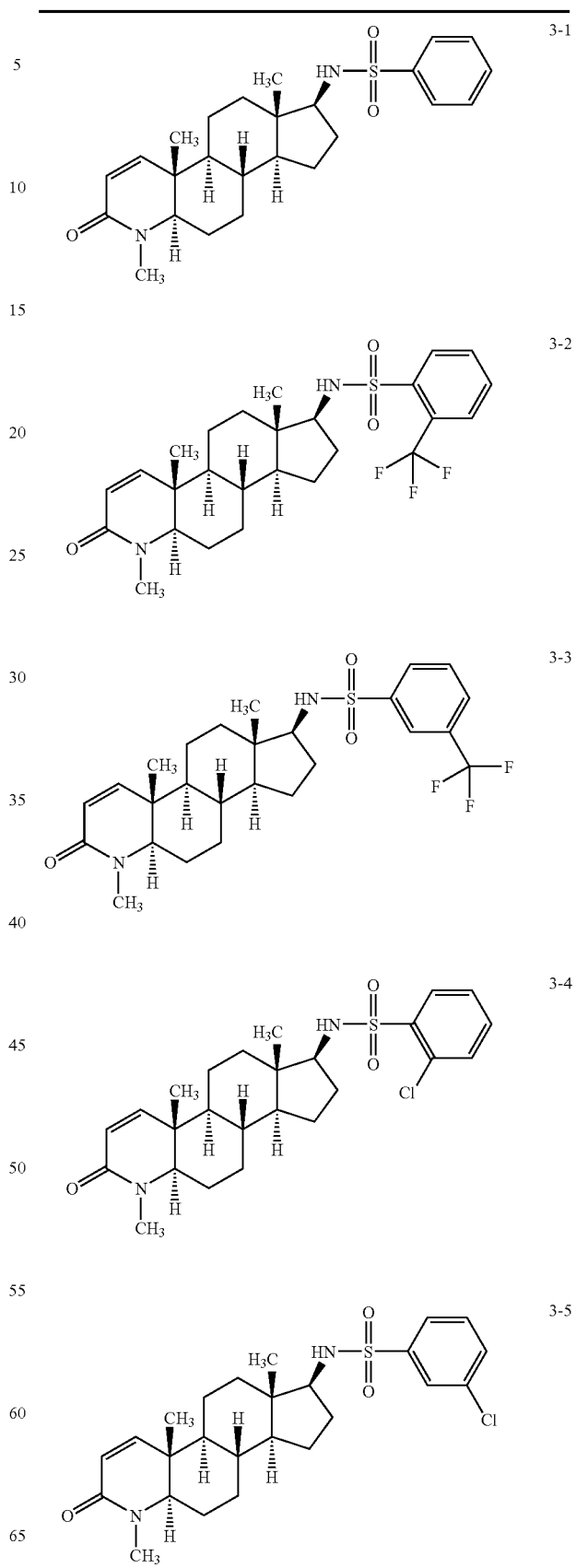

TABLE 5-continued
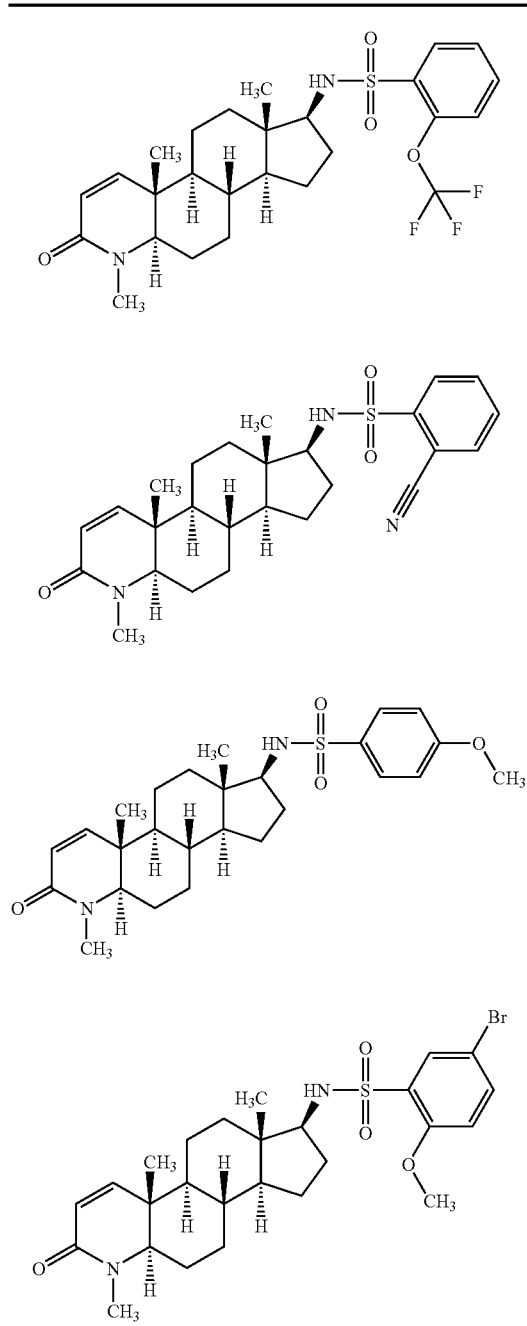
3-6
3-7
3-8
3-9
TABLE 5-continued
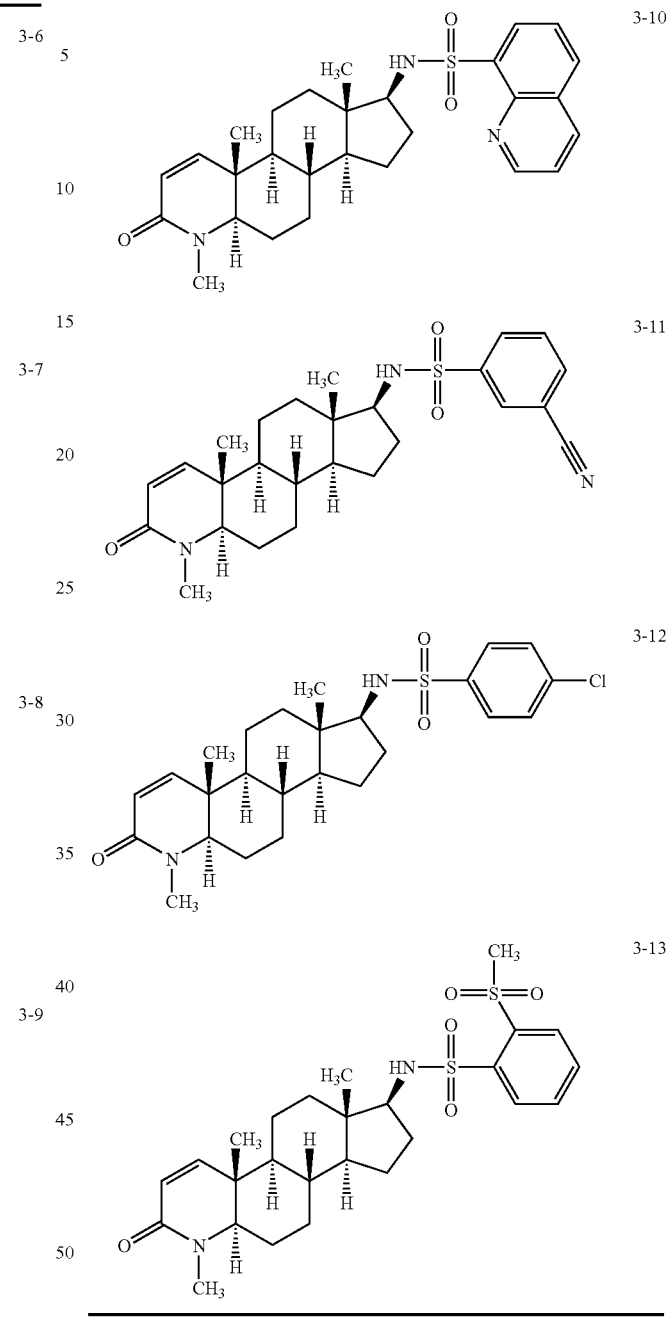
3-10
3-11
3-12
3-13
TABLE 6
| Compound Number | Name | [M + H]+ Found |
|---|---|---|
| 3-1 | 4-methyl-17β-(phenylsulfonamido)-4-aza-5α-androst-1-ene-3-one | 443.2376 |
| 3-2 | 4-methyl-17β-(2-trifluoromethylphenylsulfonamido)-4-aza-5α-androst-1-ene-3-one | 511.2260 |
| 3-3 | 4-methyl-17β-(3-trifluoromethylphenylsulfonamido)-4-aza-5α-androst-1-ene-3-one | 511.2268 |
| 3-4 | 4-methyl-17β-(2-chlorophenylsulfonamido)-4-aza-5α-androst-1-ene-3-one | 477.1990 |

TABLE 6-continued

| Compound Number | Name | [M + H]+ Found |
|---|---|---|
| 3-5 | 4-methyl-17β-(3-chlorophenylsulfonamido)-4-aza-5α-androst-1-ene-3-one | 477.1998 |
| 3-6 | 4-methyl-17β-(2-trifluoromethoxyphenylsulfonamido)-4-aza-5α-androst-1-ene-3-one | 527.2209 |
| 3-7 | 4-methyl-17β-(2-cyanophenylsulfonamido)-4-aza-5α-androst-1-ene-3-one | 468.2322 |
| 3-8 | 4-methyl-17β-(4-methoxyphenylsulfonamido)-4-aza-5α-androst-1-ene-3-one | 473.2492 |
| 3-9 | 4-methyl-17β-(3-bromo-5-methoxyphenylsulfonamido)-4-aza-5α-androst-1-ene-3-one | 551.1576 |
| 3-10 | 4-methyl-17β-(8-quinolylsulfonamido)-4-aza-5α-androst-1-ene-3-one | 494.2482 |
| 3-11 | 4-methyl-17β-(3-cyanophenylsulfonamido)-4-aza-5α-androst-1-ene-3-one | 468.2299 |
| 3-12 | 4-methyl-17β-(4-chlorophenylsulfonamido)-4-aza-5α-androst-1-ene-3-one | 477.1960 |
| 3-13 | 4-methyl-17β-[(2-methylsufonyl)phenyl]sulfonamido)-4-aza-5α-androst-1-ene-3-one | 521.2125 |

EXAMPLE 4

Preparation of N-[(5 α17β)-4-methyl-3-oxo-4-azaandrost-1-en-17-yl]-N'-phenyl urea (4-1)

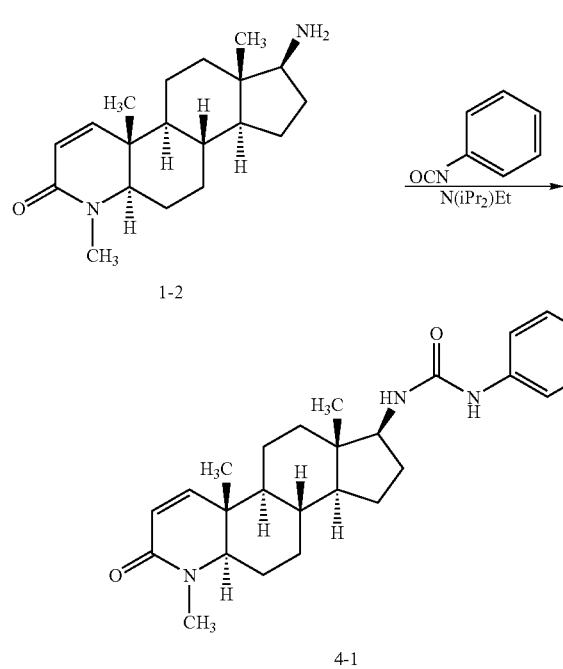

A mixture of 1-2 (1.0 g, 3.31 mmol), diisopropyethylamine (0.09 mL), phenyl isocyanate (0.047 g, 0.41 mmol) and dichloromethane (1 mL) was stirred for 3 hours. The mixture was washed with 10% w/v aqueous potassium hydrogen sulfate and the resulting organics chromatographed on silica gel (0% to 100% ethyl acetate/hexanes) to give 4-1 as a solid.

HRMS (FAB, M+1) found 422.2793.

Utilizing the same general procedure as described for compound 4-1 in Example 4, and by varying the isocyanate reagent, compounds 4-2 through 4-17 were prepared (Table 7); mass spectral characterization of these compounds is listed in Table 8.

EXAMPLE 4-18

Preparation of N-[5α,17β)-4-methyl-3-oxo-4-azaandrost-1-en-17-yl]-N'-methyl urea (4-18)

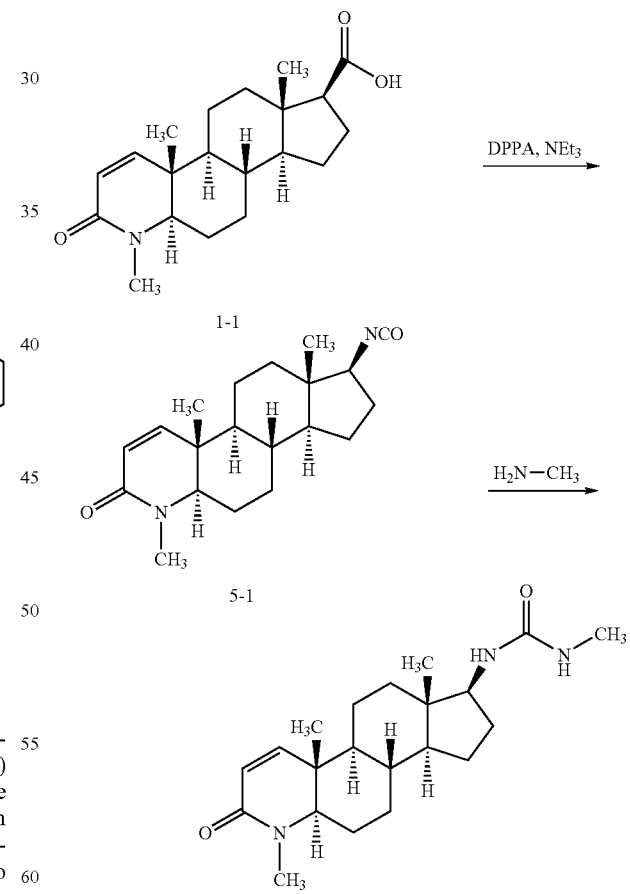

A mixture of 1-1 (1.0 g, 3.02 mmol), diphenylphosphoryl azide (1.0 g, 3.62 mmol), triethylamine (0.46 g, 4.53 mmol) and toluene (100 mL) was heated at reflux for 15 hours. After cooling to ambient temperature, the mixture was washed with 10% w/v aqueous potassium carbonate and dried over magnesium sulfate. Evaporation of the solvents gave 5-1 (1.0 g, 100%) as a yellow solid. A mixture of the crude isocyanate (0.1 g, 0.3 mmol), diisopropyethylamine (0.12 mL), methylamine hydrochloride (0.21 g, 0.3 mmol) and dichloromethane (1 mL) was stirred for 15 hours. The mixture was washed with 10% w/v aqueous potassium carbonate and dried over magnesium sulfate. Evaporation of the solvents gave a residue which was chromatographed on silica gel (0% to 100% ethyl acetate/hexanes) to give 4-18 (0.027 g, 25%) as a solid.

HRMS (FAB, M+1) found 360.2680.

Utilizing the same general procedure as described for compound 4-18 in Examples 4-18, and by varying the amine reagent, compounds 4-19 through 4-22 were prepared (Table 7); mass spectral characterization of these compounds is listed in Table 8.

TABLE 7

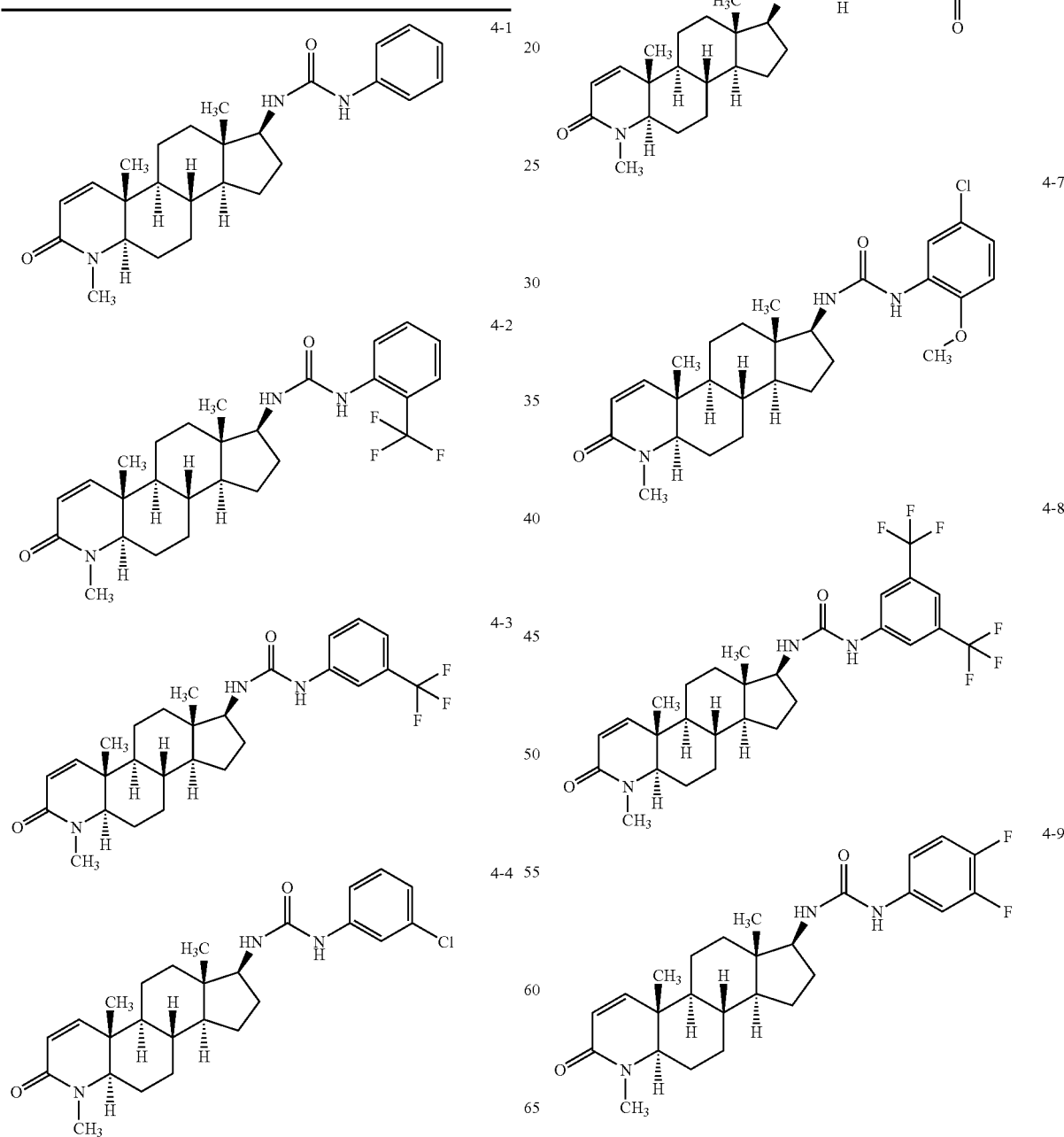

TABLE 7-continued
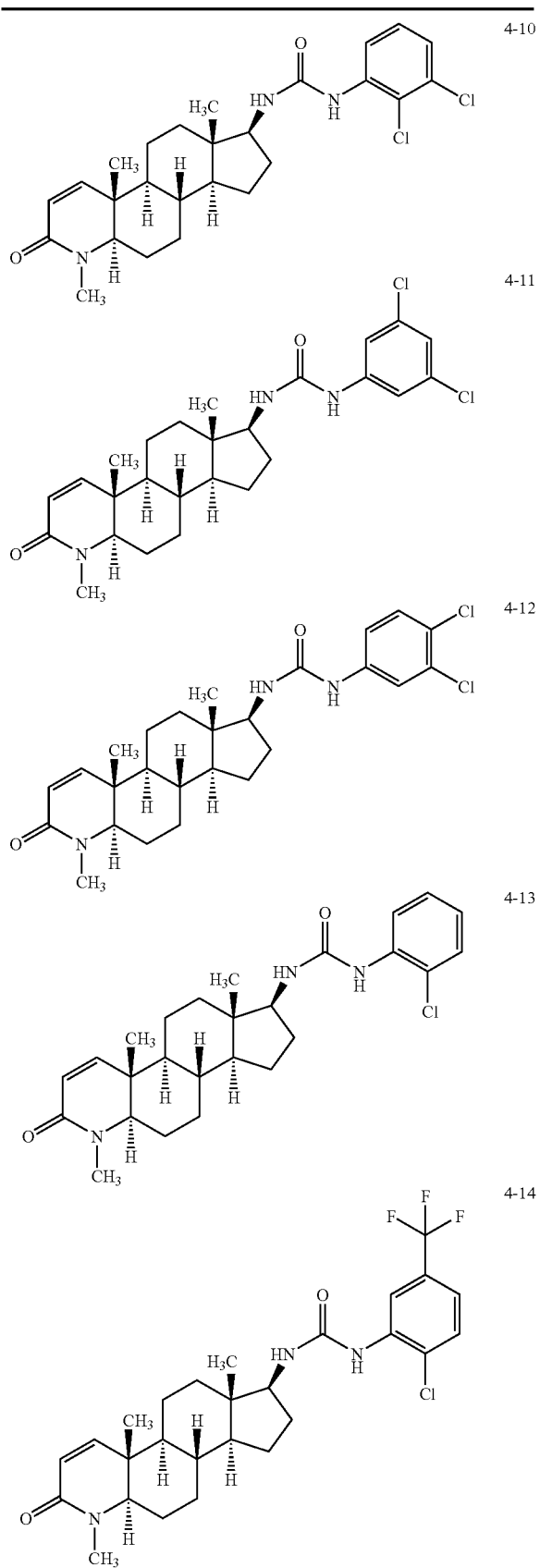
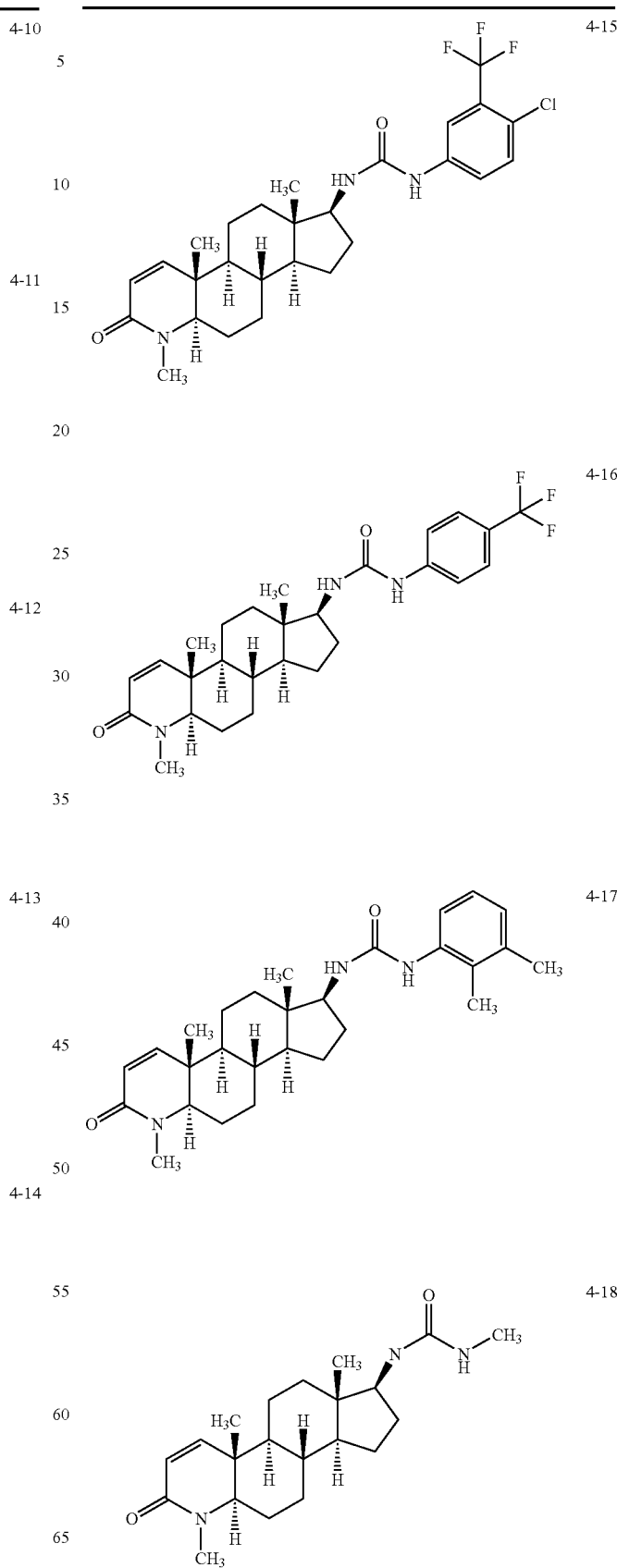

TABLE 7-continued

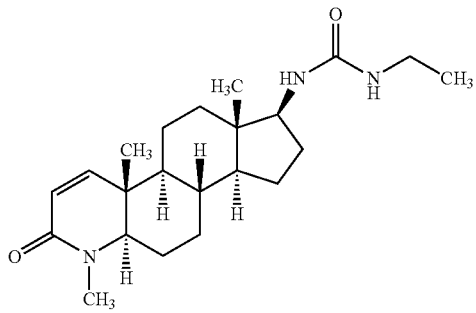

4-19

4-20

TABLE 7-continued

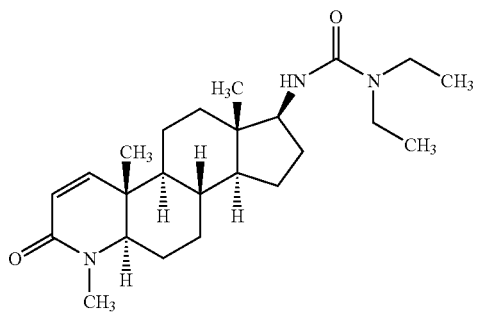

4-21

4-22

TABLE 8

| Compound Number | Name | Found [M + H]+ |
|---|---|---|
| 4-1 | N-[(5α,17β)-4-methyl-3-oxo-4-azaandrost-1-en-17-yl]-N'-phenyl urea | 422.2793 |
| 4-2 | N-[(5α,17β)-4-methyl-3-oxo-4-azaandrost-1-en-17-yl]-N'-(2-trifluoromethyl)phenyl urea | 490.2669 |
| 4-3 | N-[(5α,17β)-4-methyl-3-oxo-4-azaandrost-1-en-17-yl]-N'-(3-trifluoromethyl)phenyl urea | 490.2665 |
| 4-4 | N-[(5α,17β)-4-methyl-3-oxo-4-azaandrost-1-en-17-yl]-N'-3-chlorophenyl urea | 456.2409 |
| 4-5 | N-[(5α,17β)-4-methyl-3-oxo-4-azaandrost-1-en-17-yl]-N'-(4-chloro-2-trifluoromethylphenyl) urea | 524.2287 |
| 4-6 | N-[(5α,17β)-4-methyl-3-oxo-4-azaandrost-1-en-17-yl]-N'-3-acetylphenyl urea | 464.2903 |
| 4-7 | N-[(5α,17β)-4-methyl-3-oxo-4-azaandrost-1-en-17-yl]-N'-(5-chloro-2-trifluoromethylphenyl) urea | 486.2512 |
| 4-8 | N-[(5α,17β)-4-methyl-3-oxo-4-azaandrost-1-en-17-yl]-N'-(2,4-[bistrifluoromethyl]phenyl) urea | 558.2533 |
| 4-9 | N-[(5α,17β)-4-methyl-3-oxo-4-azaandrost-1-en-17-yl]-N'-(3,4-difluorophenyl) urea | 458.2610 |
| 4-10 | N-[(5α,17β)-4-methyl-3-oxo-4-azaandrost-1-en-17-yl]-N'-(2,3-dichlorophenyl) urea | 490.2017 |
| 4-11 | N-[(5α,17β)-4-methyl-3-oxo-4-azaandrost-1-en-17-yl]-N'-(2,4-dichlorophenyl) urea | 490.2020 |
| 4-12 | N-[(5α,17β)-4-methyl-3-oxo-4-azaandrost-1-en-17-yl]-N'-(3,4-dichlorophenyl) urea | 490.2018 |
| 4-13 | N-[(5α,17β)-4-methyl-3-oxo-4-azaandrost-1-en-17-yl]-N'-2-chlorophenyl) urea | 456.2402 |
| 4-14 | N-[(5α,17β)-4-methyl-3-oxo-4-azaandrost-1-en-17-yl]-N'-(2-chloro-5-trifluoromethylphenyl) urea | 524.2298 |
| 4-15 | N-[(5α,17β)-4-methyl-3-oxo-4-azaandrost-1-en-17-yl]-N'-(4-chloro-3-trifluoromethylphenyl) urea | 524.2299 |
| 4-16 | N-[(5α,17β)-4-methyl-3-oxo-4-azaandrost-1-en-17-yl]-N'-(4-trifluoromethyl)phenyl urea | 490.2681 |
| 4-17 | N-[(5α,17β)-4-methyl-3-oxo-4-azaandrost-1-en-17-yl]-N'-(2,3-dimethylpheny) urea | 450.3114 |
| 4-18 | N-[(5α,17β)-4-methyl-3-oxo-4-azaandrost-1-en-17-yl]-N'-methyl urea | 360.2680 |

TABLE 8-continued

| Compound Number | Name | Found [M + H]+ |
|---|---|---|
| 4-19 | N-[(5α,17β)-4-methyl-3-oxo-4-azaandrost-1-en-17-yl]-N'-ethyl urea | 374.2820 |
| 4-20 | N-[(5α,17β)-4-methyl-3-oxo-4-azaandrost-1-en-17-yl]-N'-dimethyl urea | 374.2761 |
| 4-21 | N-[(5α,17β)-4-methyl-3-oxo-4-azaandrost-1-en-17-yl]-N'-diethyl urea | 402.3158 |
| 4-22 | N-[(5α,17β)-4-methyl-3-oxo-4-azaandrost-1-en-17-yl] urea | 346.2489 |

EXAMPLE 4

Oral Composition

As a specific embodiment of an oral composition of a compound of this invention, 50 mg of a compound of the present invention is formatted with sufficient finely divided lactose to provide a total amount of 580 to 590 mg to fill a size 0 hard gelatin capsule.

EXAMPLE 5

Transdermal Patch Formulation

| Ingredient | Amount |
|---|---|
| Compound of formula I | 40 g |
| Silicone fluid | 45 g |
| Colloidal silicone dioxide | 2.5 g |

The silicone fluid and compound of structural formula I are mixed together and the colloidal silicone dioxide is added to increase viscosity. The material is then dosed into a subsequently heat sealed polymeric laminate comprised of the following: polyester release liner, skin contact adhesive composed of silicone or acrylic polymers, a control membrane which is a polyolefin (e.g. polyethylene, polyvinyl acetate or polyurethane), and an impermeable backing membrane made of a polyester multilaminate. The resulting laminated sheet is then cut into 10 cm² patches. For 100 Patches.

EXAMPLE 6

Suppository

| Ingredient | Amount |
|---|---|
| Compound of structural formula I | 25 g |
| Polyethylene glycol 1000 | 1481 g |
| Polyethylene glycol 4000 | 494 g |

The polyethylene glycol 1000 and polyethylene glycol 4000 are mixed and melted. The compound of structural formula I is mixed into the molten mixture, poured into molds and allowed to cool. For 1000 suppositories.

EXAMPLE 7

Injectable solution

| Ingredient | Amount |
|---|---|
| compound of structural formula I | 5 g |
| Buffering agents | q.s. |
| Propylene glycol | 400 mg |
| Water for injection | 600 mL |

The compound of structural formula I and buffering agents are dissolved in the propylene glycol at about 50° C. The water for injection is then added with stirring and the resulting solution is filtered, filled into ampules, sealed and sterilized by autoclaving. For 1000 Ampules.

EXAMPLE 8

Injectable solution

| Ingredient | Amount |
|---|---|
| Compound of structural formula I | 5 g |
| Buffering agents | q.s. |
| Magnesium sulfate heptahydrate | 100 mg |
| Water for injection | 880 mL |

The compound of structural formula I, magnesium sulfate heptahydrate and buffering agents are dissolved in the water for injection with stirring, and the resulting solution is filtered, filled into ampules, sealed and sterilized by autoclaving. For 1000 Ampules.

Following are assays to characterize the activity of the tissue selective androgen receptor modulators of the present invention.

In Vitro and in Vivo Assays for Identification of Compounds with SARM Activity

Hydroxylapatite-Based Radioligand Displacement Assay of Compound Affinity for Endogenously Expressed AR Materials:

Binding Buffer: TEGM (10 mM Tris-HCl, 1 mM EDTA, 10% glycerol, 1 mM beta-mercaptoethanol, 10 mM Sodium Molybdate, pH 7.2)

50% HAP Slurry: Calbiochem Hydroxylapatite, Fast Flow, in 10 mM Tris, pH 8.0 and 1 mM EDTA.

Wash Buffer: 40 mM Tris, pH7.5, 100 mM KCl, 1 mM EDTA and 1 mM EGTA. 95% EtOH
Methyltrienolone, [17a-methyl-$^3$H], (R1881*); NEN NET590
Methyltrienolone (R1881), NEN NLP005 (dissolve in 95% EtOH)
Dihydrotestosterone (DHT) [1,2,4,5,6,7-$^3$H(N)] NEN NET453
Hydroxylapatite Fast Flow; Calbiochem Cat#391947
Molybdate=Molybdic Acid (Sigma, M1651)

MDA-MB-453 Cell Culture Media:
  RPMI 1640 (Gibco 11835-055) w/23.8 mM NaHCO$_3$, 2 mM L-glutamine
  In 500 mL of complete media Final conc.
  10 mL (1 M Hepes) 20 mM
  5 mL (200 mM L-glu) 4 mM
  0.5 mL (10 mg/mL human insulin) 10 µg/mL in 0.01 N HCl Calbiochem#407694-S)
  50 mL BS (Sigma F2442) 10%
  1 mL (10 mg/mL Gentamicin 20 µg/mL Gibco#15710-072)

Cell Passaging:
  Cells (Hall R. E., et al., European Journal of Cancer, Vol. 30A (4), 484-490 (1994)) are rinsed twice in PBS, phenol red free Trypsin-EDTA is diluted in the same PBS 1:10. The cell layers are rinsed with 1× Trypsin, extra Trypsin is poured out, and the cell layers are incubated at 37° C. for ~2 min. The flask is tapped and checked to for signs of cell detachment. Once the cells are starting to sliding off the flask, the complete media is added to kill the trypsin. The cells are counted at this point, then diluted to the appropriate concentration and split into flasks or dishes for further culturing (Usually 1:3 to 1:6 dilution).

Preparation of MDA-MB453 Cell Lysate
  When the MDA cells are 70 to 85% confluent, they are detached as described above, and collected by centrifuging at 1000 g for 10 min at 4° C. The cell pellet is washed 2× with TEGM (10 mM Tris-HCl, 1 mM EDTA, 10% glycerol, 1 mM beta-mercaptoethanol, 10 mM Sodium Molybdate, pH 7.2). After the final wash, the cells are resuspended in TEGM at a concentration of $10^7$ cells/mL. The cell suspension is snap frozen in liquid N$_2$ or ethanol dry ice bath and transferred to −80° C. freezer on dry ice. Before setting up the binding assay, the frozen samples are left on ice-water to just thaw (~1 hr). Then the samples are centrifuged at 12,500 g to 20,000 g for 30 min at 4° C. The supernatant is used to set-up assay right away. If using 50 µL of supernatant, the test compound can be prepared in 50 µL of the TEGM buffer.

Procedure for Multiple Compound Screening:
  1× TEGM buffer is prepared, and the isotope-containing assay mixture is prepared in the following order: EtOH (2% final Conc. in reaction), $^3$H-R1881 or $^3$H-DHT (0.5 nM final Conc. in reaction) and 1×TEGM. [eg. For 100 samples, 200 µL (100×2) of EtOH+4.25 µL of 1:10 $^3$H-R1881 stock+2300 µL (100×23) 1× TEGM]. The compound is serially diluted, e.g., if starting final conc. is 1 µM, and the compound is in 25 µL of solution, for duplicate samples, 75 µL of 4×1 µM solution is made and 3 µL of 100 µM is added to 72 µL of buffer, and 1:5 serial dilution.
  25 µL of $^3$H-R1881 trace and 25 µL compound solution are first mixed together, followed by addition of 50 µL receptor solution. The reaction is gently mixed, spun briefly at about 200 rpm and incubated at 4° C. overnight. 100 µL of 50% HAP slurry is prepared and 100 µL of 50% HAP slurry is added to the incubated reaction which is then vortexed and incubated on ice for 5 to 10 minutes. The reaction mixture is vortexed twice more to resuspend HAP while incubating reaction. The samples in 96-well format are then washed in wash buffer using The FilterMate™ Universal Harvester plate washer (Packard). The washing process transfers HAP pellet containing ligand-bound expressed receptor to Unifilter-96 GF/B filter plate (Packard). The HAP pellet on the filter plate is incubated with 50 µL of MICROSCINT (Packard) scintillint for ½ hour before being counted on the TopCount micro scintillation counter (Packard). IC$_{50}$s are calculated using R1881 as a reference. Tissue selective androgen receptor modulators of the present invention typically have IC$_{50}$ values of 1 micromolar or less.

MMP1 Promoter Suppression, Transient Transfection Assay (TRAMPS)
  HepG2 cells are cultured in phenol red free MEM containing 10% charcoal-treated FCS at 37C with 5% CO$_2$. For transfection, cells are plated at 10,000 cells/well in 96 well white, clear bottom plates. Twenty four hours later, cells are co-transfected with a MMP1 promoter-luciferase reporter construct and a rhesus monkey expression construct (50:1 ratio) using FuGENE6 transfection reagent, following the protocol recommended by manufacture. The MMP1 promoter-luciferase reporter construct is generated by insertion of a human MMP1 promoter fragment (−179/+63) into pGL2 luciferase reporter construct (Promega) and a rhesus monkey AR expression construct is generated in a CMV-Tag2B expression vector (Stratagene). Cells are further cultured for 24 hours and then treated with ligands in the presence of 100 nM phorbol-12-myristate-13-acetate (PMA), used to increase the basal activity of MMP1 promoter. The ligands are added at this point, at a range of 1000 nM to 0.03 nM, 10 dilutions, at a concentration on 10×, ⅒th volume. (example: 10 microliters of ligand at 10× added to 100 microliters of media already in the well.) Cells are further cultured for additional 48 hours. Cells are then washed twice with PBS and lysed by adding 70 µL of Lysis Buffer (1 ×, Promega) to the wells. The luciferase activity is measured in a 96 well format using a 1450 Microbeta Jet (Perkin Elmer) luminometer. AR agonism of tissue selective androgen receptor modulators is presented as suppression of luciferase signal from the PMA-stimulated control levels EC$_{50}$ and Emax values are reported. Tissue selective androgen receptor modulators of the present invention typically agonize repression typically with submicromolar EC$_{50}$ values and Emax values greater than about 50%.

REFERENCES

1. Newberry E P, Willis D, Latifi T, Boudreaux J M, Towler D A. Fibroblast growth factor receptor signaling activates the human interstitial collagenase promoter via the bipartite Ets-AP1 element. Mol Endocrinol. 1997 July; 11(8): 1129-44.
2. Schneikert J, Peterziel H, Defossez P A, Klocker H, Launoit Y, Cato A C. Androgen receptor-Ets protein interaction is a novel mechanism for steroid hormone-mediated down-modulation of matrix metalloproteinase expression. J Biol Chem. 1996 Sep. 27; 271(39):23907-13.

A Mammalian Two-Hybrid Assay for the Ligand-induced Interaction of N-Terminus and C-Terminus Domains of the Androgen Receptor (Agonist Mode)
  This assay assesses the ability of AR agonists to induce the interaction between the N-terminal domain (NTD) and C-terminal domain (CTD) of rhAR that reflects the in vivo virilizing potential mediated by activated androgen receptors. (ref. 1). The interaction of NTD and CTD of rhAR is quantified as ligand induced association between a Gal4, DBD-rhARCTD fusion protein and a VP16-rhARNTD fusion protein as a mammalian two-hybrid assay in CV-1 monkey kidney cells.

The day before transfection, CV-1 cells are trypsinized and counted, and then plated at 20,000 cells/well in 96 well plates or larger plates (scaled up accordingly) in DMEM+ 10% FCS. The next morning, CV-1 cells are cotransfected with pCBB1 (Gal4DBD-rhARLBD fusion construct expressed under the SV40 early promoter), pCBB2 (VP16-rhAR NTD fusion construct expressed under the SV40 early promoter) and pFR (Gal4 responsive luciferase reporter, Promega) using LIPOFECTAMINE PLUS reagent (GIBCO-BRL) following the procedure recommended by the vendor. Briefly, DNA admixture of 0.05 μg pCBB1, 0.05 μg pCBB2 and 0.1 ug of pFR is mixed in 3.4 uL OPTI-MEM (GIBCO-BRL) is mixed with "PLUS Reagent" (1.6 μL, GIBCO-BRL) and incubated at room temperature (RT) for 15 min to form the pre-complexed DNA.

For each well, 0.4 μL LIPOFECTAMINE Reagent (GIBCO-BRL) is diluted into 4.6 μL OPTI-MEM in a second tube and mixed to form the diluted LIPO-FECTAMINE Reagent. The pre-complexed DNA (above) and the diluted LIPOFECTAMINE Reagent (above) are combined, mixed and incubated for 15 min at RT. The medium on the cells is replaced with 40 μL/well OPTI-MEM, and 10 μL DNA-lipid complexes are added to each well. The complexes are mixed into the medium gently and incubate at 37° C. at 5% $CO_2$ for 5 h. Following incubation, 200 μL/well D-MEM and 13% charcoal-stripped FCS is added, followed by incubation at 37° C. at 5% $CO_2$ After 24 hours, the test compounds are added at the desired concentration(s) (1 nM-10 μM). Forty eight hours later, luciferase activity is measured using LUC-Screen system (TROPIX) following the manufacture's protocol. The assay is conducted directly in the wells by sequential addition of 50 μL each of assay solution 1 followed by assay solution 2. After incubation for 40 minutes at room temperature, luminescence is directly measured with 2-5 second integration.

Activity of test compounds is calculated as the Emax relative to the activity obtained by 3 nM R1881. Typical tissue selective androgen receptor modulators of the present invention display weak or no agonist activity in this assay with less than 50% agonist activity at 10 micromolar.

REFERENCE

1. He B, Kemppainen J A, Voegel J J, Gronemeyer H, Wilson E M Activation function In the human androgen receptor ligand binding domain mediates inter-domain communication with the NH(2)-terminal domain. J Biol Chem. V 274: pp 37219-25, 1999.

A Mammalian Two-Hybrid Assay for Inhibition of Interaction between N-Terminus and C-Terminus Domains of Androgen Receptor (Antagonist Mode)

The assay assesses the ability of test compounds to antagonize the stimulatory effects of R1881 on the interaction between NTD and CTD of rhAR in a mammalian two-hybrid assay in CV-1 cells as described above.

Forty eight hours after transfection, CV-1 cells are treated with test compounds, typically at 10 μM, 3.3 μM, 1 μM, 0.33 μM, 100 nM, 33 nM, 10 nM, 3.3 nM and 1 nM final concentrations. After incubation at a 37° C. at 5% $CO_2$ for 10-30 minutes, an AR agonist methyltrienolone (R1881) is added to a final concentration of 0.3 nM and incubated at 37° C. Forty-eight hours later, luciferase activity is measured using LUC-Screen system (TROPIX) following the protocol recommended by the manufacture. The ability of test compounds to antagonize the action of R1881 is calculated as the relative luminescence compared to the value with 0.3 nM R1881 alone.

SARM compounds of the present invention typically display antagonist activity in the present assay and have $IC_{50}$ values less than 1 micromolar.

In Vivo Prostate Assay

Male Sprague-Dawley rats aged 9-10 weeks, the earliest age of sexual maturity, are used in prevention mode. The goal is to measure the degree to which androgen-like compounds delay the rapid deterioration (~-85%) of the ventral prostate gland and seminal vesicles that occurs during a seven day period after removal of the testes (orchidectomy [ORX]).

Rats are orchidectomized (ORX). Each rat is weighed, then anesthetized by isoflurane gas that is maintained to effect. A 1.5 cm anteroposterior incision is made in the scrotum. The right testicle is exteriorized. The spermatic artery and vas deferens is ligated with 4.0 silk 0.5 cm proximal to the testicle. The testicle is freed by one cut of a small surgical scissors distal to the ligation site. The tissue stump is returned to the scrotum. The same is repeated for the left testicle. When both stumps are returned to the scrotum, the scrotum and overlying skin are sutured closed with 4.0 silk. For Sham-ORX, all procedures excepting ligation and scissors cutting are completed. The rats fully recover consciousness and full mobility within 10-15 minutes.

A dose of test compound is administered subcutaneously or orally to the rat immediately after the surgical incision is sutured. Treatment continues for an additional six consecutive days.

Necropsy and Endpoints

The rat is first weighed, then anesthetized in a $CO_2$ chamber until near death. Approximately 5 ml whole blood is obtained by cardiac puncture. The rat is then examined for certain signs of death and completeness of ORX. Next, the ventral portion of the prostate gland is located and blunt dissected free in a highly stylized fashion. The ventral prostate is blotted dry for 3-5 seconds and then weighed (VPW). Finally, the seminal vesicle is located and dissected free. The ventral seminal vesicle is blotted dry for 3-5 seconds and then weighed (SVWT).

Primary data for this assay are the weights of the ventral prostate and seminal vesicle. Secondary data include serum LH (luteinizing hormone and FSH (follicle stimulating hormone), and possible serum markers of bone formation and virilization. Data are analyzed by ANOVA plus Fisher PLSD post-hoc test to identify intergroup differences. The extent to which test compounds inhibit ORX-induced loss of VPW and SVWT is assessed.

In Vivo Bone Formation Assay

Female Sprague-Dawley rats aged 7-10 months are used in treatment mode to simulate adult human females. The rats have been ovariectomized (OVX) 75-180 days previously, to cause bone loss and simulate estrogen deficient, osteopenic adult human females. Pre-treatment with a low dose of a powerful anti-resorptive, alendronate (0.0028 mpk SC, 2x/wk) is begun on Day 0. On Day 15, treatment with test compound is started. Test compound treatment occurs on Days 15-31 with necropsy on Day 32. The goal is to measure the extent to which androgen-like compounds increase the amount of bone formation, shown by increased fluorochrome labeling, at the periosteal surface.

In a typical assay, nine groups of seven rats each are studied.

On Days 19 and 29 (fifth and fifteenth days of treatment), a single subcutaneous injection of calcein (8 mg/kg) is given to each rat.

Necropsy and Endpoints

The rat is first weighed, then anesthetized in a $CO_2$ chamber until near death. Approximately 5 mL whole blood is obtained by cardiac puncture. The rat is then examined for certain signs of death and completeness of OVX. First, the uterus is located, blunt dissected free in a highly stylized fashion, blotted dry for 3-5 seconds and then weighed (UW). The uterus is placed in 10% neutral-buffered formalin. Next, the right leg is disarticulated at the hip. The femur and tibia are separated at the knee, substantially defleshed, and then placed in 70% ethanol.

A 1 cm segment of the central right femur, with the femoral proximal-distal midpoint at its center, is placed in a scintillation vial and dehydrated and defatted in graded alcohols and acetone, then introduced to solutions with increasing concentrations of methyl methacrylate. It is embedded in a mixture of 90% methyl methacrylate:10% dibutyl phthalate, that is allowed to polymerize over a 48-72 hr period. The bottle is cracked and the plastic block is trimmed into a shape that conveniently fits the vice-like specimen holder of a Leica 1600 Saw Microtome, with the long axis of the bone prepared for cross-sectioning. Three cross-sections of 85 µm thickness are prepared and mounted on glass slides. One section from each rat that approximates the midpoint of the bone is selected and blind-coded. The periosteal surface of each section is assessed for total periosteal surface, single fluorochrome label, double fluorochrome label, and interlabel distance.

Primary data for this assay are the percentage of periosteal surface bearing double label and the mineral apposition rate (interlabel distance (µm)/10 d), semi-independent markers of bone formation. Secondary data include uterus weight and histologic features. Tertiary endpoints may include serum markers of bone formation and virilization. Data are analyzed by ANOVA plus Fisher PLSD post-hoc test to identify intergroup differences. The extent to which test compounds increase bone formation endpoint will be assessed.

While the foregoing specification teaches the principles of the present invention, with examples provided for the purpose of illustration, it will be understood that the practice of the invention encompasses all of the usual variations, adoptions, or modifications, as come within the scope of the following claims and their equivalents.

What is claimed is:

1. A compound according which is 4-methyl-17β-[(4-trifluoromethylphenyl)acetamido-4-aza-5α-androst-1-ene-3-one; or a pharmaceutically acceptable salt thereof.

* * * * *